US012551711B2

(12) United States Patent
Debock et al.

(10) Patent No.: US 12,551,711 B2
(45) Date of Patent: Feb. 17, 2026

(54) STIMULATION LEAD CONNECTION SYSTEM

(71) Applicant: SPR THERAPEUTICS, INC., Cleveland, OH (US)

(72) Inventors: Matthew G. Debock, Morrisville, NC (US); Joseph W. Boggs, II, Chapel Hill, NC (US); Matthew J. Wunzin, Cleveland, OH (US); Bradley A. Lewis, Lyndhurst, OH (US); Devin Sell, Brecksville, OH (US); David Youngberg, Cleveland, OH (US); Mark R. Stultz, Maple Grove, MN (US); Joe D'Albero, Cleveland, OH (US); Christopher T. Lefevere, Cleveland, OH (US); Brian Mullins, Cleveland, OH (US); Peter Meinz, Cleveland, OH (US); David Prince, Cleveland, OH (US); Russell Cluff, Cleveland, OH (US); William Harstig, Cleveland, OH (US); Kristin Murray, Cleveland, OH (US)

(73) Assignee: SPR THERAPEUTICS, INC., Cleveland, OH (US)

( * ) Notice: Subject to any disclaimer, the term of this patent is extended or adjusted under 35 U.S.C. 154(b) by 416 days.

(21) Appl. No.: 17/911,153

(22) PCT Filed: Mar. 15, 2021

(86) PCT No.: PCT/US2021/022366
§ 371 (c)(1),
(2) Date: Sep. 13, 2022

(87) PCT Pub. No.: WO2021/184004
PCT Pub. Date: Sep. 16, 2021

(65) Prior Publication Data

US 2023/0146724 A1 May 11, 2023

Related U.S. Application Data

(60) Provisional application No. 62/989,129, filed on Mar. 13, 2020.

(51) Int. Cl.
*A61N 1/375* (2006.01)
*A61N 1/05* (2006.01)

(52) U.S. Cl.
CPC ............ *A61N 1/3752* (2013.01); *A61N 1/05* (2013.01); *A61N 1/0558* (2013.01)

(58) Field of Classification Search
CPC ...... A61N 1/3752; A61N 1/05; A61N 1/0558; A61N 1/0456; A61N 1/0502;
(Continued)

(56) References Cited

U.S. PATENT DOCUMENTS 5,782,892 A 7/1998 Castle et al.
6,139,353 A 10/2000 Muz
(Continued)

FOREIGN PATENT DOCUMENTS

CN 104428032 A 3/2015
CN 105229860 A 1/2016
(Continued)

OTHER PUBLICATIONS

Partial Supplementary European Search Report in EP21767544.6, mailed Mar. 20, 2024, 12 pages.
(Continued)

*Primary Examiner* — Paula J Stice
(74) *Attorney, Agent, or Firm* — McDonald Hopkins LLC

(57) ABSTRACT

A lead connector system for use with electrical nerve stimulators is described herein. An example lead connector
(Continued)

for an electrical stimulator system includes a body, a blade, and an insert. The body includes a cable interface and defines lead ports. The blade is affixed to the body. The blade has at least one angled portion. The insert slidably connects to the body. The insert includes a handle and a chassis. The chassis defines a lead channel coaxial with the lead ports and blade channels transverse the lead channel to accept the blade. The angled portion of the blade provides electrical contact between the cable interface and a lead inserted into the lead channel and extending through at least one of the lead ports.

14 Claims, 57 Drawing Sheets

(58) Field of Classification Search
CPC .............. A61N 1/0504; A61N 1/36014; A61N 1/36017; A61N 1/3625; A61N 1/375; A61N 1/3754; A61N 1/3968; H01R 2201/12; H01R 4/2406; H01R 13/5224; H01R 13/20
See application file for complete search history.

(56) References Cited

U.S. PATENT DOCUMENTS

| | | | |
|---|---|---|---|
| 6,654,643 | B1 | 11/2003 | Schmid |
| 6,845,271 | B2 | 1/2005 | Fang et al. |
| 7,376,467 | B2 | 5/2008 | Thrope et al. |
| 8,249,713 | B2 | 8/2012 | Fang et al. |
| 8,463,383 | B2 | 6/2013 | Sakai et al. |
| 8,626,302 | B2 | 1/2014 | Bennett et al. |
| 8,700,177 | B2 | 4/2014 | Strother et al. |
| 8,788,046 | B2 | 7/2014 | Bennett et al. |
| 8,886,337 | B2 | 11/2014 | Bennett et al. |
| 8,954,153 | B2 | 2/2015 | Boggs et al. |
| 8,965,516 | B2 | 2/2015 | Bennett et al. |
| 9,248,289 | B2 | 2/2016 | Bennett et al. |
| 9,827,412 | B2 | 11/2017 | Bennett et al. |
| 9,855,427 | B2 | 1/2018 | Bennett et al. |
| 9,895,530 | B2 | 2/2018 | Boggs et al. |
| 10,283,879 | B2 | 5/2019 | Dendas et al. |
| 10,522,612 | B1 | 12/2019 | Liu |
| 2005/0255718 | A1 | 11/2005 | Mcleish |
| 2008/0009192 | A1 | 1/2008 | Kast et al. |
| 2011/0269350 | A1 | 11/2011 | Mehdizadeh et al. |
| 2015/0320991 | A1 | 11/2015 | Sabin et al. |
| 2016/0250466 | A1 | 9/2016 | Boggs et al. |
| 2016/0344111 | A1 | 11/2016 | Lucantonio |
| 2017/0239483 | A1 | 8/2017 | Mathur et al. |
| 2021/0316146 | A1* | 10/2021 | Debock .............. A61N 1/36057 |

FOREIGN PATENT DOCUMENTS

| | | | |
|---|---|---|---|
| CN | 108697897 | A | 10/2018 |
| EP | 3570378 | A1 | 11/2019 |

OTHER PUBLICATIONS

Patent Cooperation Treaty (PCT), International Search Report and Written Opinion for Application PCT/US2021/022366 filed Mar. 15, 2021, mailed Jul. 28, 2021, International Searching Authority, US.

* cited by examiner

STIMULATION LEAD CONNECTION SYSTEM

CROSS-REFERENCE TO RELATED APPLICATION

This application 35 U.S.C. § 371 national stage application of PCT Application No. PCT/US2021/022366 filed on Mar. 15, 2021 entitled "STIMULATION LEAD CONNECTION SYSTEM" which claims the benefit of U.S. Provisional Application No. 62/989,129, filed Mar. 13, 2020, each of which are incorporated by reference in their entireties.

GOVERNMENT LICENSE RIGHTS

This invention was made with government support under W81XWH-18-C-0329 awarded by the U.S. Army Medical Research and Development Command. The government has certain rights in the invention.

TECHNICAL FIELD

The present disclosure generally relates to an electrical nerve stimulators and, more specifically, a lead connector system for use with such stimulators.

BACKGROUND

Neurostimulation and brain stimulation can provide functional and/or therapeutic outcomes. While existing systems and methods provide benefits to individuals requiring neurostimulation, many quality of life issues still remain. For example, existing systems are performed solely in a clinical setting under the supervision of a clinician limiting the applicable uses and the time available for stimulation. Furthermore, the controllers utilized in these clinical settings, by today's standards, are relatively large and awkward to manipulate and transport.

There exist both external and implantable devices for providing neurostimulation in diverse therapeutic and functional restoration indications. These neurostimulators are able to provide treatment therapy to individual portions of the body. The operation of these devices typically includes use of an electrode placed either on the external surface of the skin and/or a surgically implanted electrode. In the case of external neurostimulators, surface electrodes and/or percutaneous lead(s) having one or more electrodes are used to deliver electrical stimulation to select portion(s) of the patient's body.

For example, transcutaneous electrical nerve stimulation ("TENS") is delivered through electrodes placed on the skin surface, but has not achieved widespread use due to discomfort of the therapy, muscle fatigue, and the limited efficacy. TENS is similar to electrical muscle stimulation, although the latter is intended for stimulating muscles rather than nerves.

Several clinical and technical issues associated with surface electrical stimulation have prevented it from becoming a widely accepted treatment method. First, stimulation of cutaneous pain receptors cannot be avoided resulting in stimulation-induced pain that limits patient tolerance and compliance. Second, electrical stimulation is delivered at a relatively high frequency to prevent stimulation-induced pain, which leads to early onset of muscle fatigue. Third, it is difficult to stimulate deep nerves with surface electrodes without stimulating overlying, more superficial nerves resulting in unwanted stimulation. Further still, clinical skill and intensive patient training is required to place surface electrodes reliably on a daily basis and adjust stimulation parameters to provide optimal treatment. The required daily maintenance and adjustment of a surface electrical stimulation system is a major burden on both patient and caregiver.

A number of previous systems for spinal cord stimulation (e.g., at the dorsal root ganglion) and/or other deep tissue stimulation require surgical implantation of electrodes and/or other devices for delivering the therapy. These therapies necessarily incur the cost and medical risks associated with invasive surgical procedures, and they may restrict the mobility of the patient, both in terms of the surgical procedure itself and, in some cases, in the post-operative activities an ambulatory patient may wish to engage in while in his or her home environment.

For example, U.S. Pat. No. 7,376,467 discloses a neuromuscular stimulation assembly including a steerable introducer defining an interior lumen that shields the electrode from contact with tissue during insertion. Electrodes suitable for this assembly may be transcutaneous or percutaneous. The assembly includes a carrier, adhesively held to the patient, having an electronics pod for generating the desired electrical current patterns and an optional power input bay to enable changing the batteries for the assembly. Electrical connections between the electrodes and the power source are established via troughs that are integrally formed on the pod.

As another example, U.S. Pat. No. 8,700,177 describes a system and method involving the use of an adhesive patch with a mounting structure directly mated to an electrical stimulation device. A percutaneous electrode is electrically coupled to the stimulation device. The device has a low profile and may be controlled wirelessly or by way of a plugged connection. A rechargeable battery powers the device, which may be inductively charged.

One of the issues associated with such percutaneous systems is lead dislodgment. This often occurs as the user or clinician attempts to remove the bandage around the lead. In such cases, the adhesive of the bandage may adhere to the lead and inadvertently cause it to dislodge. Specifically, as the user or clinician rips off the bandage it will often stick to the lead and as the bandage is removed from the skin of the user the lead remains adhere to it and is removed unintentionally. There is a need, therefore, for a system that prevents this from occurring.

SUMMARY

A lead connector system for use with electrical nerve stimulation devices is disclosed. The connector system includes, for example, an electrically passive connector base, a connector to serve as an interface between a cable and a lead, a lead anchor to promote stability of a lead, and/or a cover to protect the connector and/or the lead. In some examples, the connector base is adhered to the skin of the patient to detachably connect the connector to the patient. The connector includes (a) receiving ports that are, in some examples, in separate facings of the connector to receive the lead and the extension cable, and (b) a blade-like interface that establishes and maintains electrical contact between the lead and the cable. The lead anchor is configured to adhere to the lead and the patient relatively close to where the lead enters the skin to impede movement of the lead. A protective cover may be configured to form a barrier around the connector and the lead.

A lead connector system for use with electrical nerve stimulators is described herein. An example lead connector for an electrical stimulator system includes a body, a blade (s), and an insert. The body includes a cable interface and defines lead ports. The blade is affixed to the body. The blade has at least one angled portion. The insert slidably connects to the body. The insert includes a handle and a chassis. The chassis defines a lead channel coaxial with the lead ports and blade channels transverse the lead channel to accept the blade. The angled portion of the blade provides electrical contact between the cable interface and a lead inserted into the lead channel and extending through at least one of the lead ports.

An example lead connector for an electrical stimulator system includes a base, one or more blade(s), and a cover. The base includes a cable interface and define lead ports. The blade(s) is affixed to the body. The blade(s) has at least two sections transverse an axis defined by the lead ports. The cover rotatably connected to the base. The cover includes a handle, blade guides, and lead guides. The blade(s) guides defining blade channel(s) each to interface with a different one of the sections of the blade(s). A portion of each of the sections of the blade(s) provides electrical contact between the cable interface and a lead inserted into at least one of the lead ports.

A stimulation lead connection system includes a cable, a lead connector, and a connector base. The cable includes a magnetic breakaway connection at a proximal end, a head at a distal end, and may include additional magnetic breakaway connection(s) at the distal end. A lead connector electrically and mechanically interfaces with the head and electrically and mechanically interfaces with a lead at least partially covered in insulation. The connector base selectively receives the lead connector. The connector base includes an adhesive pad configured to adhere to skin of a patient.

These and other features and advantages of the present disclosure are set forth in the following specification, drawings and claims.

BRIEF DESCRIPTION

Operation of the disclosure may be better understood by reference to the following detailed description taken in connection with the following illustrations, wherein.

Figure 3A:
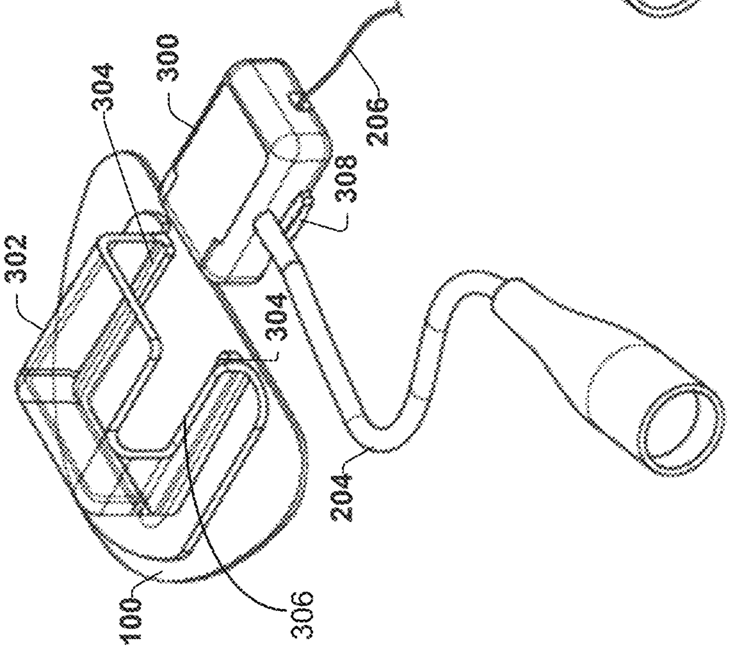
Figure 3B:
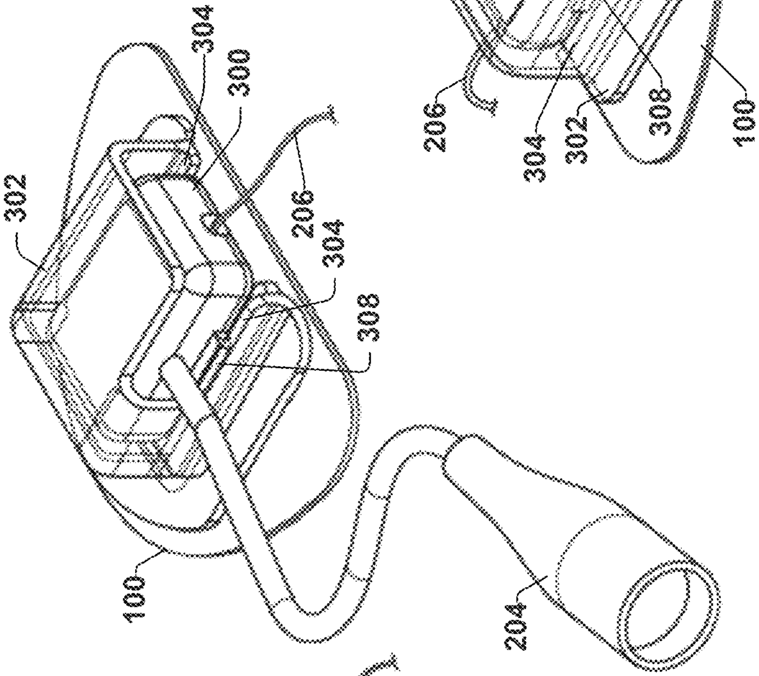
Figure 3C:
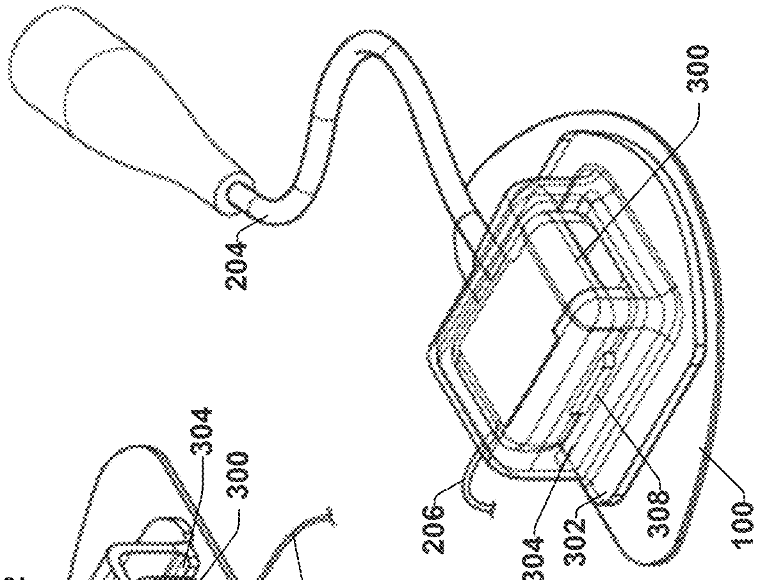

FIGS. 3A, 3B, and 3C illustrate another example connector that is slidably engageable with a connector base, in accordance with the teachings of this disclosure.

FIGS. 4A, 4B, 4C, 4D, and 4E illustrate an example connector that is vertically lockable with a connector base, in accordance with the teachings of this disclosure.

Figure 5A:
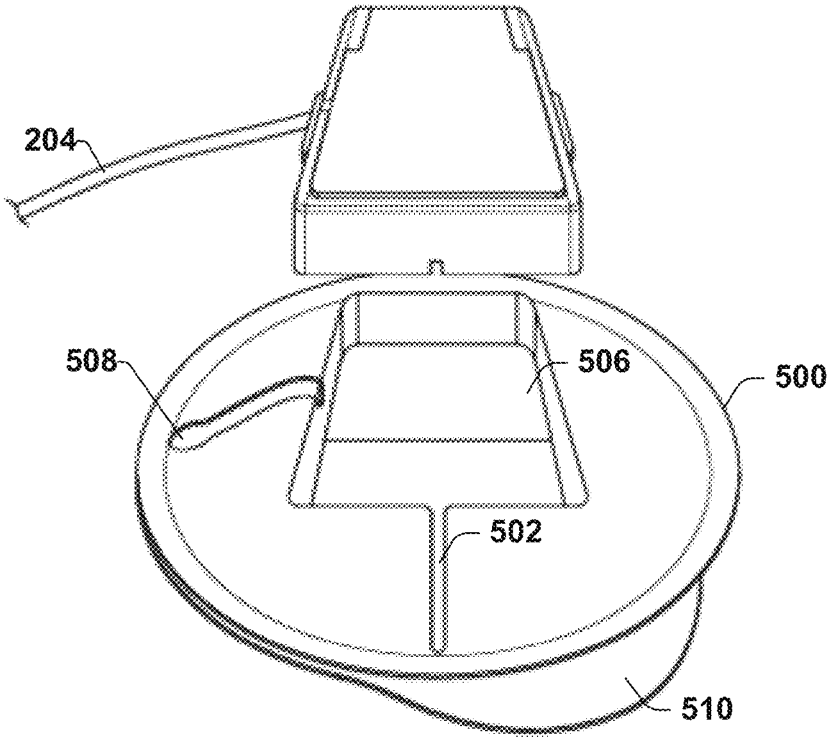
Figure 5B:
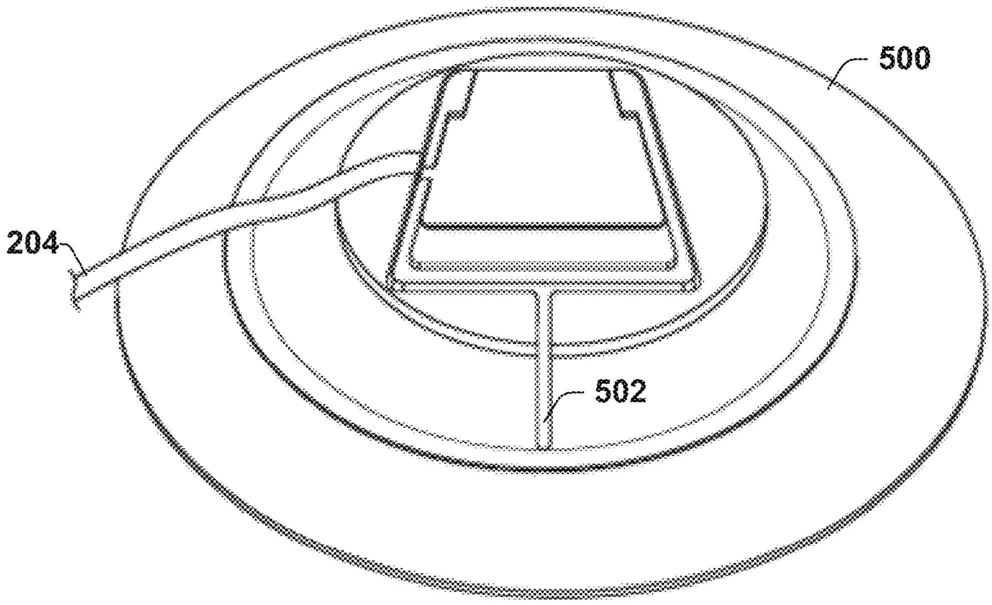

FIGS. 5A and 5B illustrate a molded connector base configured to receive the connector, in accordance with the teachings of this disclosure.

FIGS. 6A, 6B, 6C, 6D, 6E and 6F illustrate an example connector with a detachable cable, in accordance with the teachings of this disclosure.

FIGS. 7A, 7B, 7C, and 7D illustrate an example push lock connector, in accordance with the teachings of this disclosure.

Figure 8A:
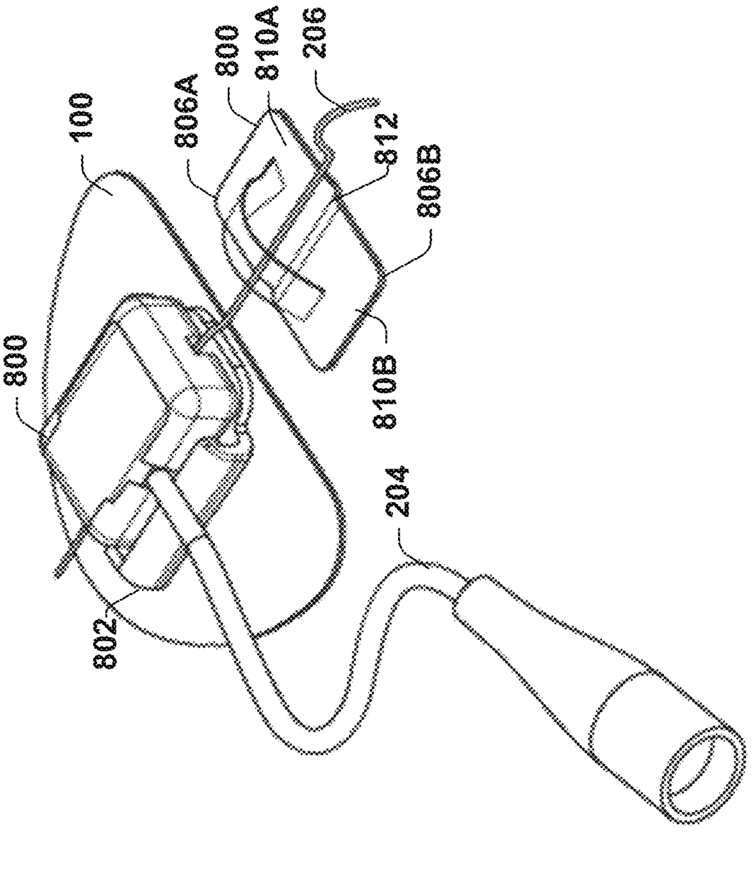
Figure 8B:
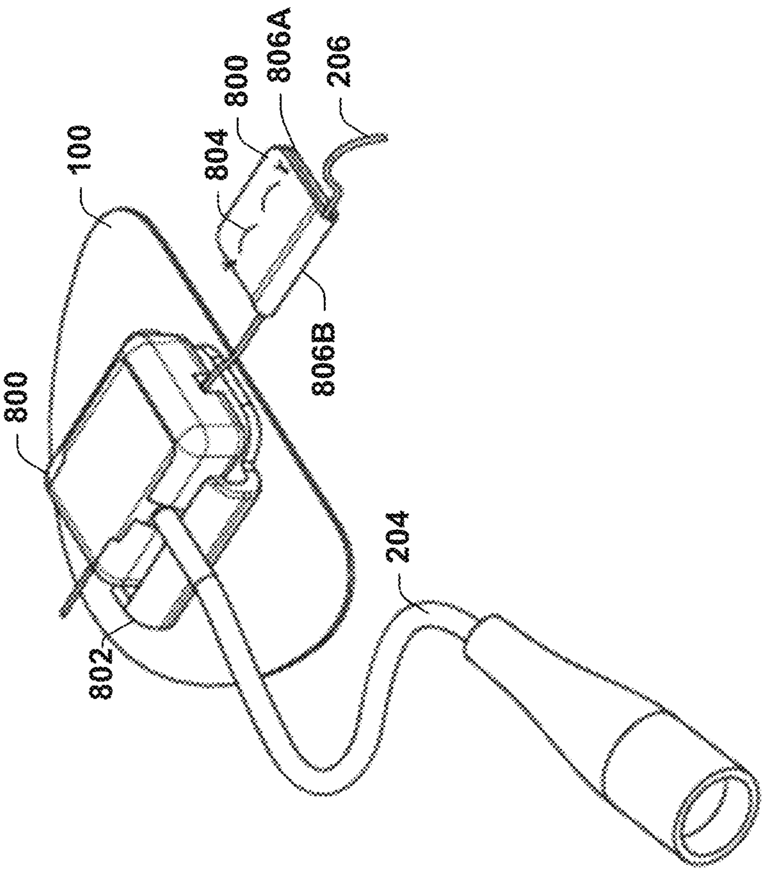
Figure 8C:
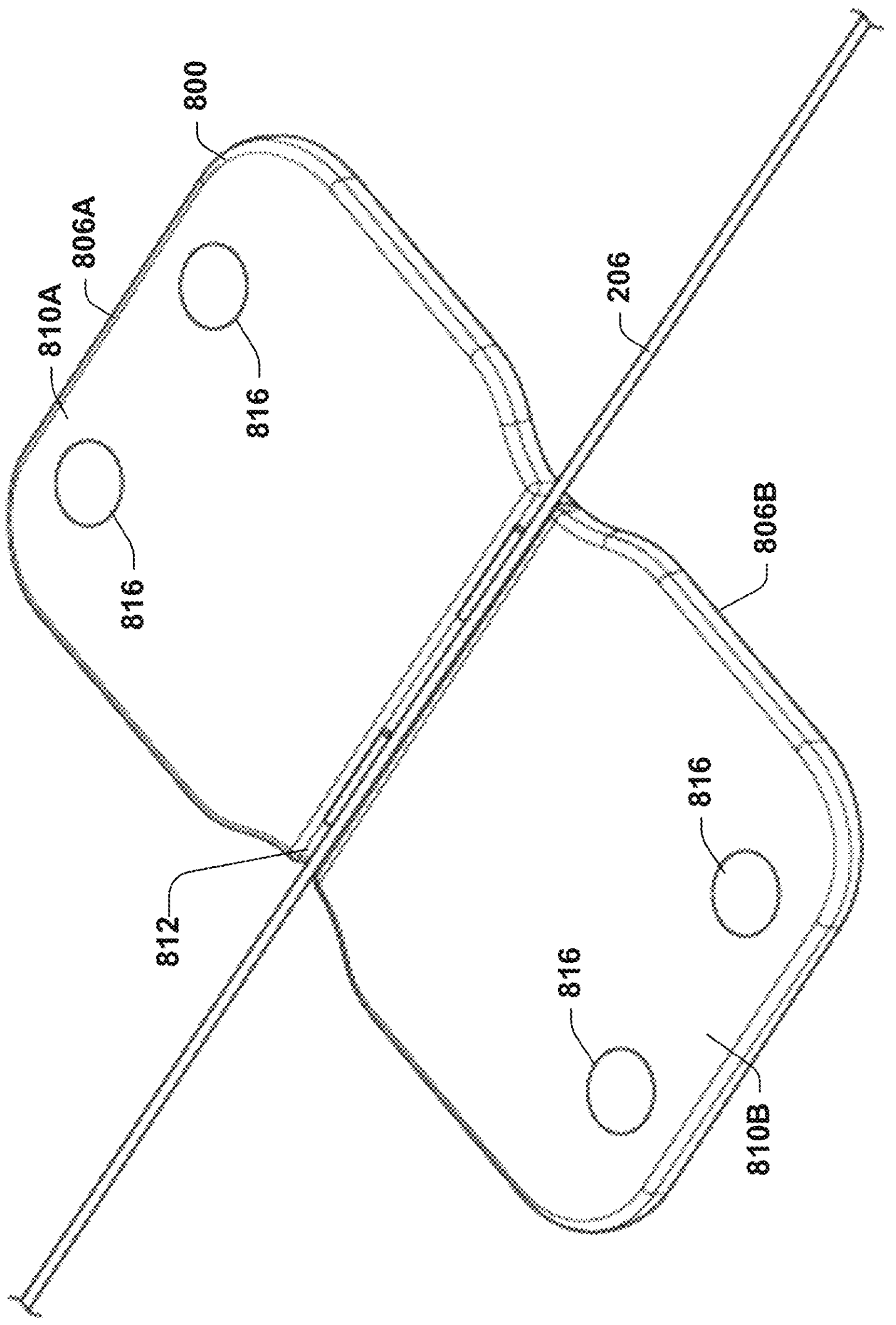

FIGS. 8A, 8B, and 8C illustrate an example folding lead anchor, in accordance with the teachings of this disclosure.

Figure 9A:
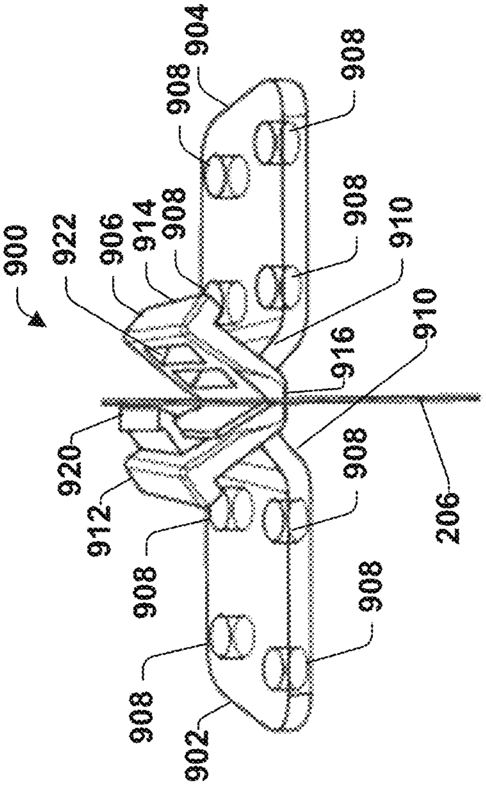
Figure 9B:
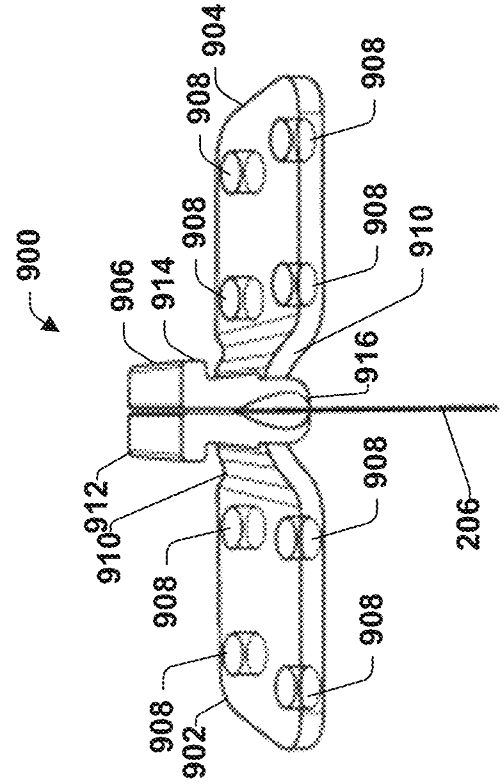
Figure 10B:
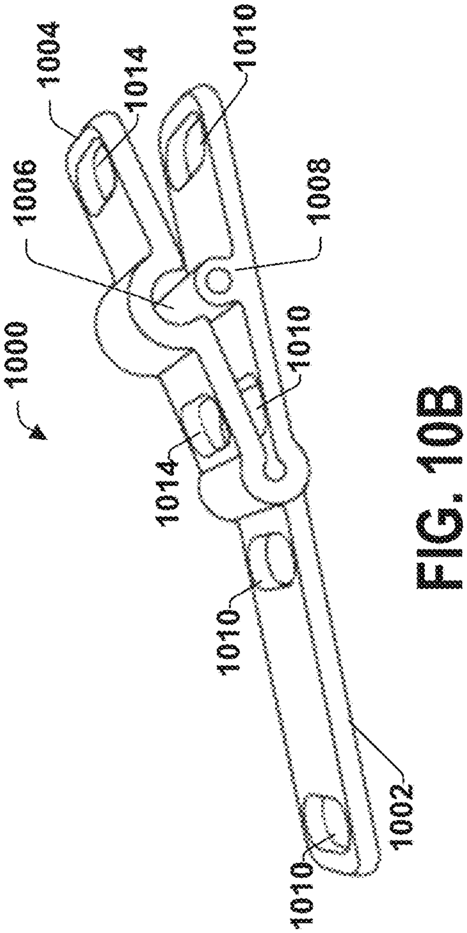
Figure 10D:
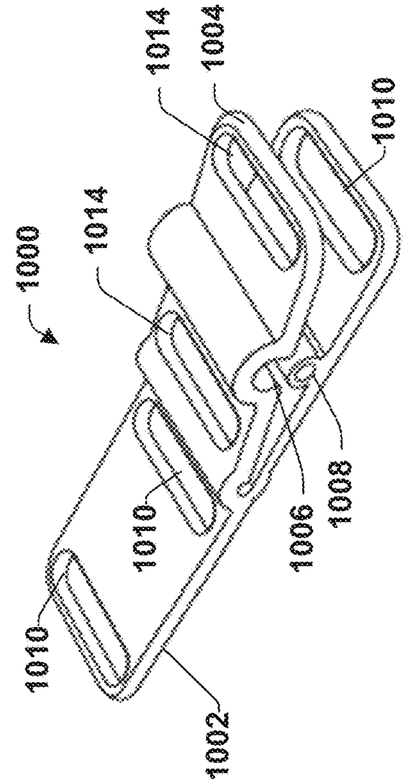
Figure 10A:
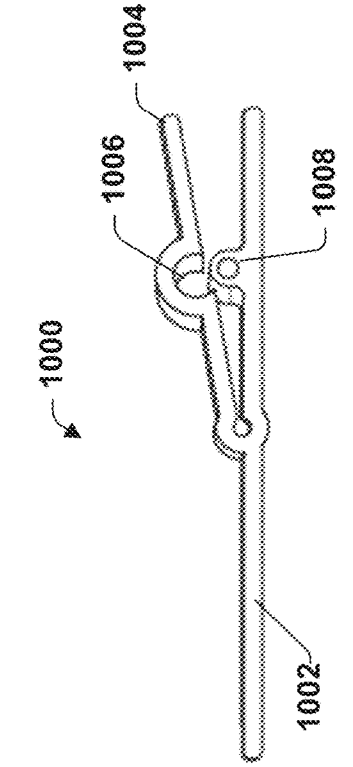
Figure 10C:
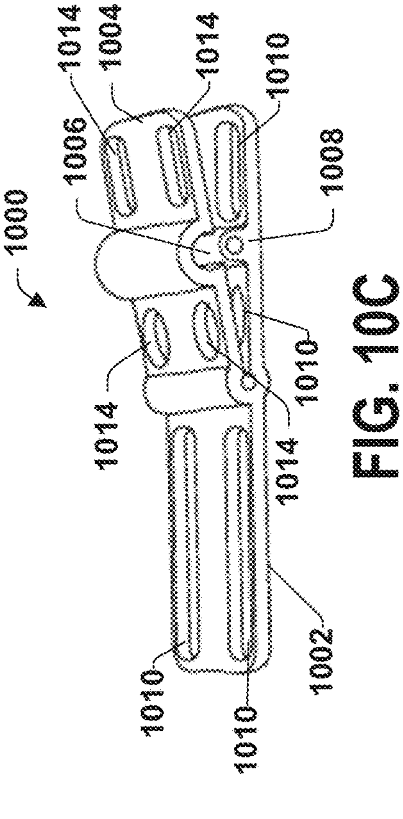

FIGS. 9A and 9B illustrate an example snapping lead anchor, in accordance with the teachings of this disclosure.

FIGS. 10A, 10B, 10C and 10D illustrate an example folding lead anchor, in accordance with the teachings of this disclosure.

Figure 11B:
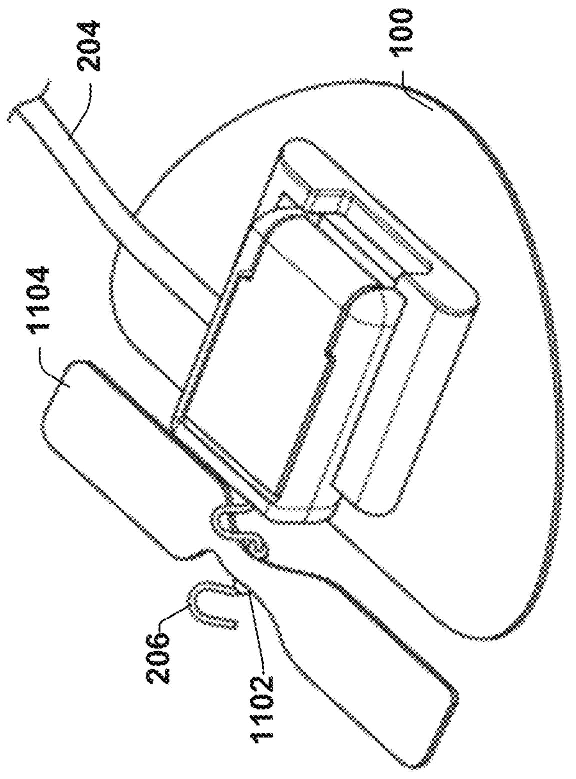
Figure 11A:
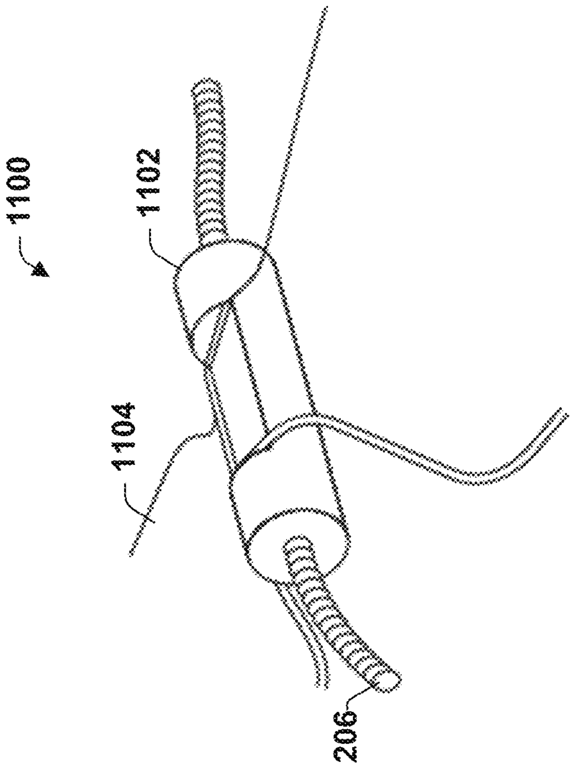

FIGS. 11A and 11B illustrate an example adhesive-based lead anchor, in accordance with the teachings of this disclosure.

Figure 12B:
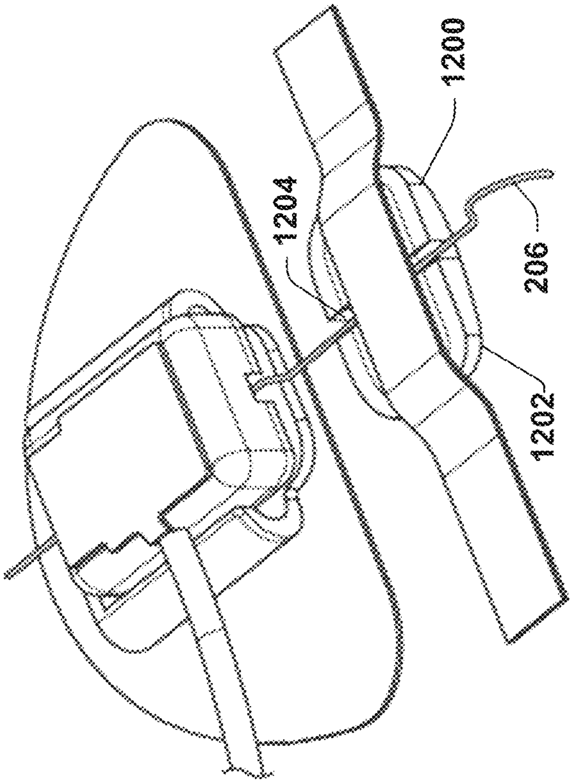
Figure 12A:
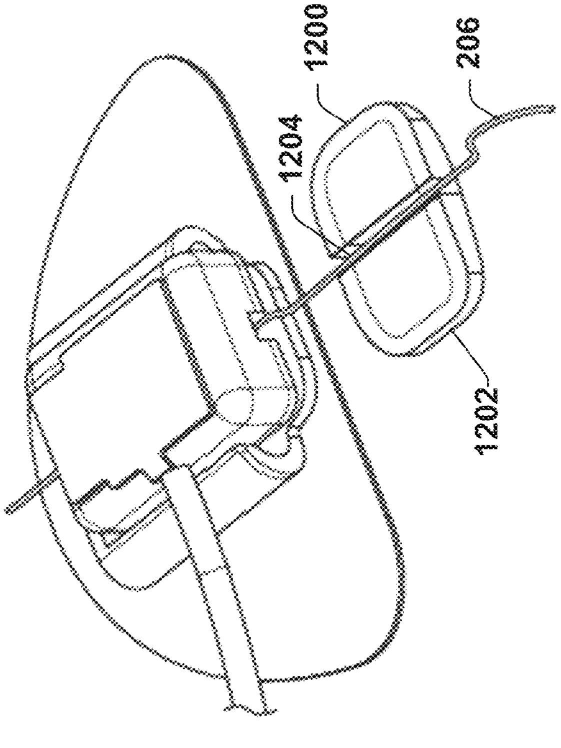

FIGS. 12A and 12B illustrate another example of an adhesive-based lead anchor, in accordance with the teachings of this disclosure.

Figure 13:
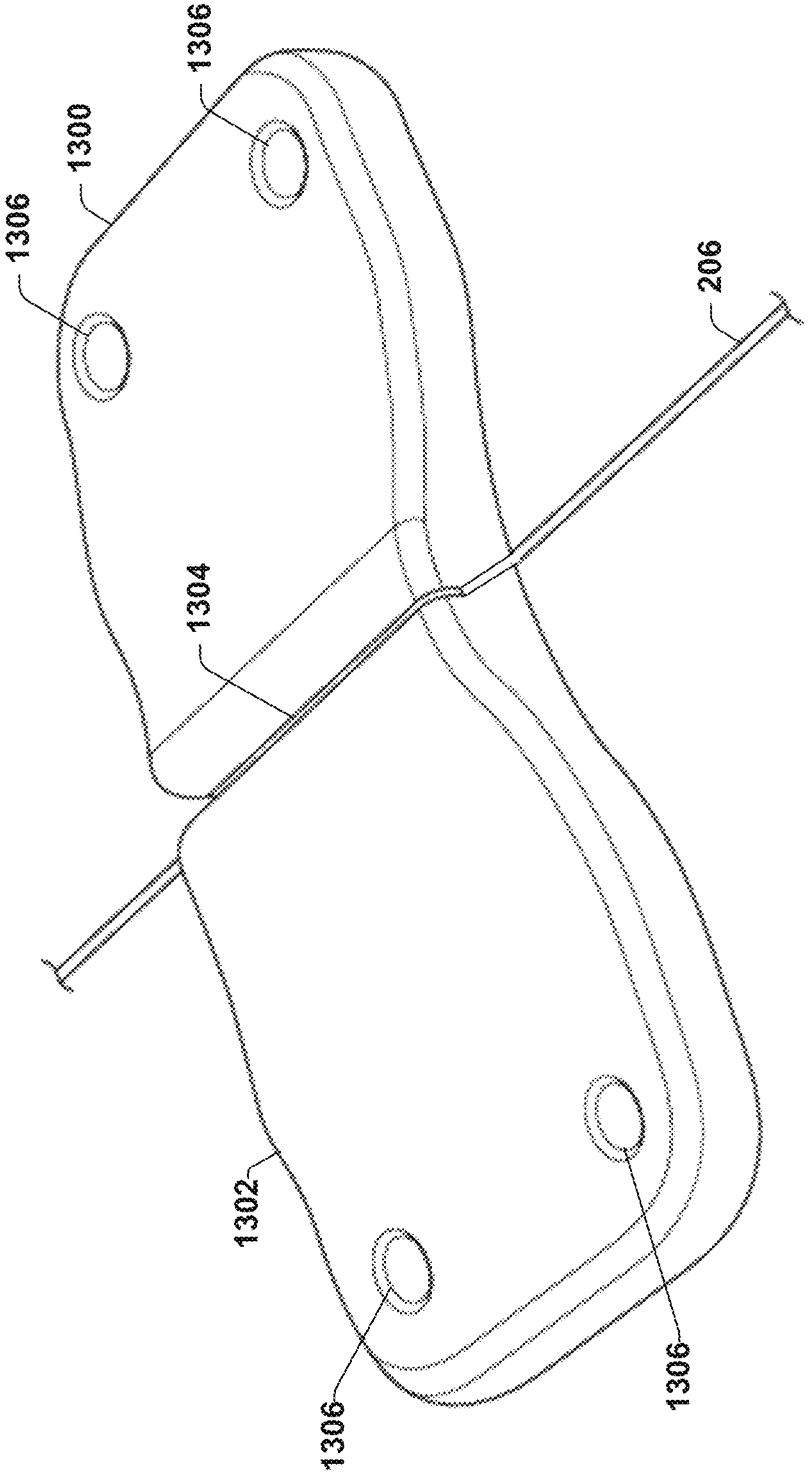

FIG. 13 illustrates an example dual purpose lead anchor, in accordance with the teachings of this disclosure.

Figure 14:
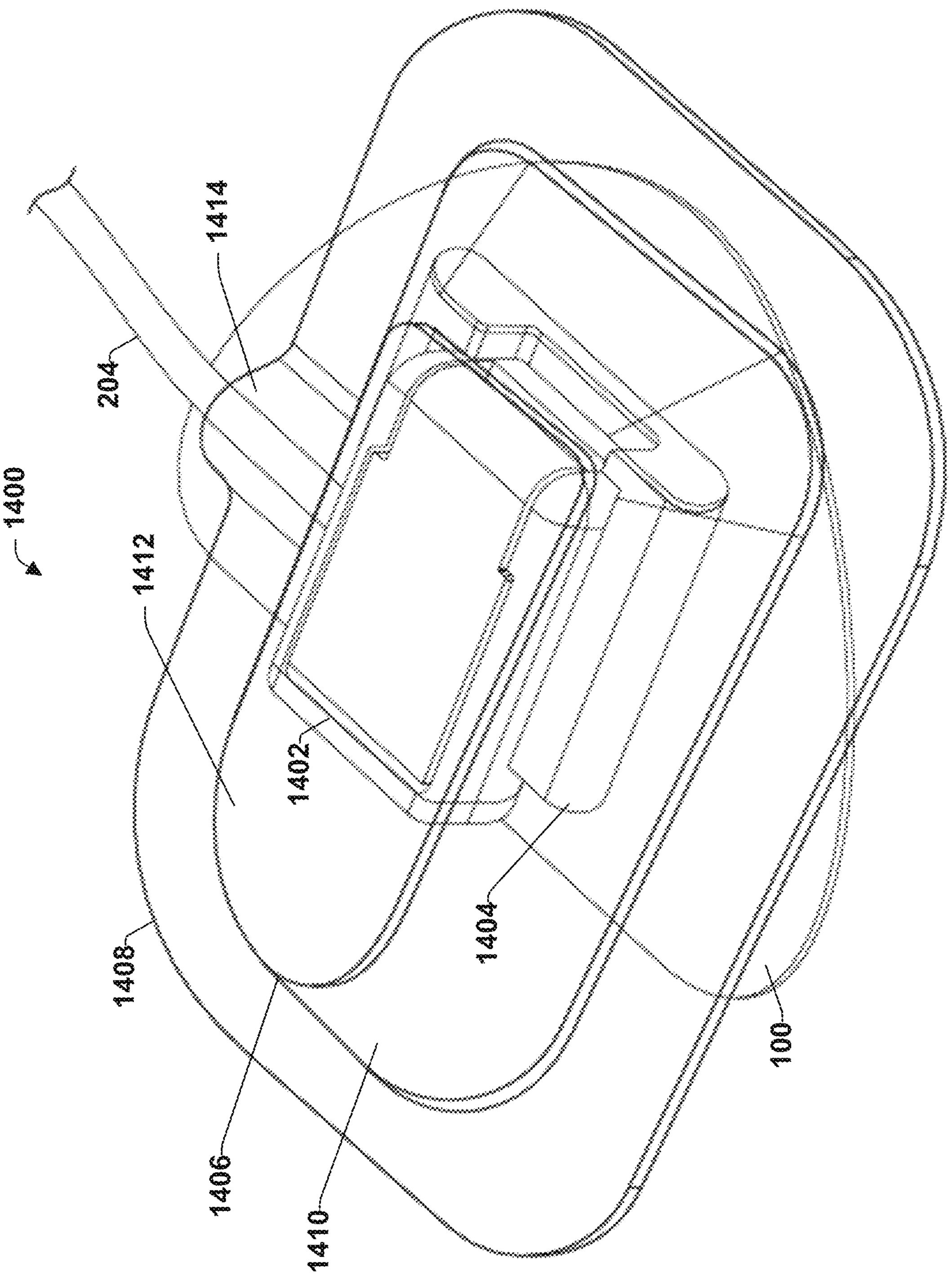

FIG. 14 illustrates an example protective cover, in accordance with the teachings of this disclosure.

Figure 15B:
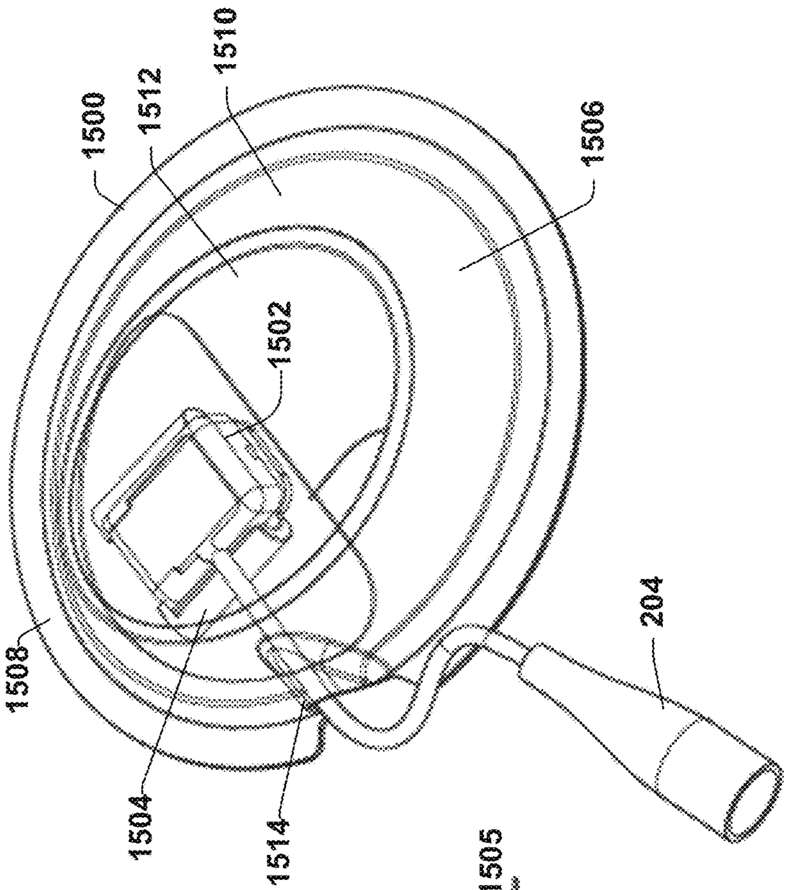
Figure 15A:
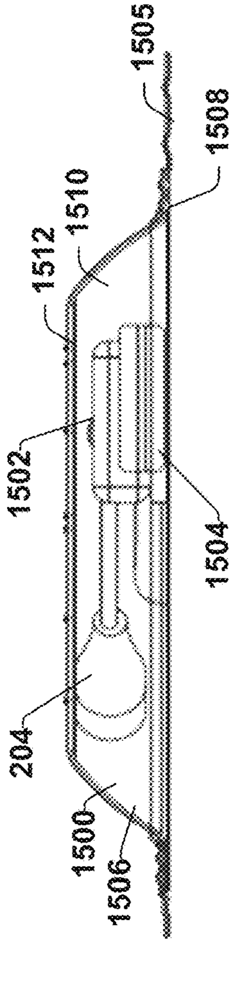

FIGS. 15A and 15B illustrate another example of a protective cover, in accordance with the teachings of this disclosure.

Figure 16A:
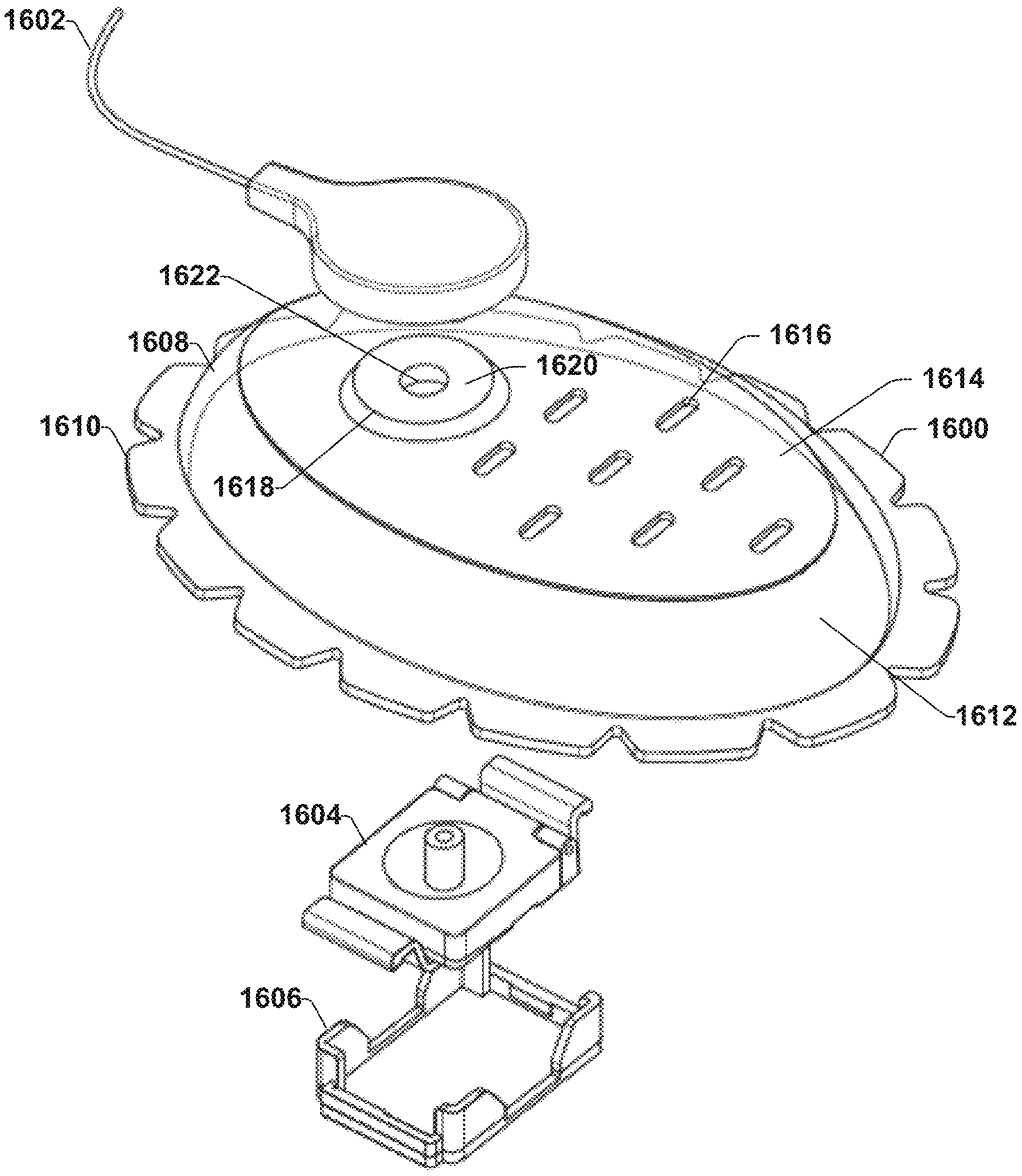
Figure 16B:
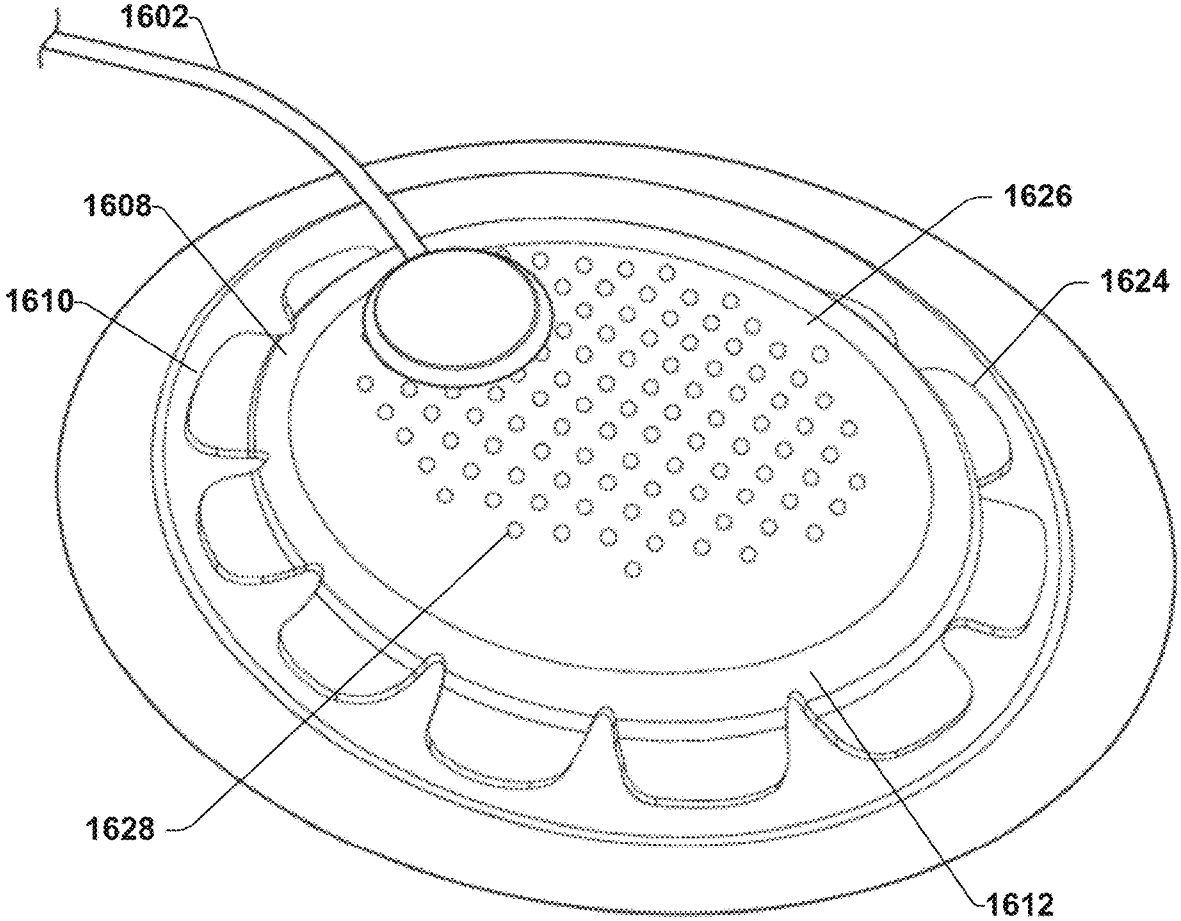
Figure 17B:
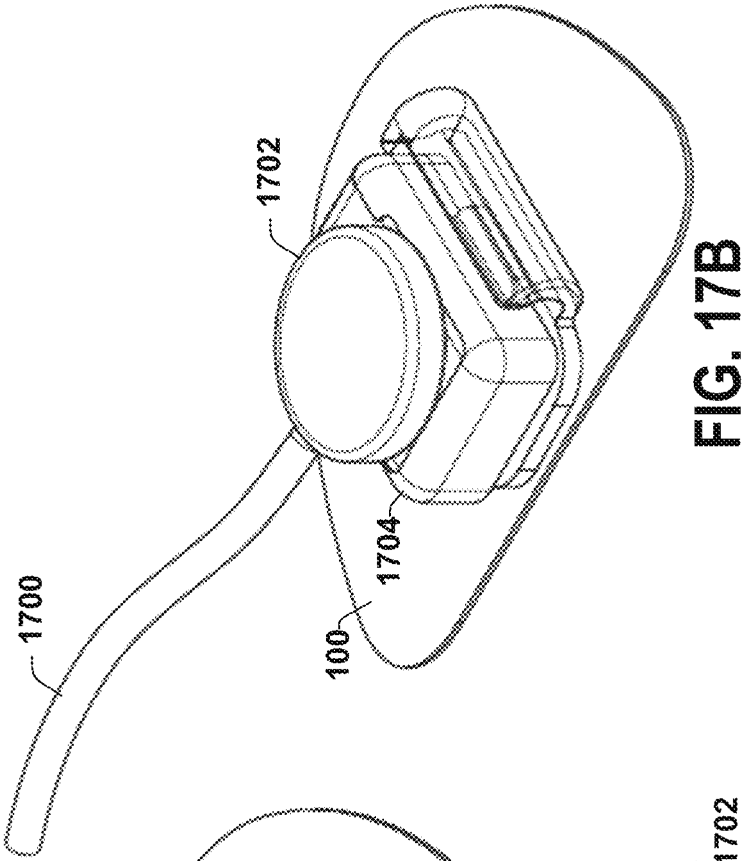
Figure 17D:
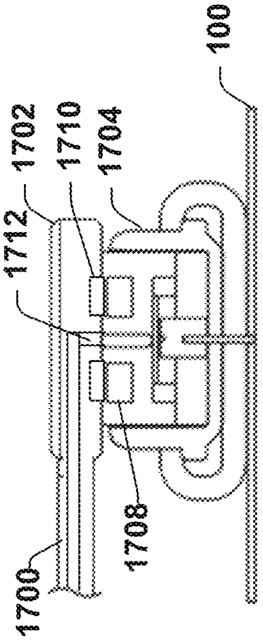
Figure 17A:
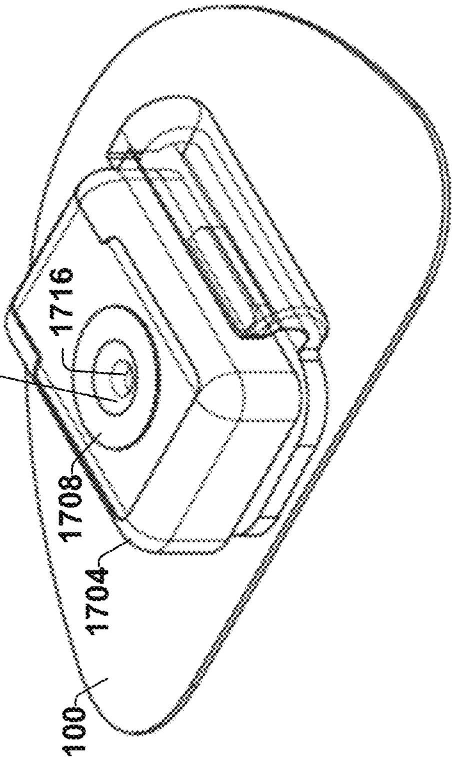
Figure 17C:
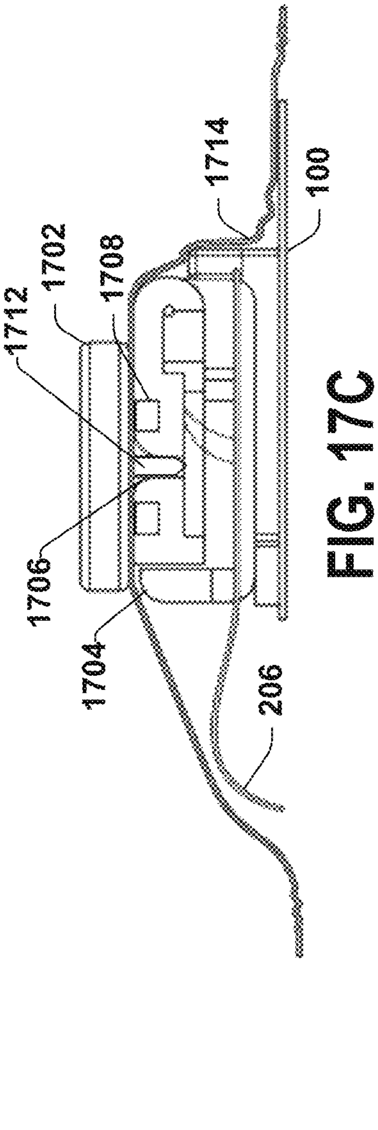

FIGS. 16A and 16B illustrate examples of protective covers configured such that the cable remains outside of the protective cover, in accordance with the teachings of this disclosure.

FIGS. 17A, 17B, 17C, and 17D illustrate a cable with a magnetic lead and a connector with a corresponding magnetic cradle, in accordance with the teachings of this disclosure.

Figure 18A:
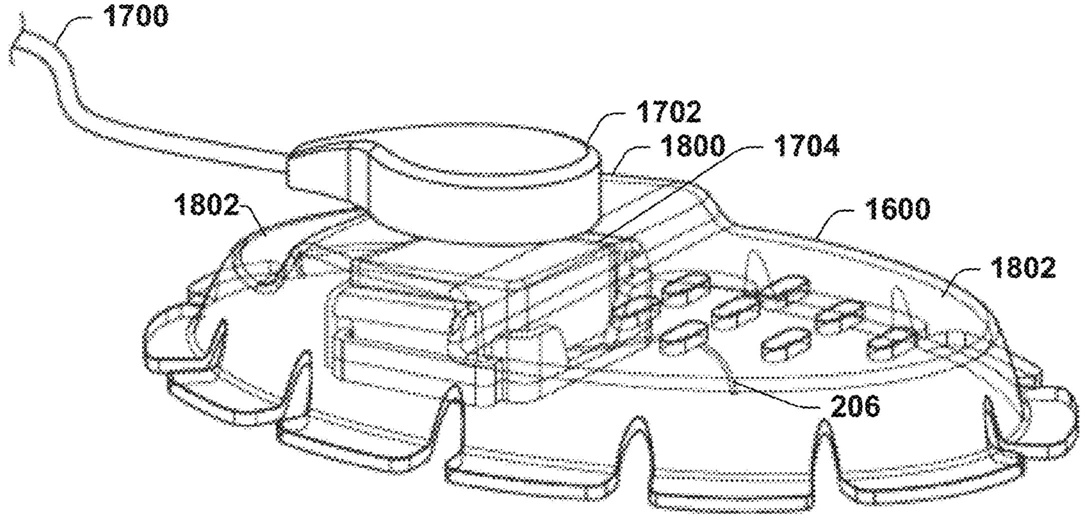
Figure 18B:
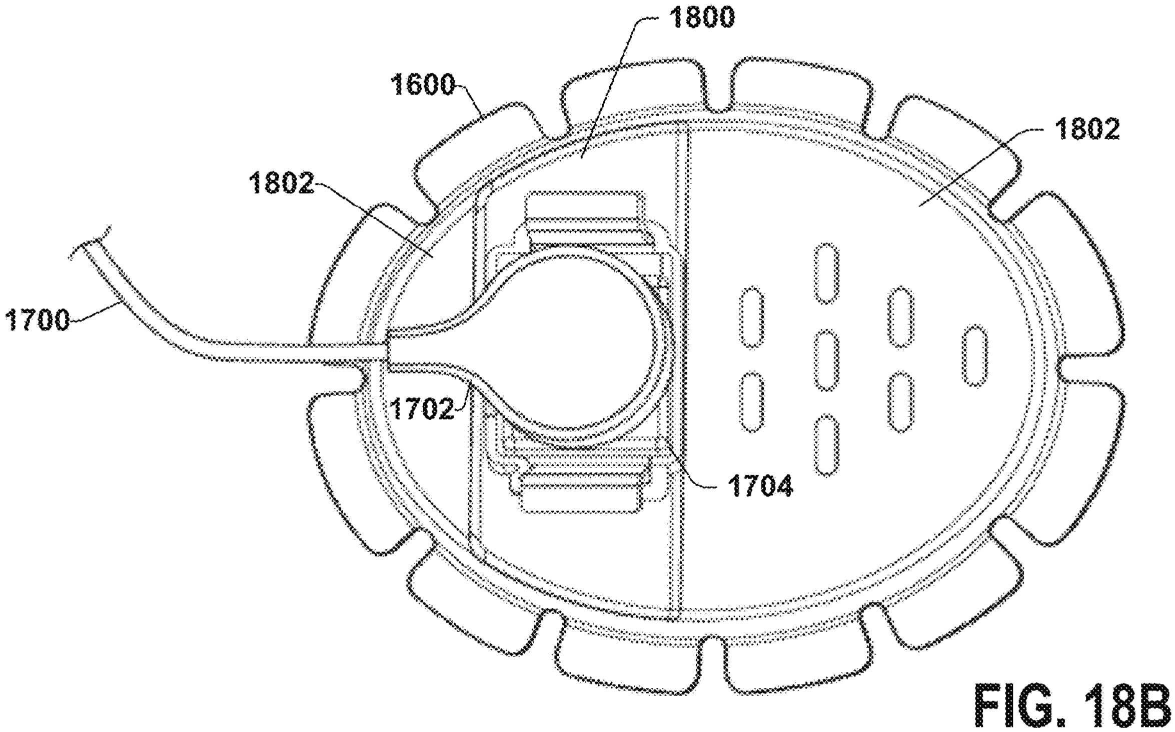

FIGS. 18A and 18B illustrate the cable with the magnetic head and a connector with the corresponding magnetic cradle with a protective cover configured such that a head of the cable remains outside of the protective cover, in accordance with the teachings of this disclosure.

Figure 19A:
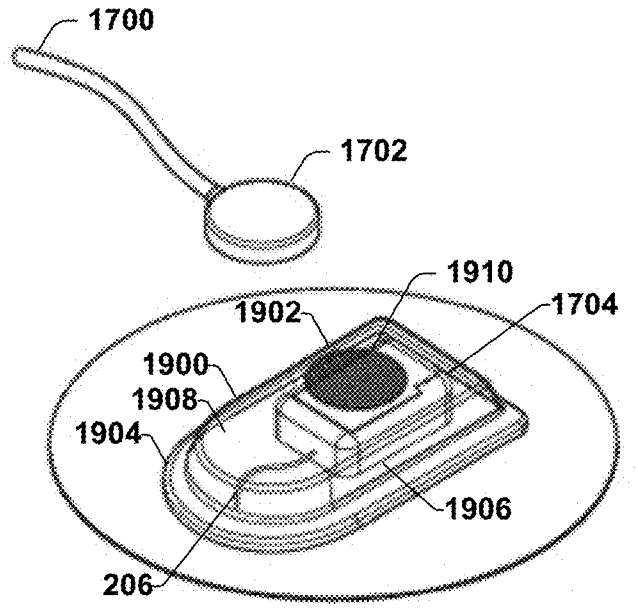
Figure 19B:
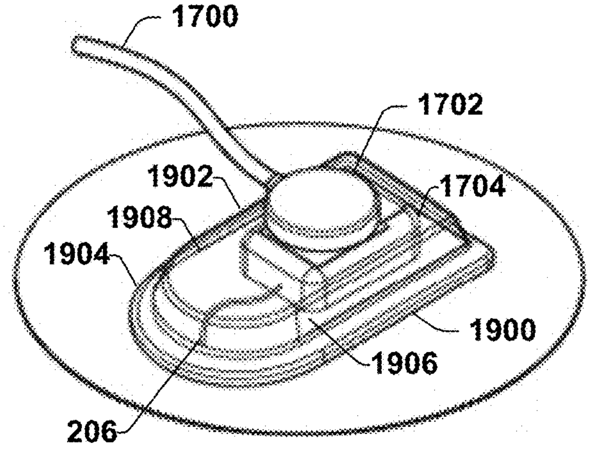
Figure 19C:
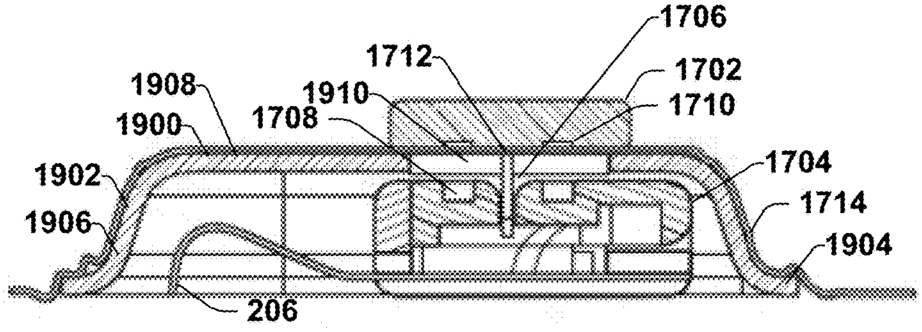

FIGS. 19A, 19B, and 19C illustrates a the cable with the magnetic head and a connector with the corresponding magnetic cradle with another example of the protective cover configured such that a head of the cable remains outside of the protective cover, in accordance with the teachings of this disclosure.

Figure 20A:
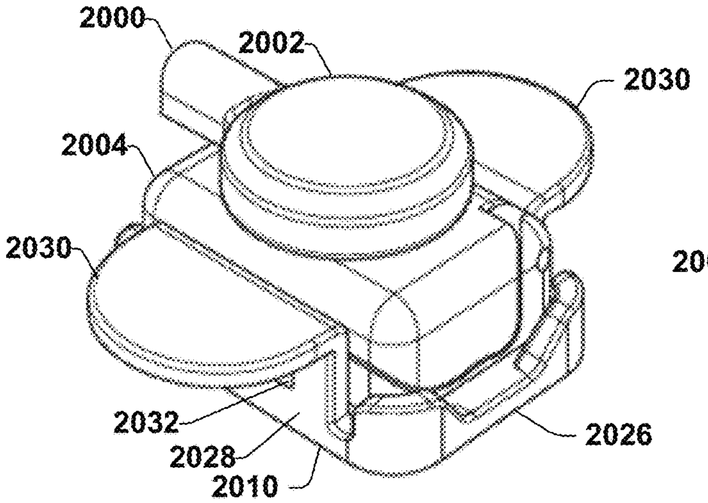
Figure 20B:
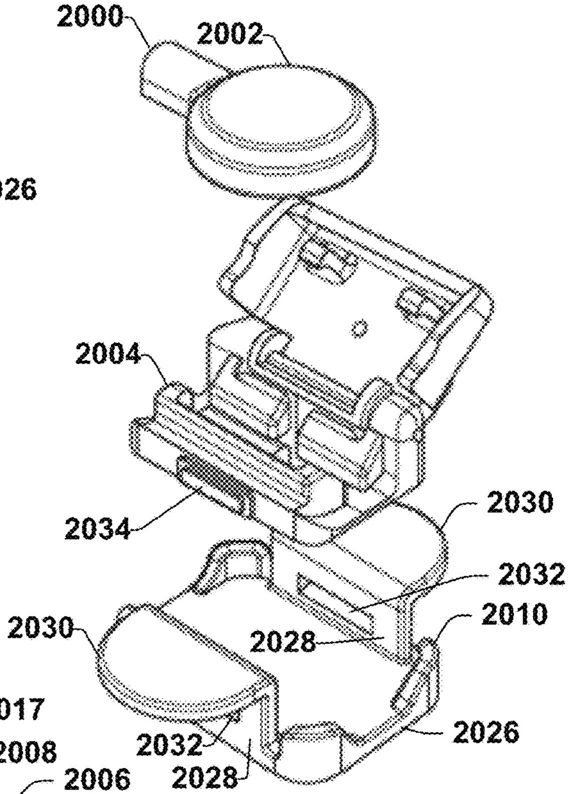
Figure 20C:
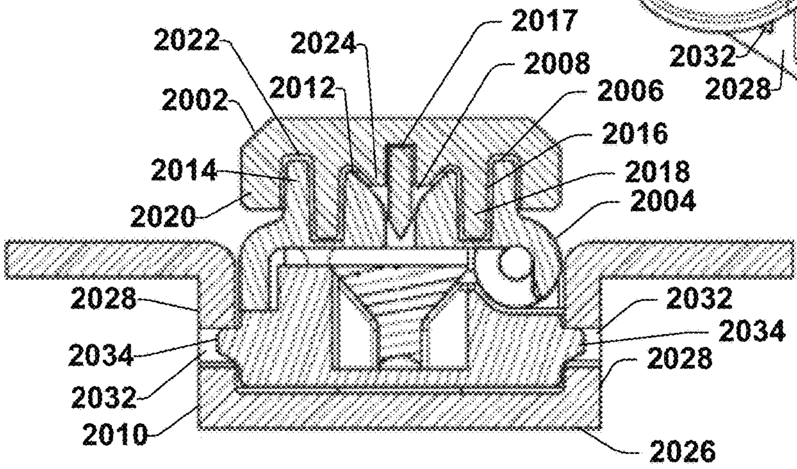

FIGS. 20A, 20B, and 20C illustrate a cable with an interlocking head and a connector with a corresponding magnetic cradle, in accordance with the teachings of this disclosure.

FIGS. 21A, 21B, 21C, and 21D illustrate a cable with a magnetic cradle head and a connector with a corresponding magnetic protrusion, in accordance with the teachings of this disclosure.

Figure 22A:
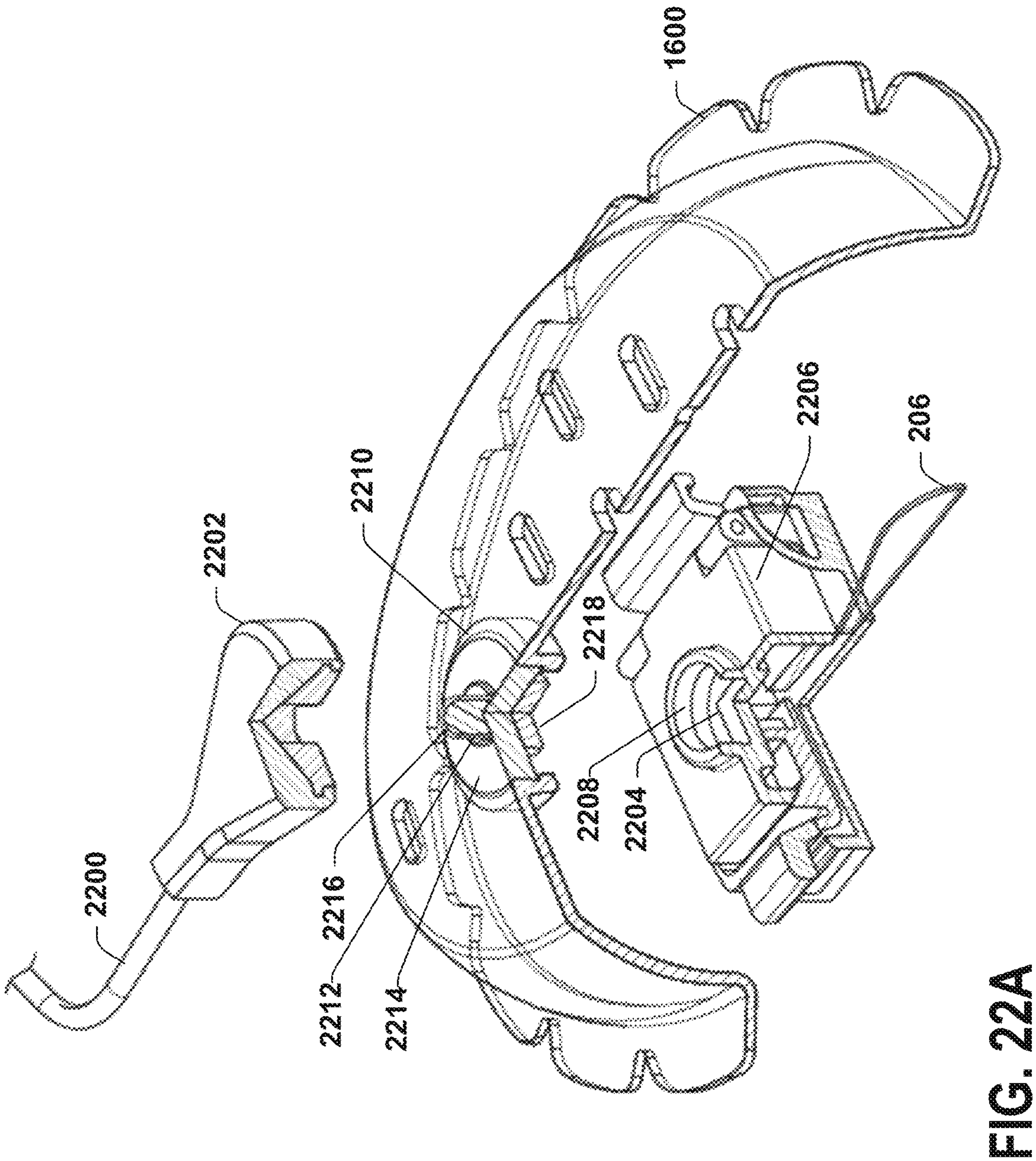
Figure 22B:
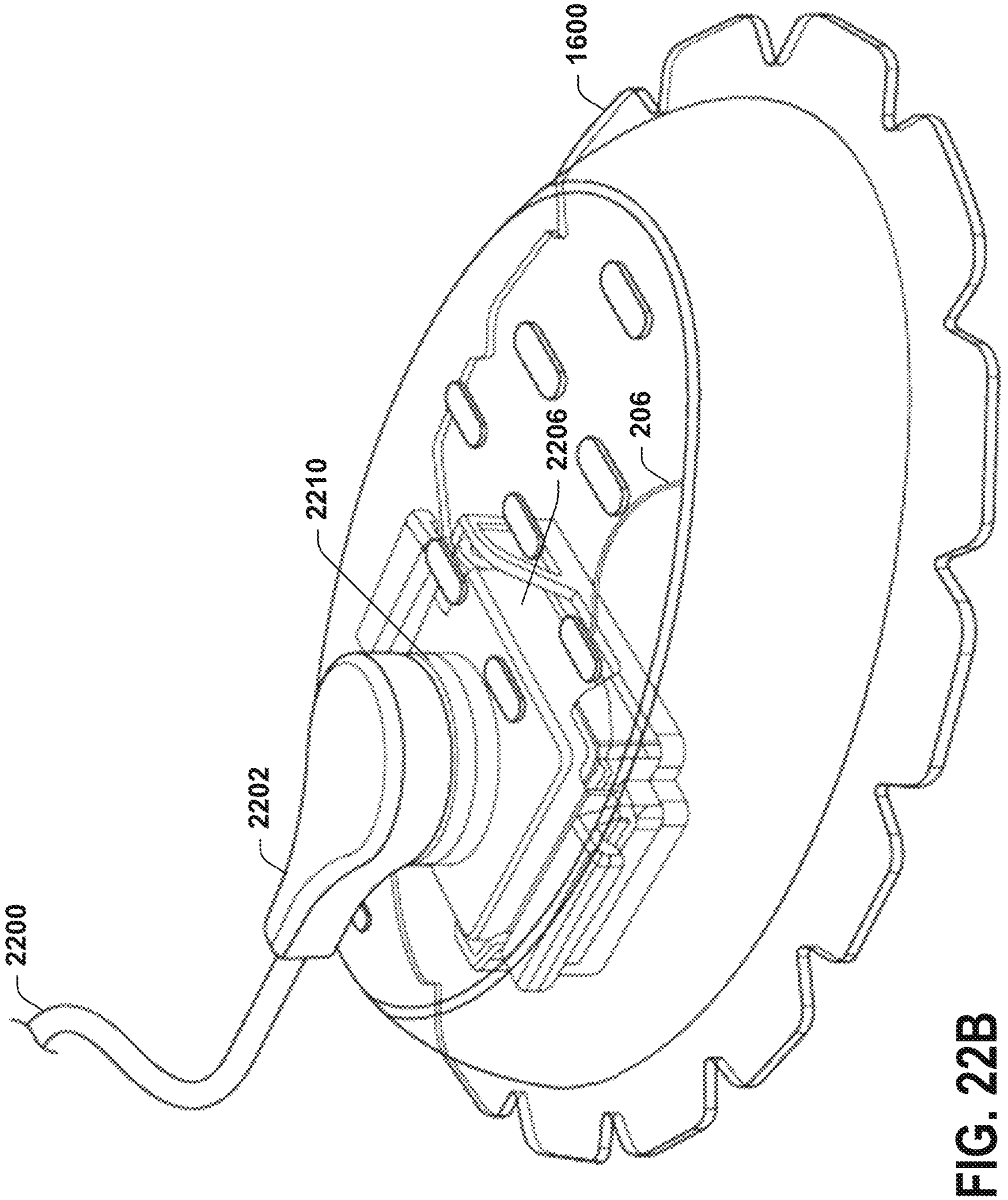

FIGS. 22A and 22B illustrate a protective cover configured to interface between the head of the cable and the cradle of the connector, in accordance with the teachings of this disclosure.

Figure 23A:
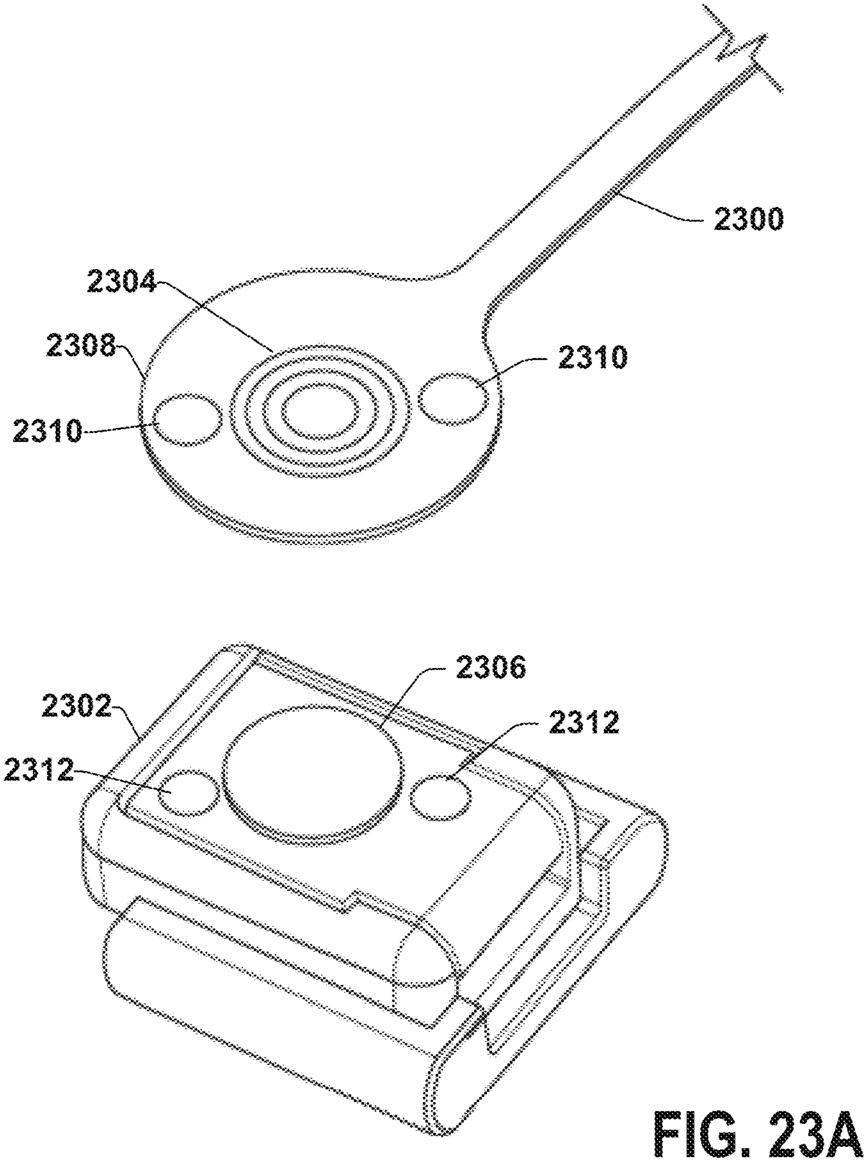
Figure 23B:
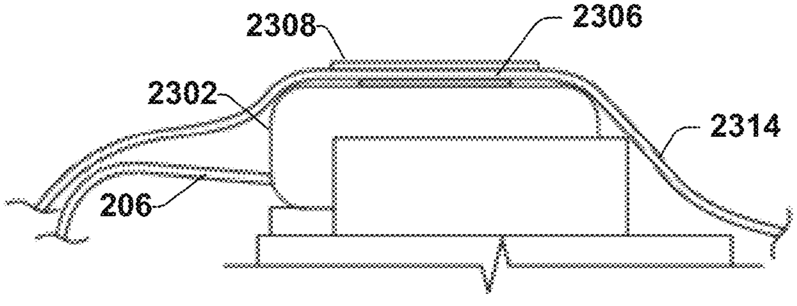

FIGS. 23A and 23B illustrate a cable and a connector with an inductive interface, in accordance with the teachings of this disclosure.

Figure 24:
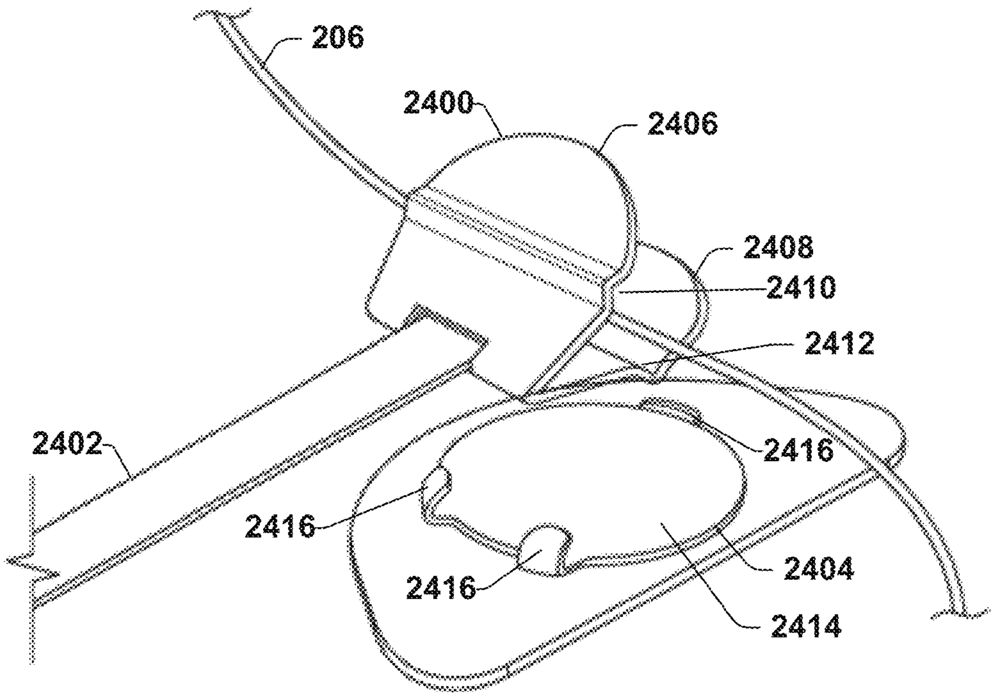

FIG. 24 illustrates an example thin connector, in accordance with the teachings of this disclosure.

Figure 25:
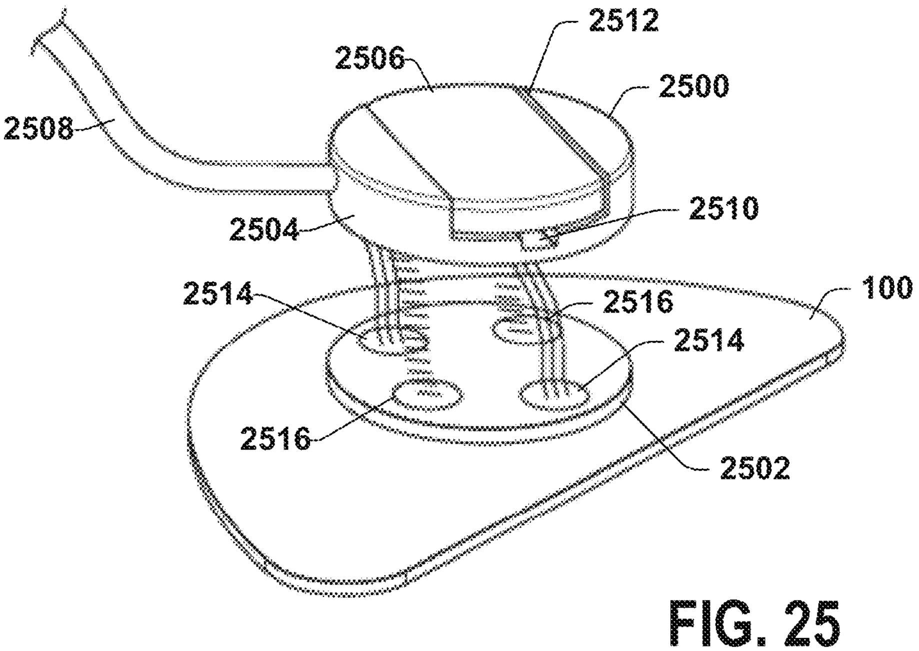

FIG. 25 illustrates an example polarized connector, in accordance with the teachings of this disclosure.

Figure 26A:
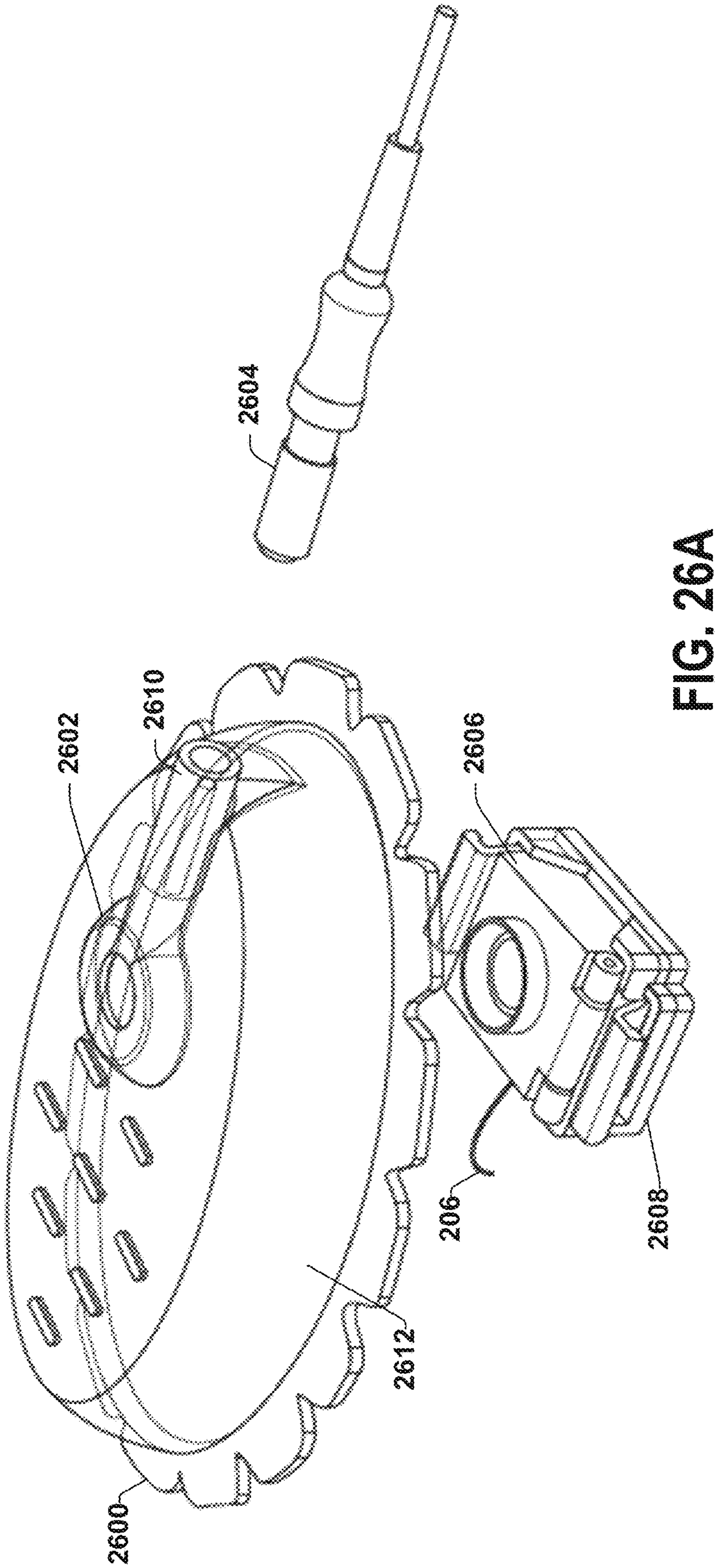
Figure 26B:
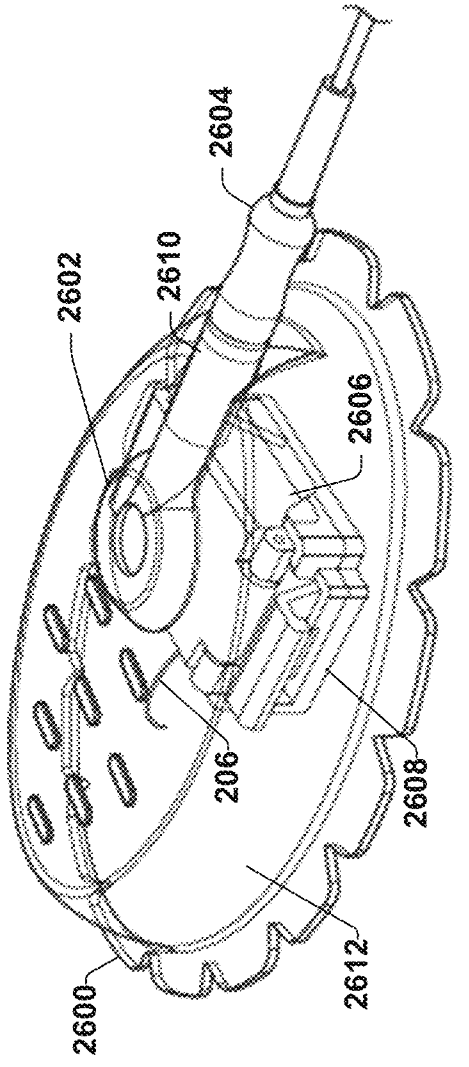
Figure 26C:
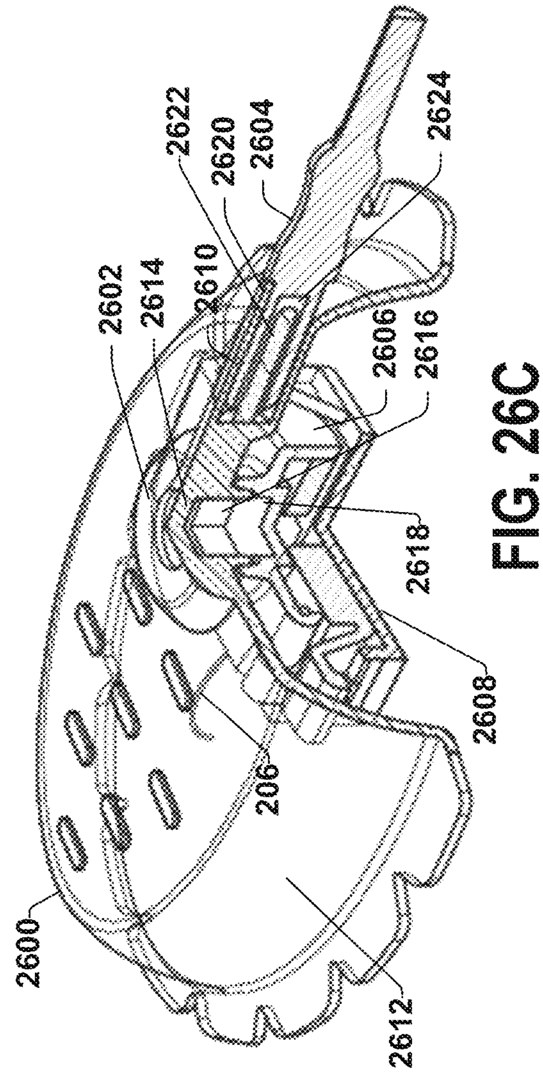

FIGS. 26A, 26B, and 26C illustrate example of the protective cover with an integrated cable head, in accordance with the teachings of this disclosure.

FIGS. 27A, 27B, 27C, 27D, 27E, 27F, 27G, and 27H illustrate an example stimulation lead connection system, in accordance with the teachings of this disclosure.

Figure 28A:
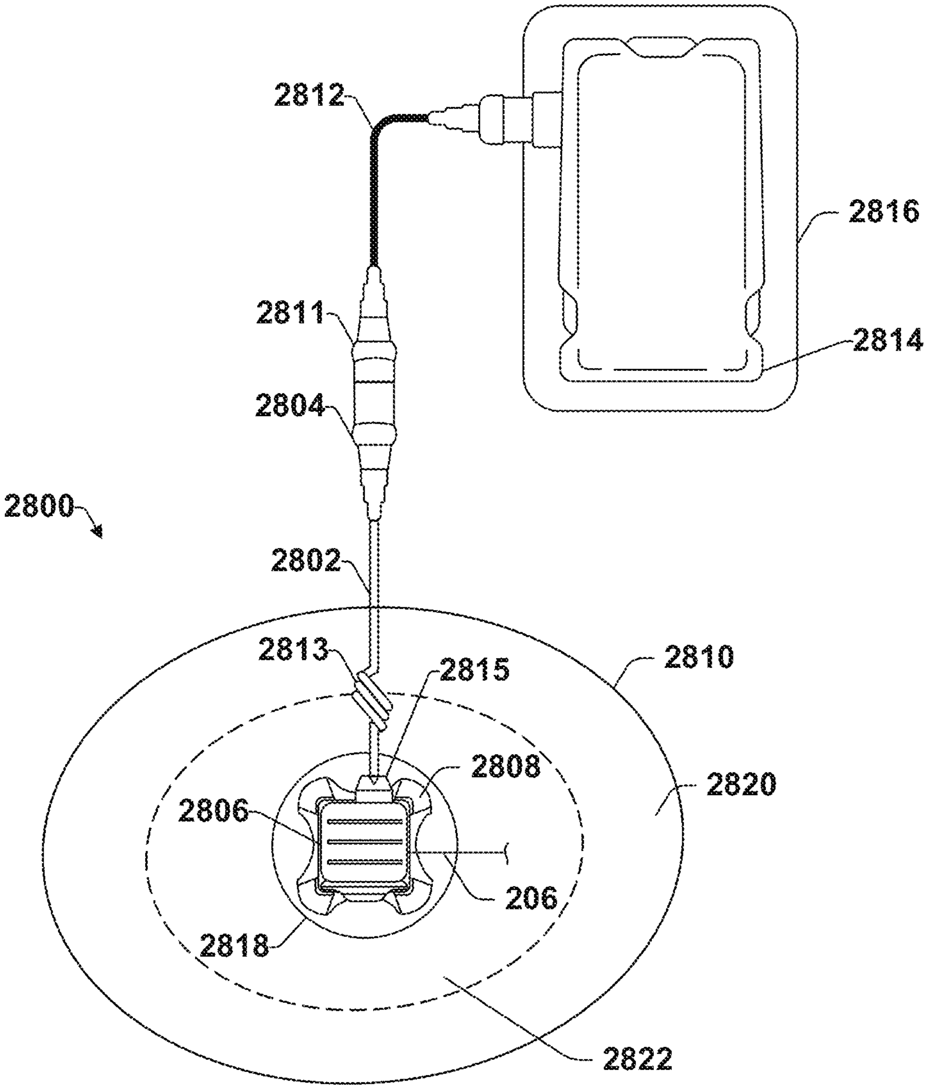
Figure 28B:
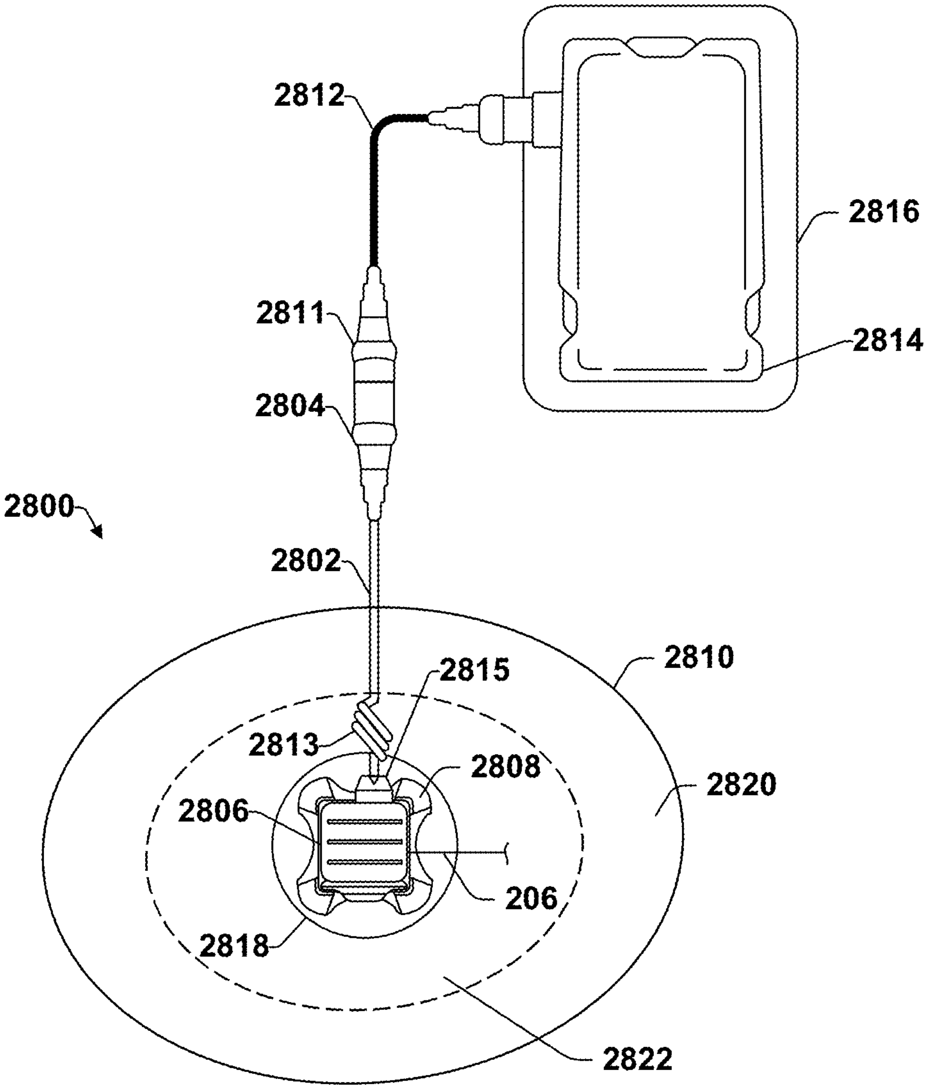

FIGS. 28A and 28B illustrates an example stimulation lead connection system, in accordance with the teachings of this disclosure.

FIGS. 29A, 29B, 29C, 29D, 29E, 29F, 29G, 29H, 29I, 29J, 29K, and 29L illustrate the example push lock connector and connector base of FIG. 28, in accordance with the teachings of this disclosure.

Figure 30A:
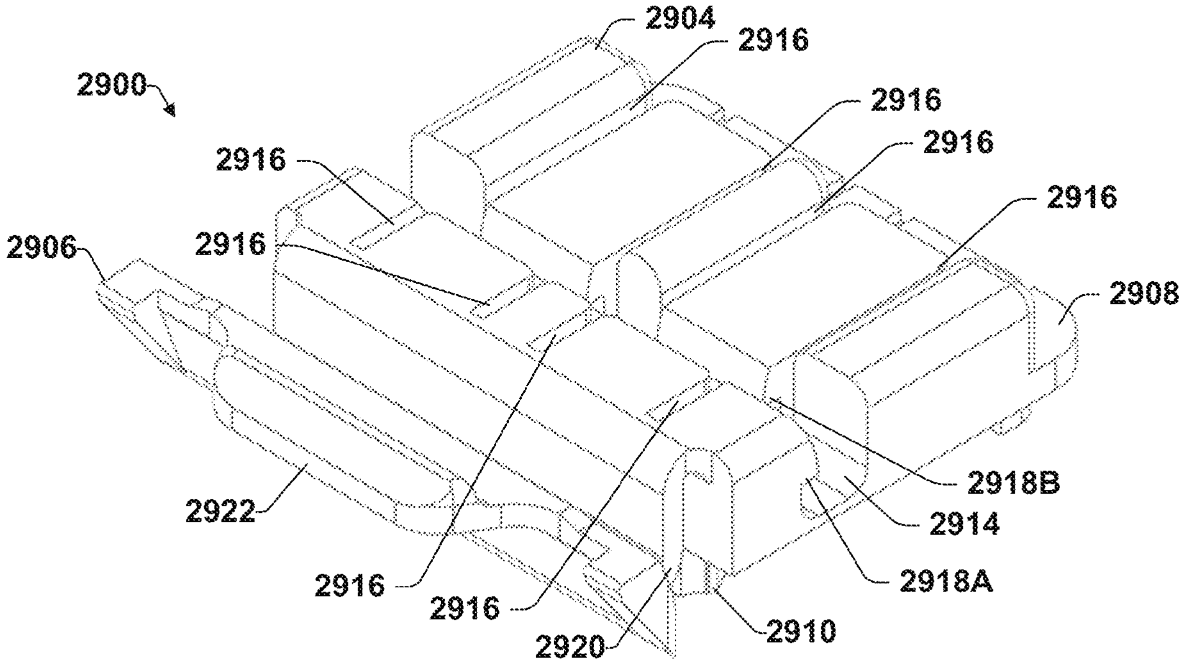
Figure 30B:
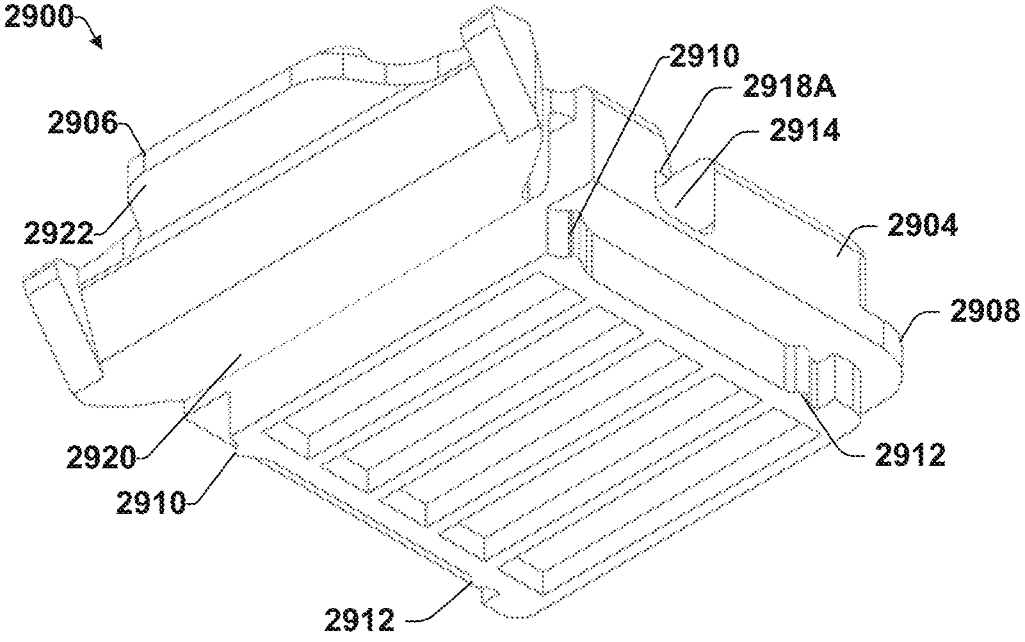
Figure 30C:
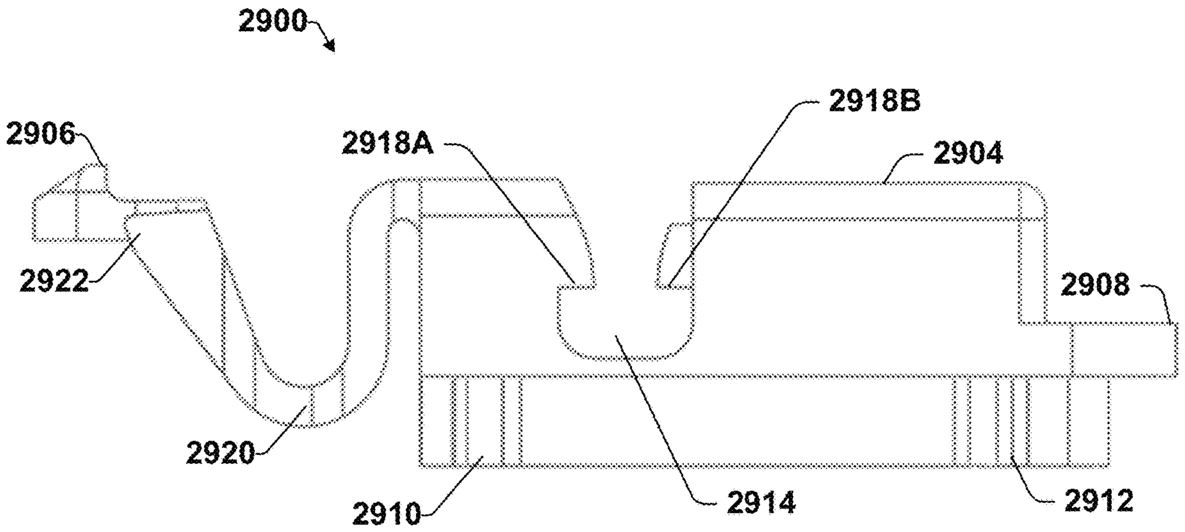

FIGS. 30A, 30B, and 30C illustrate an insert of the push lock connector of FIG. 28, in accordance with the teachings of this disclosure.

Figure 31:
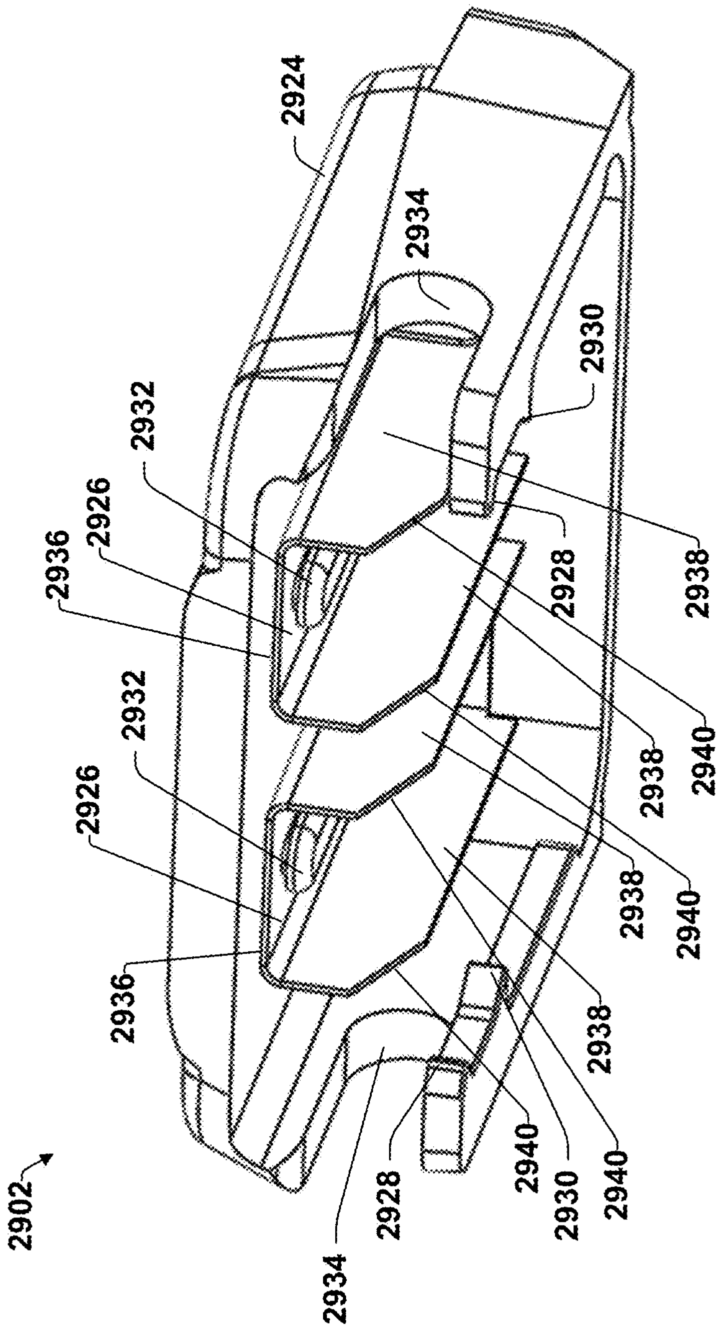

FIG. 31 illustrates a body of the push lock connector of FIG. 28, in accordance with the teachings of this disclosure.

FIGS. 32A, 32B, 32C, 32D, 32E, 32F, and 32G are conceptual diagrams of the blade of the insert interacting with a lead, in accordance with the teachings of this disclosure.

Figure 33:
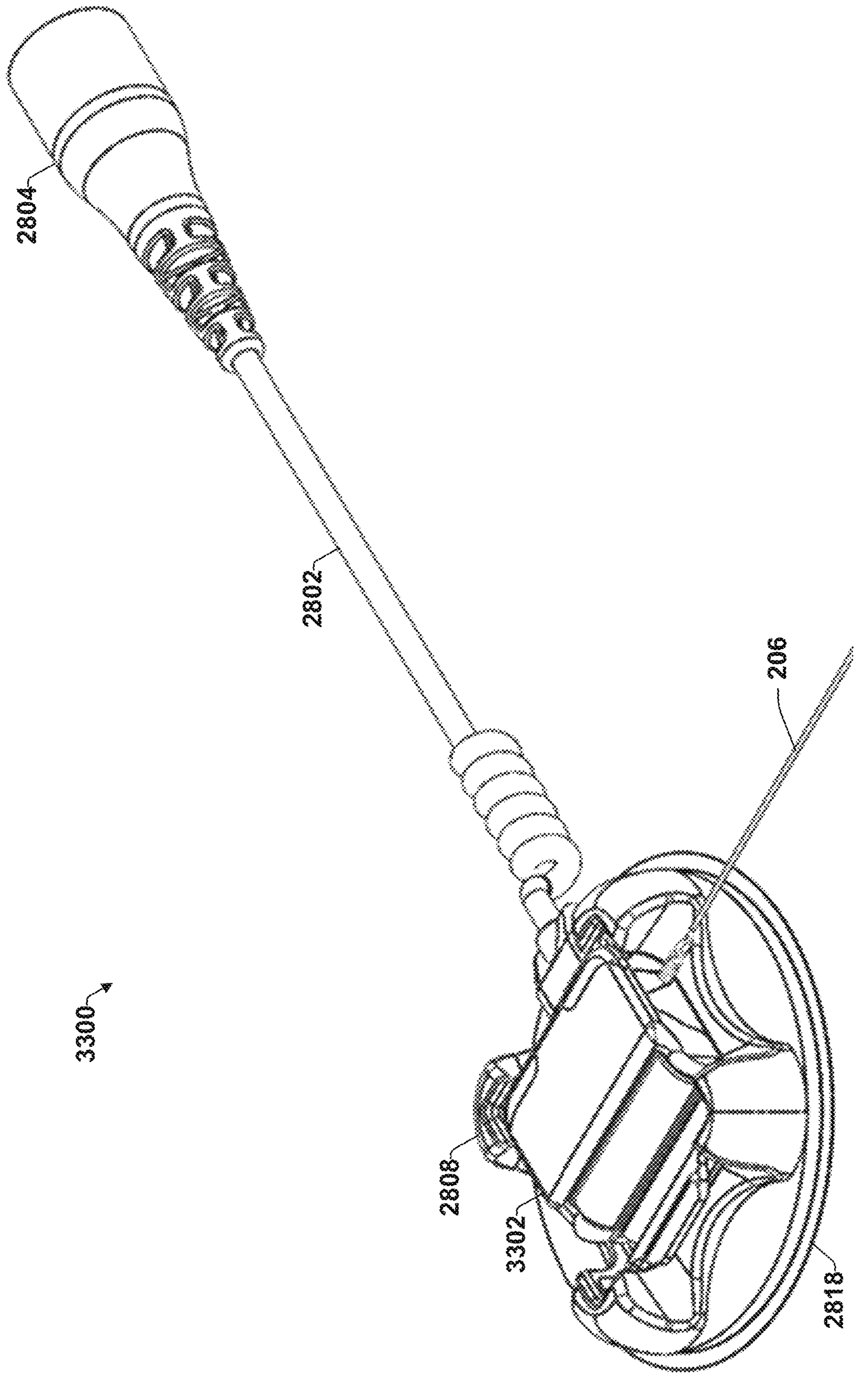

FIG. 33 illustrates example stimulation lead connection system with a clamshell connector, in accordance with the teachings of this disclosure.

FIGS. 34A, 34B, 34C, 34D, 34E, 34F, 34G, 34H, 34I, and 34J illustrate the clamshell connector of FIG. 33, in accordance with the teachings of this disclosure.

DESCRIPTION

As described below, the stimulation lead connection system may include a single deployment device or set of interrelated devices to incorporate implantation of a lead. The lead (also referred to as a micro-lead, fine-wire lead or simply electrode) may possess a generally small diameter in comparison to previous systems, with optimal sizes of less than 1.0 mm and, more preferably, less than 0.7 mm. Further, the electrode may have a generally coiled or helical structure, rather than a smooth cylinder. However, any suitable structure of the lead may be used. In some examples, the stimulation lead connection system may provide a single device that may locate a desired tissue region, test stimulation of the tissue region, position (or reposition) a testing signal, and/or deploy an electrode or lead. In some such examples, the stimulation lead connection system may enable repositioning of the device and lead within human or animal tissue without deploying the electrode or lead until its deployment is desired by the user (e.g., the clinician). This may provide a safe and easy to use connection system.

As used herein, the term “proximal” in the context of this application typically refers to the end of the electrode that is not inserted into the body and “distal” typically refers to the electrode end that is inserted into the body near the nerves. Depending upon the manufacture of the electrode structure, this proximal end may be wrapped in an insulating or protective coating or wrap. To the extent electrical connections must be made with the proximal end, the components at issue will allow for the removal of such coating(s)/wrap(s). The coating/wrap may include markings to serve as indicia of mobility that help to gauge whether the electrode has been repositioned or dislodged during system use, and particularly when outside of the oversight of a clinician.

As used herein, the terms inner sheath, introducer, introducing device, introducing needle, inner needle, inner probe, introducing member, and/or the like are utilized interchangeably unless context suggests otherwise or warrants a particular distinction among such terms. The terms outer sheath, delivery needle, outer needle, outer probe, outer member, and/or the like are utilized interchangeably unless context suggests otherwise or warrants a particular distinction among such terms.

The introducing device may enable a lead to be percutaneously placed a safe distance from a surgical site, which may increase safety, minimize risk to the anatomy that is the focus of the surgery, minimize the risk of infection, and minimize the potential impact of any infection should it occur. For example, the introducing device may enable placement of the lead to deliver stimulation to a nerve innervating a region, where the region may be painful or be anticipated to be painful due to a surgery (e.g., the device may enable placement of a lead to deliver stimulation to a femoral nerve, sciatic nerve, or lumbar plexus innervating a region, such as a knee which may be undergoing knee replacement surgery), and the device desirably enables the lead to be placed a safe distance (e.g., in the upper thigh, upper leg, or lower back) away from the surgical site (e.g., the knee) and/or outside of the surgical field.

There is a clinical need for a device that delivers therapeutic electrical stimulation (e.g. peripheral nerve stimulation (PNS)) to a nerve (e.g. peripheral nerve) innervating the region of pain to provide pain relief. The device may deliver stimulation to the nerve transmitting the pain signal or it may deliver stimulation to a nerve, which is not transmitting the pain signal, but when stimulation is delivered, a condition or symptom, such as pain, may be relieved or improved and/or function may be improved or restored. The device may deliver pain-relieving or function-restoring peripheral nerve stimulation in a variety of settings including chronic, acute, post-surgical, post-traumatic, and intermittent pain and/or loss of function, and other conditions (e.g., other types of pain and/or functional loss), as well as across a range of anatomical regions, including but not limited to limbs (e.g., arms, legs, etc.), extremities (e.g., hands, feet, fingers, toes, etc.), joints (e.g., hips, knees, shoulders, elbows, ankles, wrists, etc.), back, neck, head, face, and other regions.

The stimulation device may enable the delivery of electrical stimulation to provide pain relief or functional improvement immediately following surgery. The device may also improve function, strength, and range of motion following surgery, as well as accelerate post-op recovery. The device may enable delivery of stimulation before, during, and after surgery, as well as in scenarios not involving surgery, such as acute or chronic conditions within or outside of the context of surgery.

The connectors and the stimulation lead connection system, as described below, are useful for establishing electrical communication between one or more electrodes and a signal generator in stimulation devices. Non-limiting examples of such neurostimulation devices, as well as systems and methods of operation and use of such devices and systems, can be found in U.S. Pat. Nos. 6,845,271; 8,249,713; 8,463,383; 8,626,302; 8,788,046; 8,886,337; 8,954,153; 8,965,516; 9,248,289; 9,827,412; 9,855,427; and 9,895,530; all of which are incorporated by reference herein.

As a non-limiting example, an example stimulator may be able to provide at least the following parameters: ranges of intensities; range(s) of amplitudes (e.g., 0.2-20 mA, 0.1-30 mA, 0.1-40 mA, 0.1-50 mA); range(s) of pulse durations and/or pulse widths (e.g., of 10-100 μs, 10-200 μs, 10-100 μs, 10-300 μs, 1-1000 μs, 1-1500 μs, and/or 1-2000 μs; and ranges of frequency (e.g., of 1-20 Hz, 5-100 Hz, 1-100 Hz, 1-150 Hz, 1-200 Hz, 1-500 Hz, 1-1000 Hz, 1-1500 Hzm, 1-10,000 Hz, 1-100,000 Hz). The stimulator may be connected to software for wireless clinician programming of the therapy, software and hardware for a wireless patient controller, and firmware and hardware for a miniature body-mounted stimulator. This arrangement allows for the clinician and patient to view and adjust treatment parameters without having to interface with the stimulator directly. This can prevent a patient from having to remove clothing, etc., to reach the stimulator during use. In some examples, the stimulator may communicate via physical cables, wires, Bluetooth, or other wireless technologies. The present teachings are not limited to any particular configuration.

The patient controller may also provide a more extensive graphical user interface including a variety of other options (e.g., profiles specific to a time of day/type of pain/type of anticipated patient activity, access to information on pain management, means for communicating with a medical professional, etc.), thereby making it the primary means of initiating and altering the therapy. As with the stimulator, the controller communicates via physical wires/cables or wirelessly with the stimulator (or stimulators, if multiple stimulators are included in the system) and the optional programmer unit, described below. The controller may be relatively larger than the stimulator, although wireless connectivity would allow the user to carry the controller in clothing and/or generally at a convenient distance and location in comparison to the electrode and stimulator. The connections between the controller, stimulator, and introducer system may include any of those described herein (e.g., standard wired connections, wireless connections particularly between the controller and the stimulator, wired connections relying on quick release mechanisms, etc.).

The stimulator allows for adjustment of stimulation intensity by controlling stimulation amplitude and pulse duration, preferably with a single programmable parameter for intensity. Stimulation intensity itself may be determined by multiple parameters, including (but not limited to) stimulation amplitude and pulse duration. For example, stimulation intensity may be increased by increasing stimulation amplitude, pulse duration, or a combination of the two. Controlling multiple parameters such as stimulation amplitude and pulse duration using a single parameter may reduce the complexity of the procedure to program stimulation parameters by reducing the number of parameters that can be changed from 2 or more to 1. As a non-limiting example, the minimum of the stimulation intensity parameter (e.g., 0) may set the stimulation amplitude and pulse duration to their lowest values (e.g., 0.2 mA and 10 microseconds). As another example, increasing the stimulation intensity parameter may change the stimulation amplitude, the pulse duration, or both.

In some examples, a lead connector of the stimulation connection system may enable easy one-handed insertion and coupling of the lead to the system while remaining mechanically and electrically secure and prevents the patient from decoupling the lead (or electrode) intentionally or unintentionally. The lead may be coupled to the lead connector electrically and mechanically. The mechanism by which the lead may be coupled mechanically to the lead connector may be separate or the same as the mechanism by which the lead is coupled electrically to the lead connector. As described below, the user may couple the lead to the lead connector using one or more of a variety of components such as, a knob, button, switch, dial, or lever.

The lead connector may be decoupled from the lead, and may allow the lead to be reconnected to the lead connector at a different point along the lead (e.g., closer to or farther away from the stimulating portion of the lead or electrode). In a non-limiting example, the lead connector may include a lock to prevent the patient from disconnecting the lead. The lock may be opened using, for example (but not limited to), a key, a tool (e.g., screw driver, wrench, or torque wrench), a code (e.g., combination) or without a tool. As another example, the lead connector may minimize or eliminate damages or changes to the lead's structure, enabling the lead to remain sufficiently intact to generally reduce the risk of the lead fracturing or breaking and enable current flow through the entire lead. In another example, a lead connector may be attached to the lead prior to or after insertion of an introducer system, enabling stimulation through the lead tip during the lead placement procedure. In some examples, the connector may be attached to the lead by dropping the lead into a slot or hole on the block and closing a flap which implements one or more insulation displacement connection(s) (e.g., cutting through the insulative material aside to form a connection with the conductive lead wire). This lead connector may, for example, improve the speed and ease of lead connection because it can be attached without the use of tools (e.g., no wire cutters, scissors, and screwdrivers). For example, in such an example, the lead may be placed into a slot in a lead connector block and secured using a lockable, reversible one-handed mechanism to displace the insulation on the lead body. The insulation displacement mechanism(s) (sometimes referred to as a "blade(s)") inside the lead connector may also cut the lead distal to the electrical connection. Once the connection has been made and the excess lead is trimmed, a lock (e.g., sliding, twisting, button press) may ensure that the flap on the block cannot be reopened accidentally. This inhibits loss of connection between the lead connector and lead, which would result in loss of therapeutic benefit. The lead connector may incorporate and/or mate with a cable and/or cables (e.g., lead or plug to the stimulator) to complete the circuit from the stimulator to the lead tip electrode.

In some examples, the connection between the lead connector and the cable may be magnetic. In such examples, the shape of the lead connector and the corresponding head of the cable are configured to prevent improper alignment of the lead connector (e.g., lead connectors that only fit together in one orientation). The magnetic connection may be used for both temporary and permanent stimulation delivery (e.g., during lead placement procedure or during patient's home use of the therapy). After obtaining proper lead placement location, the lead connector block may be removed and replaced following removal of the introducer system needle(s) and sheath(s). In some examples, the connection may be deactivated by pressing or sliding open the slot that contains the lead. In such examples, the lead connector block may be removed or cut off prior to removal of the introducer and then quickly re-attached to a more proximal location on the lead. Following removal of the introducer, the lead may be placed in the slot and connected with a one-touch mechanism (e.g., pressing, sliding) and then the lead connector may be attached to the stimulator cable.

The magnetic connection may act as a quick-release connection that prevents or inhibits accidental lead (or electrode) dislodgement due to a pulled lead and/or lead. Instead of transferring force to the lead exit site and lead, any forces on the lead is interrupted due to the breaking of the magnetic connection between the cable and lead connector. In some examples, a non-disengageable connection may be made by locking the connector and cable together using a press button lock (or any other suitable lock). In addition to mating with the lead connector block, in some examples, the magnetic cable connector for the stimulator may also mate with an identical version of the lead connector block, which is connected to the test stimulator via a cable. In some examples, the magnetic cable connector originating from the stimulator may be bifurcated to connect with multiple lead connectors (e.g., to enable stimulation of two leads with one stimulator).

As described below, the stimulation lead connection systems promotes a shorter duration of the lead placement and stimulation testing procedures. The system also limits the number of percutaneous insertions required, decreases risk to the patient, enables efficient positioning and re-positioning of the lead for stimulation testing and lead deployment, enables clinicians to position and deploy the lead correctly and optimally with minimal or no additional training, and decreases the time required to form electrical connections for testing. As a result, the therapy can be delivered to patients by clinicians in settings/scenarios that were previously burdensome, not practical and/or not possible (e.g., to treat pre-operative, pen-operative, and/or post-operative pain).

A. Stimulation of Peripheral Nerves

The following describes an example peripheral nerve system and method that incorporates features of the present teachings. The system and method may identify a region where there is a local manifestation of pain. The region of pain may comprise any appropriate portion of the body, e.g., tissue, skin, bone, a joint, or muscle. The system and method may identify one or more spinal nerves located distant from the region where pain is manifested, through which neural impulses comprising the pain pass. A given spinal nerve that is identified may comprise a nerve trunk located in a nerve plexus, or a division and/or a cord of a nerve trunk, or a nerve branch, or a nerve plexus provided that it is upstream or cranial of where the nerve innervates the region affected by the pain. The given spinal nerve may be identified by medical professionals using textbooks of human anatomy along with their knowledge of the site and the nature of the pain or injury, as well as by physical manipulation and/or imaging, e.g., by ultrasound, fluoroscopy, or X-ray examination, of the region where pain is manifested. A desired criteria of the selection may include identifying the location of tissue in a therapeutically effective distance from the nerve or passage, which tissue may be accessed by placement of one or more stimulation electrodes, aided if necessary by ultrasonic or electro-location techniques. A therapeutically effective distance may be defined to mean the placement of a lead either in contact with, or more preferably adjacent to a nerve. The nerve identified may comprise a targeted peripheral nerve. The tissue identified may comprise the "targeted tissue."

The electrode(s) of the electrical stimulation device (e.g., the electrical stimulation device 2814) may be percutaneously inserted using percutaneous lead(s) (e.g., one or more of the lead 206). The system and method may place the one or more leads with its electrode(s) in the targeted tissue in electrical proximity to but spaced away from the targeted peripheral nerve. The system and method may apply electrical stimulation through the one or more stimulation electrodes to electrically activate or recruit the targeted peripheral nerve that conveys the neural impulses comprising the pain to the spinal column.

The system and method may apply electrical stimulation to peripheral nerves throughout the body. By way of a non-limiting example, the peripheral nerves may comprise one or more spinal nerves in the brachial plexus, to treat pain in the shoulder(s), arm(s) and hand(s); and/or one or more spinal nerves in the lumbar plexus, to treat pain in the back, thigh(s), knee(s), and calve(s); and/or one or more spinal nerves in the sacral plexus, to treat pain in the thigh(s), calve(s), and feet; and/or one or more spinal nerves in the cervical plexus, to treat pain in the shoulder(s).

For example, if the pinky finger is the location of pain following an injury (e.g., limb joint replacement surgery), the system and method may identify and stimulate the ulnar nerve at a location upstream or cranial of where the nerve innervates the muscle or skin of the pinky finger, e.g., in the palm of the hand, forearm, and/or upper arm. If electrical stimulation activates the target peripheral nerve sufficiently at the correct intensity, then the patient will feel a comfortable tingling sensation called paresthesia in the same region as their pain, which overlaps with the region of pain and/or otherwise reduce pain.

It is to be appreciated that the sensation could be described with other words such as buzzing, thumping, etc. Evoking paresthesia in the region of pain confirms correct lead placement and indicates stimulus intensity is sufficient to reduce pain. Inserting a lead percutaneously may allow the lead to be placed quickly and easily. Placing the lead in a peripheral location, e.g., tissue, where it is less likely to be dislodged, may address lead migration problems of spinal cord stimulation that may otherwise cause decreased paresthesia coverage, decreased pain relief, and the need for frequent patient visits for reprogramming.

Placing the lead percutaneously in tissue in electrical proximity to but spaced away from the targeted peripheral nerve may also minimize complications related to lead placement and movement. In a percutaneous system, an electrode lead, such as a coiled fine wire electrode lead may be used because it is minimally-invasive and well suited for placement in proximity to a peripheral nerve. The lead may be sized and configured to withstand mechanical forces and resist migration during long-term use, particularly in flexible regions of the body, such as the shoulder, elbow, and knee.

The electrode lead may include a fine wire electrode, paddle electrode, intramuscular electrode, or general-purpose electrode, inserted via a needle introducer or surgically implanted in proximity of a targeted peripheral nerve. Once proper placement is confirmed, the needle introducer may be withdrawn, leaving the electrode in place. Stimulation may also be applied through a penetrating electrode, such as an electrode array comprised of any number (i.e., one or more) of needle-like electrodes that may be inserted into the target site. In both cases, the lead may be placed using a needle-like introducer, allowing the lead/electrode placement to be minimally invasive. An example lead may include a thin, flexible component made of a metal and/or polymer material. By "thin," it is contemplated that the lead may not be greater than 1 mm and/or preferably not greater than about 0.75 mm (0.030 inch) in diameter but of sufficient diameter to remain intact (e.g., not fracture) when surrounding tissue compresses and/or flexes, and/or when being removed. However, the present teachings are not limited to such dimensions. Any appropriate lead may be utilized. The lead(s) may have a range of diameters and still be considered small or appropriate (e.g., $<0.5$ mm, $<0.6$ mm, $<0.7$ mm, $<0.8$ mm, $<0.9$ mm, $<1.0$ mm, $<2$ mm, and/or $<3$ mm) and the connector and other aspects of the invention are designed to accommodate and function correctly with one or more lead sizes and/or range(s) of sizes. The lead may also include one or more coiled metal wires within an open or flexible elastomer core. The wire may be insulated, e.g., with a biocompatible polymer film or coating, such as polyfluorocarbon, polyimide, or parylene as non-limiting examples. The lead may be electrically insulated everywhere except at one (monopolar), or two (bipolar), or three (tripolar), for example, conduction locations near its distal tip. Each of the conduction locations may be connected to one or more conductor(s) or conductive wire(s), strand(s), filament(s) and/or cable(s) that may run the length of the lead and lead extension or a portion thereof. The conductor(s) may provide electrical continuity from the conduction location through the lead to an external pulse generator or stimulator.

The conduction location or electrode may include a de-insulated area of an otherwise insulated conductor(s) or conductive wire(s), strand(s), filament(s) and/or cable(s) that may run the length of an entirely insulated electrode or a portion thereof. The de-insulated conduction region of the conductor(s) may be formed differently, e.g., it may be wound with a different pitch, or wound with a larger or smaller diameter, or molded to a different dimension. The conduction location or the electrode may include a separate material (e.g., metal or a conductive polymer) exposed to the body tissue to which the conductor(s) of the wire is bonded.

The lead may be provided in a sterile package, and may be pre-loaded in or on the introducer needle or other needles used during lead placement. Alternatively, the lead may be introduced via the same needle that is used to inject anesthetic or analgesics during peripheral nerve blocks, which are often used post-limb joint replacement surgery, or may be provided separately as an independent component or components. The package may take various forms and the arrangement and contents of the package may be as appropriate related to the use thereof including but not limited to the lead, introducer system, relevant cabling, external pulse generator, and/or relevant bandage(s) and/or cover(s). The package may include a sterile, wrapped assembly. The package may include an interior tray made from any appropriate material, e.g., from die cut cardboard, plastic sheet, or thermo-formed plastic material, which may hold the contents. The package may also desirably include instructions for use regarding using the contents of the package to carry out the lead location and placement procedures, as will be described in greater detail below.

The lead may possess mechanical properties in terms of flexibility and fatigue life that provide an operating life free of mechanical and/or electrical failure, taking into account the dynamics of the surrounding tissue (i.e., stretching, bending, pushing, pulling, crushing, etc.). The material of the electrode may discourage the in-growth of connective tissue along its length or an applicable portion thereof, so as not to inhibit its withdrawal at the end of its use. However, it may be desirable to encourage the in-growth of connective tissue at the distal tip of the electrode, to enhance its anchoring in tissue.

Examples of the lead may include a minimally invasive coiled fine wire lead and electrode. The electrode may also include, at its distal tip, an anchoring element. In some examples, the anchoring element may take the form of a single and/or multiple barb(s) or bend(s).

The anchoring element may be sized and configured so that, when in contact with tissue, it takes purchase in tissue, to resist dislodgement or migration of the electrode out of the correct location in the surrounding tissue. The anchoring element may be prevented from fully engaging body tissue until after the electrode has been correctly located and deployed.

In some examples, the electrode lead may also include, at or near its distal tip or region, one or more anchoring element(s). The anchoring element may take the form of an array of shovel-like paddles or scallops proximal to the proximal-most electrode (although a paddle or paddles may also be proximal to the distal most electrode, or may also be distal to the distal most electrode). The paddles as shown may be sized and configured so they will not cut or score the surrounding tissue. The anchoring element(s) may be sized and configured so that, when in contact with tissue, it takes purchase in tissue, to resist dislodgement or migration of the electrode out of the correct location in the surrounding tissue (e.g., muscle). The anchoring element may be prevented from fully engaging body tissue until after the electrode has been deployed. The electrode may not be deployed until after it has been correctly located during the implantation (lead placement) process, as previously described. In addition, the lead may include one or more ink markings, to aid the clinician in its proper placement. Alternatively or additionally, the anchoring element may be any of the lead anchors described below, such as a folding lead anchor, a snapping lead anchor, an adhesive-based lead anchor and/or the dual purpose lead anchor, etc.

Alternatively, or in combination, stimulation may be applied through any type of nerve cuff (spiral, helical, cylindrical, book, flat interface nerve electrode (FINE), slowly closing FINE, etc.), paddle (or paddle-style) electrode lead, cylindrical electrode lead, echogenic needle (i.e., visible under ultrasound) and/or other lead that is surgically or percutaneously placed within tissue at the target site.

The lead may exit through the skin and connect with one or more external stimulators. Further, the lead may be connected as needed to internal and external coils for RF (Radio Frequency) wireless telemetry communications or an inductively coupled telemetry to control the implanted pulse generator. The implanted pulse generator may be located some distance (remote) from the electrode, or an implanted pulse generator may be integrated with an electrode(s) (not shown), eliminating the need to route the lead subcutaneously to the implanted pulse generator.

The introducer may be insulated along the length of the shaft, except for those areas that correspond with the exposed conduction surfaces of the electrode housed inside the introducer. These surfaces on the outside of the introducer may be electrically isolated from each other and from the shaft of the introducer. These surfaces may be electrically connected to a connector at the end of the introducer body. This may allow connection to an external stimulator during the implantation process. Applying stimulating current through the outside surfaces of the introducer may provide a close approximation to the response that the electrode will provide when it is deployed at the current location of the introducer.

The introducer may be sized and configured to be bent by hand prior to its insertion through the skin. This may allow the physician to place the lead in a location that is not in an unobstructed straight line with the insertion site. The construction and materials of the introducer may allow bending without interfering with the deployment of the lead and withdrawal of the introducer, leaving the lead in the tissue.

Described herein are systems, apparatuses, and methods that may conveniently provide and/or facilitate a single deployment device to incorporate implantation of a lead. The lead (also referred to as a micro-lead, fine-wire lead and/or simply electrode) may possess a generally small diameter in comparison to previous systems, with optimal sizes of less than 1.0 mm and, more preferably, less than 0.7 mm. Further, the electrode may have a generally coiled and/or helical structure, rather than a smooth cylinder. However, the present teachings are not limited to this structure of lead. Any appropriate configuration may be utilized without departing from the present teachings. Examples described herein may conveniently provide a single device that may locate a desired tissue region, test stimulation of the tissue region, position (or reposition) a testing signal, and/or deploy an electrode or lead. The examples describe herein may enable repositioning of the device and/or lead within human or animal tissue while avoiding deploying the electrode or lead until its deployment is desired by the user (e.g., the clinician). Examples described herein may provide an easy to use and safe systems, apparatuses, and/or methods.

The introducing device may enable a lead to be percutaneously placed a safe distance from a surgical site, which may increase safety, minimize risk to the anatomy that is the focus of the surgery, minimize the risk of infection, and/or minimize the potential impact of any infection should it occur. As a non-limiting example, the device may enable placement of the lead to deliver stimulation to a nerve innervating a region, where the region may be painful or be anticipated to be painful due to a surgery (e.g., the device may enable placement of a lead to deliver stimulation to a femoral nerve, sciatic nerve, and/or lumbar plexus innervating a region, such as a knee which may be undergoing knee replacement surgery), and/or the device desirably enables the lead to be placed a safe distance (e.g., in the upper thigh, upper leg, and/or lower back) away from the surgical site (e.g., the knee) and/or outside of the surgical field.

The introducing device may enable a target nerve to be identified prior to lead placement and/or prior to lead deployment as part of a non-surgical procedure.

There is a clinical need for a device that delivers therapeutic electrical stimulation (e.g. peripheral nerve stimulation (PNS)) to a nerve (e.g. peripheral nerve) innervating the region of pain to provide pain relief. The device may deliver stimulation to the nerve transmitting the pain signal and/or it may deliver stimulation to a nerve, which is not transmitting the pain signal, but when stimulation is delivered, a condition or symptom, such as pain, may be relieved or improved and/or function may be improved or restored. The device may deliver pain-relieving or function-restoring peripheral nerve stimulation in a variety of settings including chronic, acute, post-surgical, post-traumatic, and intermittent pain and/or loss of function, and other conditions (e.g., other types of pain and/or functional loss), as well as across a range of anatomical regions, including but not limited to limbs (e.g., arms, legs, etc.), extremities (e.g., hands, feet, fingers, toes, etc.), joints (e.g., hips, knees, shoulders, elbows, ankles, wrists, etc.), back, neck, head, face, and/or other regions.

The device may enable the delivery of electrical stimulation to provide pain relief or functional improvement immediately following surgery. The device may also improve function, strength, and/or range of motion following surgery, as well as accelerate post-op recovery. The device may enable delivery of stimulation before, during, and/or after surgery, as well as in scenarios not involving surgery, such as acute and/or chronic conditions within or outside of the context of surgery.

Additional examples of a percutaneous stimulation system according to the present teachings are described below. In the descriptions, all of the details and components may not be fully described or shown. Rather, the main features or components are described and, in some instances, differences with the above-described examples may be pointed out. Moreover, it should be appreciated that these additional examples may include elements or components utilized that are not shown or described. Thus, the descriptions of these additional examples are not all-inclusive nor exclusive. Moreover, it should be appreciated that the features, components, elements and functionalities of the various examples may be combined or altered to achieve a desired percutaneous stimulation system without departing from the spirit and scope of the present invention.

The system and methods described below may reduce lead placement and/or testing procedure duration when placing one or more self-anchoring leads. Specifically, placement, connection, disconnection, reconnection, and/or testing times are reduced in comparison to prior art systems by reducing the challenges of making electrical and mechanical connections with the percutaneous lead and/or other system components.

As described below, the systems and methods facilitate the use of the lead for testing, a non-limiting example being a connector which can electrically connect the proximal end of the lead to an external stimulator via a wire quickly and effectively in a useful way (e.g., strong/stable mechanical and/or electrical connection) and which can reduce the duration of the procedure. Being able to easily remove the connector also can reduces procedure time, as upon lead deployment in the prior art, the introducer system must be withdrawn over the lead, and a connector would stop this from happening and would need to be removed as the introducer needle/sheath cannot be withdrawn over it without first disconnecting the lead. Although a simple connector (e.g., a commercial alligator clip) could be used, such a connector can be difficult to use in an operative setting with an extremely small diameter coiled lead. Clinicians and/or staff may have difficulty connecting the tiny end of the wire to a typical/mechanical electrical connector. A non-limiting example that addresses these issues is a custom connector consisting of a channel which the end of the lead can easily be inserted into. The channel holds and/or guides the lead wire into the connector area, where teeth, loops, and/or surfaces which may be spring-loaded can be manipulated by the user via levers or buttons to clamp onto and create an electrical connection with the lead. This connector could have a wire and plug attached with enables connection with an external stimulator.

In some examples, the lead connector may enable easy one-handed insertion and coupling of the lead to the system while remaining mechanically and electrically secure and/or prevents the patient from decoupling the lead (and/or electrode) intentionally or unintentionally.

The lead may be coupled to the lead connector electrically and/or mechanically. The mechanism by which the lead may be coupled mechanically to the lead connector may be separate or the same as the mechanism by which the lead is coupled electrically to the lead connector. The user may couple the lead to the lead connector using a component including, but not limited to, a knob, button, switch, or dial.

The lead connector may be decoupled from the lead, and may enable the lead to be reconnected to the lead connector at a different point along the lead (e.g., closer to or farther away from the stimulating portion of the lead and/or electrode). In a non-limiting example, the lead connector may include a lock to prevent the patient from disconnecting the lead. The lock may be opened using, for example (but not limited to), a key, a tool (e.g., screw driver, wrench, and/or torque wrench), a code (e.g., combination) or with no tool. In another non-limiting example, the lead connector may minimize or eliminate damages and/or changes to the lead's structure, enabling the lead to remain sufficiently intact to generally reduce the risk of the lead fracturing and/or breaking and enable current flow through the entire lead. In another non-limiting example, a lead connector may be attached to the lead prior to and/or after insertion of an introducer system, enabling stimulation through the lead tip during the lead placement procedure. In some examples, the connector may be attached to the lead by dropping the lead into a slot or hole on the block and closing a flap which implements an insulation displacement connection (e.g., cutting through the insulative material aside to form a connection with the conductive lead wire). This lead connector may improve the speed and/or ease of lead connection because it can be attached with no use of tools (e.g., no wire cutters, scissors, and/or screwdrivers). For example, in this example, the lead may be placed into a slot in a lead connector block and secured using a lockable, reversible one-handed mechanism to displace the insulation on the lead body. The insulation displacement mechanism inside the lead connector may also cut the lead distal to the electrical connection. Once the connection has been made and the excess lead is trimmed, a lock (e.g., sliding, twisting, button press) may ensure that the flap on the block cannot be reopened accidentally. This feature prevents loss of connection between the lead connector and lead, which would result in loss of therapeutic benefit. The lead connector may mate with another lead connector (e.g., lead or plug to the stimulator) to complete the circuit from the stimulator to the lead tip electrode.

In some examples, the connection between the two lead connectors may be magnetic. In such examples, the shape of the lead connectors may prevent improper alignment of the lead connector (e.g., lead connectors that only fit together in one orientation). The magnetic connection may be used for both temporary and/or permanent stimulation delivery (e.g., during lead placement procedure and/or during patient's home use of the therapy). After obtaining proper lead placement location, the lead connector block may be removed and replaced following removal of the introducer system needle(s) and sheath(s). In some examples, the connection may be deactivated by pressing and/or sliding open the slot that contains the lead. In this example, the lead connector block may be removed or cut off prior to removal of the introducer and then quickly re-attached to a more proximal location on the lead. Following removal of the introducer, the lead may be placed in the slot and connected with a one-touch mechanism (e.g., pressing, sliding) and then the lead connector may be attached to the stimulator cable.

The magnetic connection may act as a quick-release connection that will prevent accidental lead (and/or electrode) dislodgement due to a pulled lead and/or cable. Instead of transferring force to the lead exit site and lead, any forces on the lead will be discharged due to the breaking of the magnetic connection between the lead and lead connector block. If desired by the clinician, a permanent connection may be made by locking the two-connector pieces together using a press button lock (and/or any other suitable lock). In addition to mating with the lead connector block, in some examples, the magnetic cable connector for the stimulator may also mate with an identical version of the lead connector block, which is connected to the test stimulator via a cable. In some examples, the magnetic cable connector originating from the stimulator may be bifurcated to connect with multiple lead connector blocks (e.g., to enable stimulation of two leads with one stimulator).

An exemplary stimulator may be able to provide at least the following parameters: amplitude of 0.1-30 mA; pulse duration of 10-200 μs; and frequency of 1-150 Hz. As a non-limiting example, an example stimulator may be able to provide ranges of parameters, such as ranges of intensities; range(s) of amplitudes (e.g., 0.2-20 mA, 0.1-30 mA, 0.1-40 mA, 0.1-50 mA); range(s) of pulse durations and/or pulse widths (e.g., of 10-100 μs, 10-200 μs, 10-100 μs, 10-300 μs, 1-1000 μs, 1-1500 μs, and/or 1-2000 μs; and ranges of frequency (e.g., of 1-20 Hz, 5-100 Hz, 1-100 Hz, 1-150 Hz, 1-200 Hz, 1-500 Hz, 1-1000 Hz, 1-1500 Hzm, 1-10,000 Hz, 1-100,000 Hz). The stimulator may be connected to software for wireless clinician programming of the therapy, software and hardware for a wireless patient controller, and firmware and hardware for a miniature body-mounted stimulator. This arrangement enables the clinician and/or patient to view and/or adjust treatment parameters while avoiding the need to interface with the stimulator directly. This can prevent a patient from having to remove clothing, etc., to reach the stimulator during use. In some examples, the stimulator may communicate via physical cables, wires, Bluetooth, and/or other wireless technologies. The present teachings are not limited to any particular configuration.

The patient controller may also provide a more extensive graphical user interface including a variety of other options (e.g., profiles specific to a time of day/type of pain/type of anticipated patient activity, access to information on pain management, means for communicating with a medical professional, etc.), thereby making it the primary means of initiating and/or altering the therapy. As with the stimulator, the controller communicates via physical wires/cables or wirelessly with the stimulator (or stimulators, if multiple stimulators are included in the system) and the optional programmer unit, described below. The controller may be relatively larger than the stimulator, although wireless connectivity would enable the user to carry the controller in clothing and/or generally at a convenient distance and location in comparison to the electrode and stimulator. The connections between the controller, stimulator, and introducer system may include any of those described herein (e.g., standard wired connections, wireless connections-particularly between the controller and the stimulator, wired connections relying on quick release mechanisms, etc.)

The stimulator enables adjustment of stimulation intensity by controlling stimulation amplitude and/or pulse duration, preferably with a single programmable parameter for intensity. Stimulation intensity itself may be determined by multiple parameters, including (but not limited to) stimulation amplitude and/or pulse duration. For example, stimulation intensity may be increased by increasing stimulation amplitude, pulse duration, or a combination of the two. Controlling multiple parameters such as stimulation amplitude and/or pulse duration using a single parameter may reduce the complexity of the procedure to program stimulation parameters by reducing the number of parameters that can be changed from 2 or more to 1. As a non-limiting example, the minimum of the stimulation intensity parameter (e.g., 0) may set the stimulation amplitude and pulse duration to their lowest values (e.g., 0.2 mA and 10 microseconds). As another non-limiting example, increasing the stimulation intensity parameter may change the stimulation amplitude, the pulse duration, or both.

In some examples, increasing the stimulation intensity parameter from the minimum value may first increase the stimulation amplitude while keeping the pulse duration at a minimum until the maximum value of the stimulation amplitude (e.g., 20-30 mA) is reached. Then, continuing to increase the stimulation intensity parameter may keep the stimulation amplitude fixed at the maximum value while increasing the pulse duration until the maximum value of the pulse duration is reached. In such examples, stimulation intensity is simple to program and may be increased while keeping pulse duration as low as possible, so as to keep the stimulation charge required to activate nerve fibers as low as possible and to increase the patient/clinician's ability to selectively stimulate large diameter fibers over small diameter fibers. In another non-limiting example, increasing the stimulation intensity parameter from the minimum value may first increase the stimulation amplitude while keeping stimulation amplitude at a minimum. Then, continuing to increase the stimulation intensity parameter beyond the maximum value of pulse duration (e.g., 200 microseconds)

may keep the pulse duration fixed at the maximum value while increasing the amplitude until the maximum value of the stimulation amplitude is reached. In this example, stimulation intensity increases while keeping stimulation amplitude as low as possible, which keeps the power consumption of the pulse as low as possible for a given charge per pulse.

The introducer system described herein may also reduce the risk of problems following lead placement by reducing the risk of lead fracture. This risk reduction results from the shape of the electrode itself, both in terms of its self-anchoring, migration-and-infection-resistant small diameter helix/coils and/or its distal anchoring system, and from the reduced levels of stress imposed upon the lead during the insertion and test stimulation process by way of being able to retract and protect the electrode during insertion and/or repositioning.

Other advantages include the ability to enable the duration of the lead placement and stimulation testing procedures to be minimized. The system also limits the number of percutaneous insertions required, decreases risk to the patient, enables efficient positioning and re-positioning of the lead for stimulation testing and/or lead deployment, enables clinicians to position and deploy the lead correctly and optimally with minimal or no additional training, and decreases the time required to form electrical connections for testing. As a result, the therapy can be delivered to patients by clinicians in settings/scenarios that were previously burdensome, not practical and/or not possible (e.g., to treat pre-operative, pen-operative, and/or post-operative pain). This introducer also overcomes limitations of previous systems by minimizing or eliminating the need for: a) the insertion via multiple percutaneous devices; b) re-positioning of the lead; and/or c) extended periods of time required for test stimulation and/or lead placement procedures.

An example may include increasing the strength of the coiled/helical lead by, for example, incorporating one or more conductor(s) or conductive wire(s), strand(s), filament(s) and/or cable(s) of high tensile strength materials (such as but not limited to MP35N, nickel-chromium-molybdenum super alloy) into the lead. Adding such strand(s) and/or replacing current lead wire strand(s) with such strand(s) and/or wire(s) increases the fracture-resistant capabilities of the lead, increasing the utility of self-anchoring, migration and/or infection resistant small-diameter coil/helix leads for use in electrical stimulation systems.

An example may include improving the strength of the lead by adding a new strand and/or filament within the open core/center of the helically coiled lead. In this non-limiting example, the new strand and/or filament would not completely fill the opening. There would remain a gap between the outside of the new strand and/or filament and the inside of the coiled wire. Moreover, this new strand and/or filament would not extend the entire length of the coiled lead. In this non-limiting example, these two provisions help the lead remain flexible with both axial and radial forces during normal use. When the lead is withdrawn, as the coiled wire straightens out, the inner diameter of the coils of the lead will reduce and/or the coiled wire becomes bound to the central strand/filament. Thus the lead has a higher tensile strength and reduced flexibility during the removal process compared to the normal use configuration. The new strand/filament in the core could be a metal (e.g., 316L or MP35N) or it may be a polymer (e.g., Aramid). Such an example could advantageously be combined with other aspects of the disclosed herein (e.g., the use of stylet proximate to—or even as part of—the strand and/or filament).

The present system for the percutaneous placement of a small-diameter coiled lead also reduces the risk of accidental lead dislodgement. This object of avoiding lead dislodgement is achieved with self-anchoring, migration and/or infection resistant small-diameter coil/helix leads. Further, these advantages are particularly useful (in comparison to previous systems) during the initial period of time in which the lead is left in place within the desired tissue (e.g., in the time period prior to complete encapsulation of the lead within connective tissue, or from 1 day to several months of indwelling). Other advantages (possibly in addition to others noted herein) include the ability to enable the duration of the lead placement and/or stimulation testing procedures to be minimized; a reduction in the number of percutaneous insertions required; a decrease risk to the patient by enabling efficient positioning and re-positioning of the lead for stimulation testing and/or correct/optimal lead deployment by clinicians with minimal or no additional training, as well as by decreasing the time required to form electrical connections for testing. Therapy may be delivered to patients by clinicians in settings/scenarios that were previously burdensome, not practical and/or not possible (e.g., to treat pre-operative, pen-operative, and/or post-operative pain).

Once the lead is placed in the patient, the introducing device may be disengaged and removed. A proximal portion of the lead may then be engaged with a lead connector unit. The lead connector may have an insulation displacement connector (IDC) and a groove and/or channel configured to receive a lead. The groove and/or channel may comprise a contact strip with receiving members (e.g., micro-structure barbs, snaps, magnets, etc.) to hold the lead in place.

An example lead connector may eliminate the need for a separate tool as it can enable a one-handed push mechanism for the clinician and/or patient. The lead connector unit may also include a break-away connection, e.g., the lead connector end includes a magnet with the opposing end of the lead connector cable end having metal and/or an oppositely charged magnet, enabling a clinician, patient, etc., to easily disconnect the cable from the unit. This magnetized or other type of connection can be integrated anywhere along the body of unit. The connection mechanism also contemplates other removable connection types, including snaps, adhesives, clips, Velcro®, force fittings, and/or any other appropriate means of connection.

Additionally, or alternatively, the connector may have a rotating element, such as a knob, dial, spool and/or post. The rotating element may engage the lead, mechanically and/or electrically, in order to assist in adjusting the tension of the detachable connection having tension formed by the electrode, the lead connector and the lead. The rotating element may include a predetermined tension release and/or recoil mechanism that responds to a disconnection force by releasing excess lead that is wound around the element. In the same manner, the lead connector may accomplish this tension release by slider or other movement that need not be rotational in nature. As with the detachable aspects of the lead connections, the tension release may occur at a force that is less than or equal to one-half the force required to dislodge and/or move the electrode from its initial position.

The IDC mechanism may assist in connecting the lead into the groove in order to enable the connection between the receiving members and the lead. In such an example, the clinician relies on his or her dominant or non-dominant hand to insert and connect the lead. The IDC mechanism may also be capable of stripping any insulation from the lead in order to establish better electrical contact between the lead and the unit, groove, and/or channel. The IDC may be formed integral with or separately attached to the lead connector unit.

Additionally or alternatively, the IDC may include a drawer(s) and/or tray(s), slot(s) and/or sliding mechanism(s) type mechanism and/or a pivoting disc that rotates relative to pivot, which is insertable into the body of the IDC and removable therefrom. A slot may bisect a portion of the disc. A slot may have an appropriate shape and size to firmly engage the lead within the disc and/or may include slidable portions, jaws, barbs, and/or the like. A disc may rotate so that the proximal end of the lead is fully inside the IDC while the other portion protrudes out of the unit. Springs, locks, and/or guiding mechanisms may also be provided to afford better control of the drawer(s) and/or tray(s), slot(s) and/or sliding mechanism(s), channel(s), and/or disc(s) when in operation.

Some examples may have a generally cylindrical shape. The IDC may include an aperture, slot and/or opening into which the lead may be inserted. The IDC may include an actuating lever AL to twist and/or rotate the body of IDC relative to the portion containing the slot so that the lead is secured inside the IDC 1089. Barbs may be included in the interior of the IDC if necessary to remove insulation from the lead to expose the underlying wire. Cooperating guides and/or grooves (not shown) may facilitate to the relative motion of the bodies and stops and locking mechanisms may also be included to prevent accidental motions.

The lead connector may be bifurcated to receive a plurality of leads. For example, multiple slots and/or funnels can connect multiple leads to a single stimulator to enable therapeutic stimulation to be provided to separate parts of the body.

The connection between the lead connector and electrode may be detachable. The detachability may include, without limitation, magnets, such as insert molded neodymium magnets, that may be formed on the connector and one or both ends of the lead (if on both ends, the stimulator would also have a detachable connection as described herein). Depending on the manufacturing process, the magnets, and how the magnets are fitted together, may enable differentiating the points of connections. For example, the lead connector may have a stepped connection port that fits with a correspondingly stepped connection on one of the lead. Alternatively, a circular magnet may sit on the top of the connector lead. A slight indentation and/or groove and/or other releasable force fitting could be provided to enable the experience of a "snap-in" feel which may provide the user with tactile and/or auditory and/or other feedback on the state of the connection.

In addition to or in place of magnets, a spring-loaded fitting could be used. The fitting is described generically so that it may be employed on any of the components, although particular utility is expected at the connection between the lead connector and the electrode.

In some examples, the lead connector and/or lead may include a detachable connection configured such that neither the stimulator not the lead are displaced if unwanted force is applied to them or their connection(s). For example, the connection between the lead and the stimulator may be detachable upon application of a predetermined force. The predetermined force may be calculated to generally prevent movement of the electrode once placed in the appropriate position within the patient.

Alternatively or in addition the lead may itself be detachable (e.g. in the middle so that it actually is a plurality of leads, e.g., two or more). The lead may be detachable at any point between the lead and the stimulator, e.g., lead may disconnect at either end. Further still, the predetermined detachable portion may be between the lead and stimulator, along any portion of the length of the lead. For example, two or more leads could be selectively attached at a detachment point to disconnect upon application of the predetermined force. Further, while the present disclosure notes that the portions are detachable, they may also be re-attachable. This may enable the system to serve as a failsafe mechanism to prevent damage and/or injury to the system, components, and/or the patient.

In addition to just safely detaching, the circuitry in the lead (and/or other components, such as the lead connector) may prevent delivery of unwanted stimulation in the event of a disconnection during stimulation. By way of a non-limiting example, the lead may be a "smart lead" that has components in addition to a path for electrical conduction that minimizes the risk of the patient experiencing unwanted stimulation (e.g., minimizes and/or eliminates the potential for the patient to experience a shock) when the lead is disconnected unexpectedly during use.

All of the above-mentioned connections rely on mated parts. In order to avoid improper installation, each of the mated pairs could be given a unique shape. Sensors or other circuitry could be employed at the connections points to better enhance the user alert feature described herein. Such sensors and/or circuitry could be inherent to the electrical signal delivering the stimulation, and/or separate signals could be established.

In some examples, the connection may be comprised of a lead connector lead end plug with at least two-prongs or three-prongs of steel electrical contract that attract to the magnetic armature of the lead connector end.

The lead may optionally couple with the stimulator. The stimulator may comprise a battery, a programmable memory unit, and circuitry necessary to deliver the therapeutic stimulation inherent to the system. In some examples, the battery may be embedded within the lead connector and/or another electrode. The battery may be thin, flexible, and powerful. The battery may contain a charge for use of at least 24 hours to maximize use before needing to be charged and/or replaced. The stimulator may also contain a graphical user interface to communicate with the patient and/or clinician. It may contain LED and/or other visual indicia to communicate actions, errors, and/or other pertinent information about the operation of the stimulation system. The stimulator may enable patient and/or clinician adjustments for the operation of the system. Additionally, the stimulator may be worn on a patient's body thereby minimizing cables and/or making the system easier to wear than conventional external stimulators. The stimulator may also be waterproof for ease of all-day wear.

Additionally, the introducing device may be paired with a custom bandage system that minimizes the risk of lead dislodgement during use. The lead and lead connector unit may be protected and/or attached to the patient with a custom bandage. The bandage may eliminate the need for a separate tape to secure the lead and/or lead connector. The bandage may integrate with the lead connector unit to enable the clinician and/or patient to easily and consistently remove and/or replace the bandage while avoiding inadvertently pulling the lead and/or otherwise dislodging it. The bandage may be comprised of the same film materials used in standard bandages, e.g., aperture or non-aperture films, including, but not limited to any polymeric material including, but not limited to polyethylene, metallocene catalyzed polyethylene, polypropylene, polyolefin copolymers, and/or ethylene vinyl acetate copolymers or other appropriate material. The bandage may also comprise adhesive material. Suitable adhesives may include, but are not limited to, acrylic based, dextrin based, and/or urethane based adhesives as well as natural and/or synthetic elastomers. The adhesives may also include amorphous polyolefin including amorphous polypropylene. In some examples, the bandage may have an adhesive perimeter including optional removal tabs. The adhesive perimeter may prevent the lead from being exposed to any adhesive surfaces and/or inadvertently being attached to the bandage. The center of the bandage may include an absorbent pad configured to cover the entry point of the lead into the patient. The absorbent pad may be configured to absorb any fluid exiting the lead insertion site, e.g., any kind of liquid (including, without limitation, blood, pus) that may ooze from the lead insertion site. The size of the pad may enable a patient and/or clinician to view the area around the lead exit site to determine the existence of any infections and/or abnormalities. The absorbent pad may be surrounded by a clear polyethylene section of the bandage that enables the clinician and/or patient to be able to better see the placement of the bandage. The pad itself might be clear and without adhesive to enable the clinician and/or patient to be able to better see the placement of the bandage, view the area around the lead exit site to determine for the existence of any infections and/or abnormalities while avoiding adhering to the lead and/or connectors to avoid accidental removal, fracture, and/or migration of the lead during bandage placement and/or replacement. A cutout in the adhesive perimeter of the bandage overlies the lead connector, eliminating gaps in the bandage seal, but enabling direct contact between a clinician and/or patient with the lead connector during the removal/attachment process. During removal, a patient and/or clinician can put his or her finger over the pad and the lead connector unit to generally prevent the lead from pulling the patient's skin. This may be particularly useful in difficult to reach position on the patient's body and/or on body parts with frequent movement, e.g., arms, legs, back, head, etc.

When applying and/or changing the bandage, a clinician and/or patient may disconnect the lead connector cable from the stimulator (not shown) and apply a temporary tape strip to apply pressure to the lead connector. The clinician and/or patient may apply additional pressure to the lead connector while removing the bandage from the patient. The site may then be inspected and/or cleaned. A new bandage may be applied to the site, the temporary tape strip may be removed, and the lead connector may be reconnected to the stimulator.

The present teachings are not limited to any specific treatment or indication. The system may apply to any kind of treatment, including, without limitation post-surgical pain patients or any type of pain patients, especially chronic pain patients (e.g. neuropathic pain, headache, and/or back pain patients).

A lead connector (e.g., any of the connectors described below) may include a lead storage mechanism to store excess portions of the lead (e.g., while the lead is coupled to the lead connector). This mechanism may reduce the excess length of lead between the lead connector and the point from which the lead exits the body. This may reduce the risk of the being caught on an object and/or being pulled and/or breaking. If the lead is caught, for example, on an external object or from a body part, then the excess lead stored on the mechanism may be released rather than dislodging or moving the lead from the tissue, fracturing the lead (inside or outside the body), and/or pulling the lead out and/or decoupling from the lead connector. In a non-limiting example, the mechanism may be a spool around which the lead is wound, either manually and/or automatically (e.g., using a spring). In another non-limiting example, the mechanism may be located on the outside of the lead connector or within the lead connector. In addition, the lead connector may be padded on one or more sides to provide comfort while wearing the lead connector.

As described below, the lead connector may also be designed to couple to the stimulator easily, and/or may enable connection using a single hand, such as by way of a magnetic connection. It should be understood, however, that while a magnetic connection is described, the connection maybe any mechanical connection in addition to or alternatively to the magnetic connection. The connection may be oriented at various angles with respect to the surface of the skin. In a non-limiting example, the connection is oriented generally perpendicular to the skin. In another non-limiting example, the connection is generally parallel to the surface of the skin. In another example, the connection may be easy for the user to make (e.g., does not require great dexterity, may be connected even without looking at the connectors) and/or strong enough to prevent inadvertent disconnection (e.g., due to common body movements and/or small forces, etc.) while disconnecting when subjected to stronger forces that may dislodge the lead (e.g., from external objects and/or body parts pulling or tugging on the lead connector and/or stimulator attached to the lead connector). The connection may prevent the lead from dislodging and/or fracturing by disconnecting the lead connector and/or lead when the lead is pulled rather than transmitting the force along the lead. In a non-limiting example, the magnetic connectors may be structured such that the surrounding magnetic field is reduced and/or avoids interfering with objects placed near the magnetic connectors (e.g., credit cards, cell phones).

Further still, the lead may connect directly to the stimulator (i.e., lead connector may be built into or integrally with the stimulator). The stimulator may be placed directly over or adjacent to the lead exit site to protect the exit site. There may be a clear window through which the lead exit site can be monitored for safety (e.g., infections, irritation).

In another non-limiting example, the lead may connect to the lead connector using a jack and plug, and the jack may be located on the lead and/or oriented at an angle (such as 90 degrees) to the lead. This jack may be connected to the plug on the lead connector using a downward force, enabling connection using a single hand. The very small distances between the magnetic armature of the plug and the permanent magnet structure of the lead connector means that the residual field outside the lead connector may be very small.

A cable may attach to the stimulator and/or be stored and/or organized (e.g., wound, coiled, wrapped around) to reduce the length of the lead (or leads) that may become caught, for example, on an external object or a body part. In a non-limiting example, the excess cable may be stored in a storage device attached to the cable, on the lead connector, and/or on the stimulator. In a non-limiting example, the storage device is a spool around which the cable may be wound manually or automatically (e.g., via a spring). In some examples, the cable may be coiled and/or wound around a spool on the stimulator, and forces on the lead cause the cable to be uncoiled from the spool rather than disconnect from the stimulator, transmit the force to the lead connector, and/or cable. In some examples, the cabling and/or any connectors may have detachable aspects to facilitate a tension release at a predetermined force that is less than the force required to dislodge the lead, move the electrode from its initial position, fracture the lead, and/or permanently deform the shape and/or structure of the lead.

The stimulation system may contain lead that attach to the stimulator available in multiple lengths. In a non-limiting example, the lead with the shortest length that enables connection between the stimulator and the lead connector may be selected to reduce the risk of the lead catching on an object or body part and/or disconnecting the system, dislodge the lead, and/or fracture the lead.

In some examples, the stimulator may enable coordinated stimulation across two or more stimulators. In the alternative or in addition, the controller and/or programmer unit may enable coordinated stimulation across two or more stimulators. Coordinated stimulation may enable stimulation across multiple stimulators to start and stop in a coordinated manner to avoid asynchronous activation of muscle on opposite sides of the body (e.g., the back and/or torso), which may cause loss of balance or discomfort. Control over stimulation across multiple stimulators may also prevent synchronized stimulation, for example, to avoid activation of opposing muscles (e.g., biceps and triceps), which may cause discomfort. In a non-limiting example, one of the stimulators, controller and/or programmer unit may communicate with other stimulators directly. In another non-limiting example, each stimulators may be connected to a central controlling unit, which may be another stimulator or may be a non-stimulating control unit. In a non-limiting example, communication among stimulators and/or control units (controller or programmer unit) may be wireless (e.g., via Bluetooth, Wi-Fi) or wired (e.g., cables).

A battery-operated, body-worn stimulator may generate electrical current that may be administered via the lead and/or introducer. In some examples, the stimulator is a small pod (e.g., with rounded contours and of minimal profile height) that is worn on the body via a gel patch electrode that serves as the return electrode and is connected with two snaps that also provide electrical connection. In some examples, the stimulator has a minimal user interfaces (e.g., a press button start/stop, LED lights and/or a speaker and/or buzzer) to provide critical feedback to the patient. For example, the lights may blink or light up (e.g., different colors and/or different flashing patterns) if the battery is low and/or if there is a problem with stimulation. This important feedback will alert the patient and/or clinician to address any issues, such as battery failure, gel pad detachment, and/or open connection. In the non-limiting example with a magnetic lead connector, it is important that the stimulator produces an alert if the quick-release cable is accidentally dislodged without the patient's knowledge. Additionally, lead errors that cause stimulation to stop due to, for example, high electrode impedance issues (e.g., due to lost connection between skin and/or return electrode), and/or can impact therapy usage time and/or therapeutic benefit received by the patient and the audible and/or visible alert of the stimulator prevents this. Further, In some examples, the stimulator memory will generate an activity log for documenting usage of the stimulator and/or errors during therapy. The stimulator log may include a list of errors that occurred, along with timestamps of the time that errors occurred, a history of usage time, including amplitude and/or stimulation parameter settings used. These features are important to ensure that patients are able to effectively use the stimulation and/or that clinicians can effectively monitor their stimulation usage.

An example breakaway mechanism may comprise a receptacle portion, including wire/lead contact point. The receptacle portion may include a magnet of any appropriate examples that include a contact point. The receptacle portion may include an iron magnetic stator, which may act as a pathway keeper. A mating portion of the breakaway mechanism may comprise of a plug. The plug may include an iron magnetic keeper path and a contact. The lead may be operatively attached with the plug.

The breakaway mechanism may include a spring loaded plunger mechanism. The plunger mechanism utilizes a pair of biasing members that may push plungers toward each other as the plug is inserted into the receptacle. This may secure the breakaway mechanism together. The force utilized to keep the breakaway mechanism together is defined such that any amount of force applied to the system that exceeds such force will cause the plug to separate from the receptacle, e.g., if there is a force applied to the lead because it snags on something. This will generally protect the system. In particular, it generally prevents the lead and/or electrode from becoming disengaged and/or moved from their intended position.

An example of a system for testing, positioning, introducing and/or deploying a lead for percutaneous peripheral nerve stimulation comprises a percutaneous sleeve, a stimulating probe, a lead, and/or an introducer is described herein. The percutaneous sleeve may also be referred to as an introducer sheath or introducing sheath without changing the component referenced. The stimulating probe may also be referred to as a test needle or testing needle without changing the component referenced. The introducer may also be referred to as an introducing needle or introducer needle without changing the component referenced. The percutaneous sleeve and/or introducing sheath may advantageously consist of a hub and a shaft with an inner lumen, the distal portion of the sheath forming a terminal opening. The stimulating probe or testing needle may advantageously consist of a hub and a shaft, the distal end of the shaft may incorporate one or more bevels, and the shaft having an outer diameter sufficiently small such that it may pass into the lumen of the percutaneous sleeve with minimal friction, but avoiding enough space between the two components to enable tissue to be caught between them during insertion into skin, muscle, and/or other tissue. The introducer may advantageously consist of a hub and shaft with an inner lumen of sufficient diameter to enable the stimulation lead to reside within and/or pass through it, the distal portion of the needle consisting of one or more bevel(s) forming the terminal opening, the outer diameter of the introducing needle shaft being sufficiently less than that of the percutaneous sleeve lumen such that the introducer with the stimulation lead within it and the anchor secured over the edge of the introducer lumen can be inserted through the percutaneous sleeve lumen while avoiding damage and/or disruption to the stimulation lead.

An example system for testing, positioning, introducing and/or deploying a lead for percutaneous peripheral nerve stimulation comprises in part a percutaneous sleeve, a stimulating probe, a lead, and/or an introducer is described herein. The percutaneous sleeve and/or introducing sheath may advantageously consist of a hub and a shaft with an inner lumen, the distal portion of the sheath forming a terminal opening. The stimulating probe and/or testing needle may advantageously consist of a hub and a shaft, the distal end of the shaft may incorporate one or more bevels, and the shaft having an outer diameter such that it may be inserted into and/or through the lumen of the percutaneous sleeve while avoiding friction that prevents the component from being moved while avoiding disrupting the position of the sleeve, while also avoiding catching tissue between the two components during insertion into skin, muscle, and/or other tissue. The introducer may advantageously consist of a hub and shaft with an inner lumen of sufficient diameter to enable the stimulation lead to be carried within and/or advance through it, the distal portion of the needle consisting of one or more bevel(s) forming the terminal opening, the outer diameter of the introducing needle shaft being sufficiently less than that of the percutaneous sleeve lumen such that the introducer with the stimulation lead within it and the anchor secured over the edge of the introducer lumen can be inserted through the percutaneous sleeve lumen while avoiding causing damage and/or disruption to the stimulation lead.

As a non-limiting example, the introducing sheath could be inserted with the testing needle, which could be embodied as a solid metal needle with no lumen, indwelling inside of it. Stimulation testing could then be delivered through the testing needle, and/or the system could be freely repositioned as needed while avoiding deploying the lead. After finding the ideal location, the testing needle would be withdrawn while the introducing sheath remains in place. The introducing needle (with the lead) could then be inserted through the lumen of the introducing sheath. Both the introducer sheath and introducing needle could then be withdrawn together to deploy the lead.

In one non-limiting example, the percutaneous sleeve may incorporate a hypodermic needle with an outer diameter of approximately 1.49-1.51 mm, 1-2 mm, and/or 0.5-2.5 mm outer diameter, and 1.36-1.4 mm, 1.01-1.99 mm, and/or 0.51-2.49 mm inner diameter. The length of the needle portion of the sleeve may be 90-100 mm, 60-130 mm, and/or 30-160 mm in length. In some examples, the needle length would be sufficient to enable targeting of deeper nerves (e.g., the sciatic nerve) in larger patients. In some examples, the needle length may be minimized such that torque from the weight of the hub is reduced while targeting shallower nerves (e.g., the femoral nerve), thereby reducing the tendency of the components to disturb the final location of the needle tips and the lead.

In one non-limiting example, the stimulating probe may have an outer diameter such that it acts as a non-coring insert when inside the percutaneous sleeve (e.g., in one non-limiting example, an outer diameter of 1.3-1.4 mm if the introducing sleeve were to have an outer diameter of 1.49-1.51 mm). The length of the needle portion of the stimulating probe may be approximately 120-125 mm, 70-150 mm, and/or 35-180 mm in length. In some examples, the length of the stimulating probe is longer than the percutaneous sleeve such that test stimulation may be delivered through the electrode portion of the stimulating probe.

In one non-limiting example, the introducer needle may have an outer diameter such that, with the anchor of the lead secured over the edge of the distal lumen edge, the introducer needle and lead anchor are able to pass through the percutaneous sleeve lumen while avoiding damaging the lead anchor. The outer diameter of the introducer needle may desirably be 0.902-0.914 mm, 0.7-1.1 mm, and/or 0.35-2.35 mm. In some examples, inner diameter of the introducer needle may desirably be 0.749-0.800 mm, 0.5-1 mm, and/or 0.3-2.3 mm. The inner diameter of the percutaneous sleeve must be sufficiently large to enable the main body of the lead to reside within it and be withdrawn over it. The length of the needle may be approximately 120-130 mm, 70-150 mm, and/or 35-180 mm in length. In some examples, the length of the introducer needle is longer than the percutaneous sleeve such that the entire anchor of the lead is protruding beyond the distal end of the percutaneous sleeve into tissue such that the lead deploys.

The anchor of the lead bending over the first edge of the terminal opening of the introducing needle may cause the lead to engage the tissue, causing the lead to self-anchor upon withdrawal of the introducer needle.

The testing needle does not need to have an inner lumen (i.e., it can be a solid needle), which could advantageously avoid tissue coring, tearing, and/or other types of tissue damage. The testing needle may be made from any material that conducts electricity, is able to hold a sharp point, and is safe for insertion into humans and/or is biocompatible. The testing needle may also be made from a non-conductive material if some portion of it and/or a component within it is capable of conducting electricity. As some skilled in the art will be able to discern, many materials, including various metals, meet these requirements. In some examples, the testing needle may be constructed of stainless steel.

The introducer needle and/or the testing needle maybe have one or more bevels. Having one or more bevels is desirable as it enables the needle(s) to be inserted into tissue avoiding the need to use any surgical (and/or other) tools (e.g., a scalpel).

In some examples, a conductive test needle may have an electrical connector integrally connected, that is, may have a plug integrally connected, possibly via one or more sections of cable. The electrical connector may desirably be mechanically and/or electrically mated to the needle. Having a plug built into the hub of the testing needle avoids the need to use an external connector component to facilitate the delivery of stimulation during testing.

The electrically conductive testing needle and/or stimulating probe may be coated with an insulating material except for an exposed, electrically conductive portion of the needle in proximity to and either incorporating or not incorporating the most distal tip of the needle. This exposed portion enables test stimulation to be delivered through the testing needle. In one non-limiting example, the electrically exposed portion of the needle, and/or the electrode, may have a surface area of 1-10 mm2. In another non-limiting example, the electrode may have a surface area of 10-100 mm2. In yet another non-limiting example, the electrode may have a surface area of 100-500 mm2.

The introducer needle may have an electrical connector integrally mated with the electrically conductive introducing needle such that the electrical connector is mechanically and/or electrically mated to the needle. Having a plug built into the hub of the introducer needle avoids the need to use an external connector component to stimulate through the lead. The electrically conductive introducing needle may be coated with an insulating material except for an exposed, electrically conductive portion of the needle, including or desirably not including, the terminal opening. In one non-limiting example, the electrically exposed portion of the needle, and/or the electrode, may have a surface area of 1-10 mm2. In another non-limiting example, the electrode may have a surface area of 10-100 mm2. In yet another non-limiting example, the electrode may have a surface area of 100-500 mm2. This exposed portion enables test stimulation to be delivered through the tip of the needle. Because the tip of the needle also touches the lead electrode and/or anchor, stimulation is delivered through the lead.

The introducing sheath, test needle, and/or the introducing needle may incorporate into the proximal end(s) an ergonomic, light-weight hub with textured surfaces that provide grip and control during insertion into tissue and/or adjustment within tissue. The hub(s) may be attached to the needle(s) in a variety of ways, including welding crimping, gluing, and/or overmolding. The proximal surface of the needle(s) may be roughened to facilitate bonding of the hub(s) to the needle(s). An ergonomic hub is important as it provides better control of the needle during insertion, especially in patients with tougher skin, which can be challenging to insert the system through without an adequate position to grip the introducer system. Minimizing the weight of the hub is important as when it is left in place during testing, this part of the system provides the greatest torque to the system, tending to distort/displace the tissue and/or potentially creating differences between stimulation during testing and after lead deployment.

A non-limiting example of a lightweight hub may desirably be a hub whose weight avoids producing torque upon the system which displaces the needle tip by more than 0.25 mm, 1 mm, and/or 5 mm when one third or more of the length of the needle is indwelling in tissue. Another non-limiting example of a lightweight hub may desirably consist of a hub whose weight comprises not more than one quarter, one third, one half, three quarters, and/or nine tenths of the total weight of the component.

The hub of the testing needle and the hub of the introducing sheath may reversibly lock or connect together through means such as a snap, a twisting lock, and/or other means of forming a temporary connection. Enabling the testing needle and the introducing sheath to lock together ensures that the components stay in the appropriate positions relative to each other during insertion, testing, and/or re-positioning. This locking mechanism may be reversible such that once the correct location is identified the testing needle can be withdrawn through the introducing sheath and avoid changing the position of the introducing sheath. In one non-limiting example, one or more tabs or protrusions on the hub of the stimulating probe may fit into slots and/or keyways in the hub of the percutaneous sleeve, enabling the hubs to be mated together with a small twist of the two components relative to each other. This mechanism may reduce the force applied along the length of the needles needed to unlock the two components from each other, which in turn avoids the displacement of the percutaneous sleeve from the target location.

The hub of the introducing needle and the hub of the introducing sheath may reversibly or irreversibly lock and/or connect together through means such as a snap, a twisting lock, and/or other means of forming a temporary and/or permanent connection. Enabling the introducing needle and the introducing sheath to lock together ensures that the components stay in the appropriate positions relative to each other during lead insertion and/or deployment. This locking mechanism may not be easily reversible, as once the introducing needle is inserted all the way into the introducing sheath, both may be withdrawn together during lead deployment.

All materials for system may be biocompatible and/or lightweight, with plastics being preferred compliments to the steel components. Also, the hub/handle may be sufficiently well balanced and/or weighted to enable one handed manipulation of the system. To that end, some examples herein may advantageously ensure probe and needle are as similar as possible in terms of length, weight, and/or feel. A gripping loop, flanged wings, and/or contours within the handle itself may also be provided to enhance the overall use.

A locking mechanism enables for reversible or irreversible connection between the connectors and the hub/handle of the respective component. In each case, connector couples to the proximal wires extending out of the components.

What has been described above includes examples of the present specification. It is, of course, not possible to describe every conceivable combination of components or methodologies for purposes of describing the present specification, but one of ordinary skill in the art may recognize that many further combinations and permutations of the present specification are possible. Each of the components described above may be combined or added together in any permutation to define the introducer system. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

Challenges addressed by the system and methods herein include minimizing and/or mitigating forces on or risks to the implanted lead, cabling, and/or other connected components so as to keep the forces experienced by the lead and/or its directly-connected system components low enough to prevent lead dislodgement, migration, fracture, damage, and/or permanent deformation but while maintaining an electrical and mechanical connection during but not limited to everyday use, connection and/or disconnection, periods of activity, bathing, and/or sleeping and/or while performing bandage changes to care for the exit site of the percutaneous lead so as to sufficiently maintain the delivery of therapeutic stimulation. As a non-limiting example, system components may maintain a consistent mechanical and electrical connection during movements such as walking, but if components (e.g. cable(s)) were to catch on a doorknob during this movement the sudden force on the system would cause the components to disconnect rather than dislodge, fracture, cause the migration of, and/or permanently deform the percutaneous lead. In another non-limiting example, system components may disconnect if they were to catch on a patient's clothing while dressing so as to prevent the dislodgement, fracture, migration, or and/or permanent deformation of the percutaneous lead, but may otherwise remain connected during movements such as moving from standing to sitting so as to maintain a mechanical and electrical connection and reduce disruptions in the therapy period.

The system may consist of one or more break away (e.g., disconnection) mechanisms along cabling and/or connectors to reduce the inadvertent transfer of forces along the implanted lead but avoid unnecessary disruption in therapy. The system described may overcome the challenges of limiting unwanted or inadvertent forces upon the percutaneous lead while maintaining a consistent mechanical and electrical connection by incorporating break away and/or disconnection points (e.g., preplanned, prespecified, preferable, and/or intentional disconnection point(s), region(s), or locations(s)) at one or more components or locations which may experience a higher number and type of forces capable of contributing to dislodgement, fracture, migration, damage, and/or permanent deformation of the percutaneous lead, including but not limited to inadvertently adhering to bandages during bandage changes, catching on external objects (e.g., clothing) or other components of the system, and/or shifting and/or shearing forces from standard, non-standard, expected, unexpected, and/or unusual body movements (e.g., limb bending or extension, moving from standing to sitting, moving from sitting to standing) but while enabling continuity in therapy delivery by maintaining an optimally strong enough (e.g., sufficiently strong but not too strong)

mechanical and electrical connection among components to limit disruptions in therapy, user frustration (e.g., by having to reset and/or restart stimulation following component disconnection unnecessarily), and/or ineffective therapy (e.g., by reduced or lessened therapy hours by means of the patient not recognizing disconnected components or failing to reset/restart stimulation following component disconnection). In a non-limiting example, the length of cable which passes under or beneath bandaging (and therefore has an increased risk of catching during a bandage change) may not only contain a break away mechanism (e.g., magnet) at the portion of the cable exterior to the bandage to limit the transfer of force to the percutaneous lead should the cabling become inadvertently caught or pulled on, but may additionally contain a break away mechanism (e.g., magnet) at the portion of the cable interior to the bandage so that should that portion, section, or length of cabling passing under the bandage be unintentionally pulled during the (intended and/or unintended partial or complete) removal of a bandage it may release from the lead connector and prevent the transfer of force to the percutaneous lead which may otherwise result in a dislodgement, fracture, migration, damage, and/or permanent deformation of the lead. The described break away mechanism(s) may be comprised of, but not limited to, a magnet and may be located at any location along the cabling and/or lead connector exterior, interior or underneath to the bandage.

The systems and methods described herein overcome the challenge of connecting a small (e.g., with optimal sizes of less than 1.0 mm and, more preferably, less than 0.7 mm) flexible lead to a generator via cabling during in-procedure testing through the design of a new mechanical and electrical connection to the microlead which can be completed while wearing surgical gloves and/or single-handedly in order to speed up procedure times while limiting the chance of electrode movement from the originally intended position (e.g., by inadvertently tugging on the lead while making the connection). In some examples, the mechanical and electrical connection to the percutaneous fine-wire lead may incorporate ridges, grooves, and/or bumps protruding some amount to provide adequate traction when gripping with a gloved hand potentially soiled with ultrasound gel and/or other material present during surgical procedures but avoiding sharp edges or protruding so much that these ridges, grooves, and/or bumps compromise sterile and/or waterproof bandaging, nor cause discomfort to the patient using the system. In some examples, the mechanical and electrical connection to the percutaneous fine-wire lead may be of small enough size (e.g., length and/or width less than 3 cm) with a shallow enough profile (e.g., 0.3-1 cm) to fit comfortably beneath a waterproof and/or protective bandage but of a large enough size to be comfortable held in a gloved hand potentially soiled with ultrasound gel and/or other material present during surgical procedures.

The lead connector may be designed to make the mechanical and electrical connection to the fine-wire lead during in-procedure testing while wearing surgical gloves (which may be soiled with, as an example, ultrasound gel) and/or single-handedly in order to speed up procedure times while limiting the chance of electrode movement from the originally intended position (e.g., by inadvertently tugging on the lead while making the connection). The system described may incorporate a channel, groove, or tunnel in which the lead may be fed, wound, and/or laid into to enable conductive teeth and/or barbs to penetrate the insulative barrier coating the lead while avoiding damaging or severing the conductive wire(s) or conductor(s), strand(s), filament(s) and/or cable(s) within or comprising the lead. In one example, the lead may be affixed into place in the aforementioned channel(s), groove(s), and/or tunnel(s) of the connector by pressing a hinged flap shut and flexible molding snaps into place to hold the flap closed, and/or the hinged flap may be held into place by the tension of a spring, and/or the hinged flap may be held into place by a rotating (e.g., locking) mechanism. In another example, the lead may be affixed into place in the aforementioned channel(s), groove(s), and/or tunnel(s) of the connector by folding and/or winding a material (e.g., flexible silicone, plastic clamp(s)) over the lead. In another example, the lead may be affixed into place in the aforementioned channel(s), groove(s), and/or tunnel(s) of the connector by a sliding drawer(s) and/or tray(s), slot(s) and/or sliding mechanism(s) mechanism which may be held into place by a flexible molding that snaps into place, the tension of a spring, and/or a rotating (e.g., locking) mechanism. Release of the lead secured within and/or to the connector may require a two-finger pinch (e.g., pressing on both sides of the connector inwards), a tab pulled down and/or away from a securing molded lip, the displacement of a spring, the rotation of one surface (e.g., against grooves), and/or the use of a key.

The connector may be held in position to avoid pulling and/or tugging on the lead due to movement or shifting of the connector under bandaging or during bandage changes by means of a mount or cradle.

In some examples, bandages may be designed to maintain a waterproof seal between the lead exit site and the external environment while maintaining a breathable (e.g., allows water to escape while allowing oxygen in) nature. The bandages may contain a nonstick center to cover the lead exit site and external portion of the lead (e.g., following percutaneous placement in which part of the lead is inside the body and part of the lead is outside of the body) while incorporating an adhesive outer edge to repel water. A connector may penetrate the waterproof bandage to provide an electrical connection between the lead and the cabling to the generator while maintaining the waterproof nature by adhering, gripping, suctioning, and/or locking into the bandaging components. The bandages may consist of a structured protective component and a waterproof adhesive component.

The bandages may enable and/or facilitate for an electrical connection to be made between the lead exit site and cabling to the generator while limiting stresses placed upon the lead which may contribute to the dislodgment, fracture, and/or movement of the electrode from its initial location while maintaining a protective barrier between the lead exit site and external forces and/or external pollutants or microbes. In some examples, the cabling may pass under an adhesive bandage sufficiently flexible to fold around the cabling and hold it in position while preventing compromise of the waterproof nature of the bandage. In another example, a channel and/or tunnel may secure cabling into position by enabling the passage of a cable through a shaped (e.g., thermoformed plastic or silicone) protective cover, and/or through a flexible (e.g., foam) protective ring that surrounds the lead exit site. This protective cover and/or ring may adhere to the skin itself or may require the placement of an adhesive bandage over it. In some examples, this channel and/or tunnel may secure the cable away from the lead exit site radially (e.g., by enabling the securement of the cable between the protective cover and/or ring and the surface of the skin). In another example, this channel may pass through the body of the protective cover and then pass radially out under a waterproof bandage sufficiently flexible to fold around the cabling and maintain a waterproof seal, and/or may pass through both the body of the protective cover as well as the body of the waterproof bandage and adhere, grip, suction, and/or lock to maintain a waterproof seal. In another example, a magnet (and/or magnets) may be molded, secured, and/or adhered to the protective cover to secure the cabling passing out of the protective cover and limit the transfer of force that may place unwanted stress upon the lead and/or lead exit site. In a non-limiting example, such magnet(s) may secure the cabling external to the protective cover and/or waterproof seal to or through a conductive portal(s) in the protective cover and/or waterproof seal. The force of this magnet(s) may be less than the force required to dislodge, fracture, or otherwise move the lead from its intended location so that inadvertent tug(s) or pull(s) on the cabling may result in this magnetic connection releasing and avoid the transfer of force to the lead. In another non-limiting example, such magnet(s) may secure the cabling to, through, or under the protective cover and/or waterproof bandage and release to avoid the transfer of unwanted forces (e.g., unwanted tugs or pulls on the cabling) to the lead without contributing to the stimulation circuitry (e.g., a cable which may contribute to the stimulation circuitry may adhere to a magnet on, through, or under the protective cover which is not an element of the stimulation circuitry).

As a non-limiting example, portion(s) of the protective cover and/or the waterproof seal may include a conductive material(s) or have one or more conductor(s) or conductive wire(s), strand(s), filament(s) and/or cable(s) so that no cabling and/or wires need pass through and/or under the bandages (which may or may not be waterproof and/or water resistant) and may instead transfer electrical signal between the external pulse generator and lead via this conductive material or conductor(s)). Cabling may adhere to this conductive material via a mechanism, such as a snap, magnet, suction, and/or adhesive and may disconnect at a specified or prespecified force or range of forces (e.g., at a force less than the force required to dislodge, fracture, and/or otherwise move the implanted lead from its original position.

As a non-limiting example, bandages may be used, designed, and/or integrated with other system components, and/or the overall system to overcome, mitigate, reduce, and/or address the stresses and/or forces that may occur during and/or during daily activities of the patient (e.g., during dressing and undressing, using the toilet, walking up and down stairs, sitting, standing), movement (e.g., going from sitting to standing, going from standing to sitting, housework, yardwork), physical activity (e.g., exercise, sports, stretching), and/or sleep (e.g., when the patient unknowingly shifts and/or rolls, and/or when extra blankets, sheets, and/or clothing may be surrounding the patient, and/or when less clothing may be securing cabling and/or bandages in place, and/or when greater movement and/or shifting may be required to move from a laying to sitting position or a sitting to laying position) and prevent inadvertent and/or unwanted lead dislodgement(s), fracture(s), and/or movement(s) of the lead(s) and/or electrode(s) from its intended location(s) from, but not limited to, bandages peeling up on the edges, bandages sticking to sheets and/or clothing, and/or bandages shifting due to causes such as moisture, water, lotion, oil, and/or sweat. In a non-limiting example, the edges of the bandage may be coated with a strong adhesive, and/or reinforced with a fabric-type material. In another non-limiting example, an additional bandage that integrates with the original bandaging may be provided for use at night and/or during strenuous activity. In some examples, this bandage may provide an extra barrier between the original bandage and sheets and/or clothing. In some examples, this bandage may include extra padding and/or compression to reduce the transfer of force from inadvertent weight shift onto/off-of the lead exit site. In some examples, this bandage may be made of a material which provides a cooling sensation and/or pulls sweat away from the original bandage (e.g., by moisture wicking).

Additional non-limiting examples of the interaction of the connector with the lead may include straightening the lead or coiling the lead. Coiling the lead may allow the coiled portion to act as a shock absorber. Straightening the lead on the other hand may result in the connector causing the lead start to interact like a rope instead of a coil. Further, the number of blades to contact the connector/lead may result in different performance. For example, too few blades and the electrical connection may fail to be robust throughout extended home use. Too many blades and the integrity of the lead and/or connector may degrade. Further, the pressure or force that the type of blade interaction causes on the rest of the connector/lead and presence or absence of a spring like force may affect performance. For example, not having the spring like force may reduce the amount of force needed to pull the lead from the patient. Moreover, the pressure on the blades may be adjusted so that it is less than the force required to dislodge the lead from the patient/user. Further still, instead of a magnetic force, friction may to help mechanically hold the lead and connector in place.

If the system includes too many blades it may make it too difficult to operate, use, and close the connector on or to the lead, which may impact the ability of the user to operate the connector with a one handed and ideally two finger (e.g., index finger and thumb) use or operation. The importance of the limitation that the user may only be able to apply a limited about of force due to the need to use friction to close the device, which may be significantly limited since the user e.g., clinician may be wearing gloves and/or have their hands or gloves covered or coated with a lubricating fluid, gel, or material such as ultrasound gel, which can make lubricate the critical surfaces and reduce the amount of force that can be applied to the connector, thereby limiting the amount of force that can be used to close the connector and cause the blades and the rest of the applicable parts of the connector to interact and correctly mechanically and electrically connect with the lead.

Examples of overcoming the challenges of use and to enable closure of the connector on the lead are important since the connector would optimally be able to be closed with a one handed and ideally two finger (e.g., index finger and thumb) use or operation.

Figure 1:
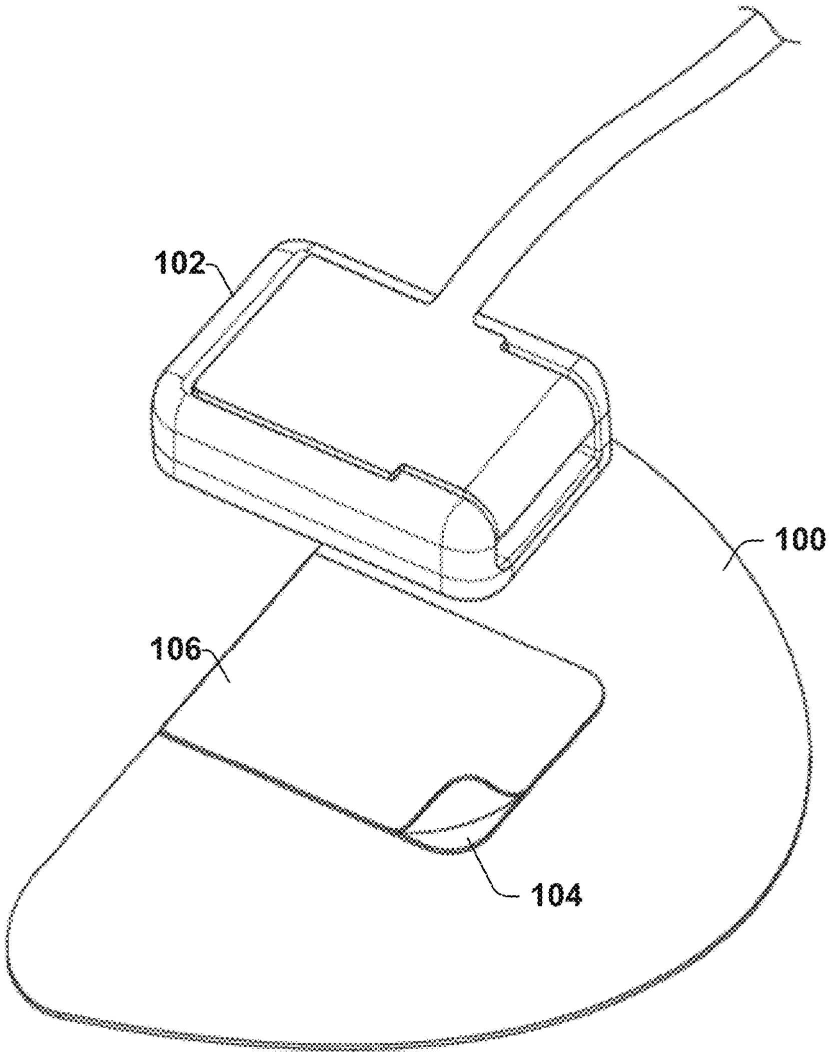
FIG. 1 illustrates an example connector and adhesive layer to interface between skin of a patient and the connector, in accordance with the teachings of this disclosure.

FIG. 1 illustrates pad 100 configured to interface between a lead connector 102 and skin of a patient. The adhesive pad 100 that includes an adhesive strip 104 configured attach to the lead connector 102 to affix the lead connector 102 to the adhesive pad 100. In the illustrated example, the adhesive strip 104 has a removable cover 106 that protects the adhesive strip 104 until it is to be coupled to the lead connector 102. In the illustrated example of FIG. 1, the adhesive strip 104 is configured to adhere to the lead connector 102. Alternatively, in some examples, the adhesive strip 104 adheres to a connector base (as described below).

Figure 2:
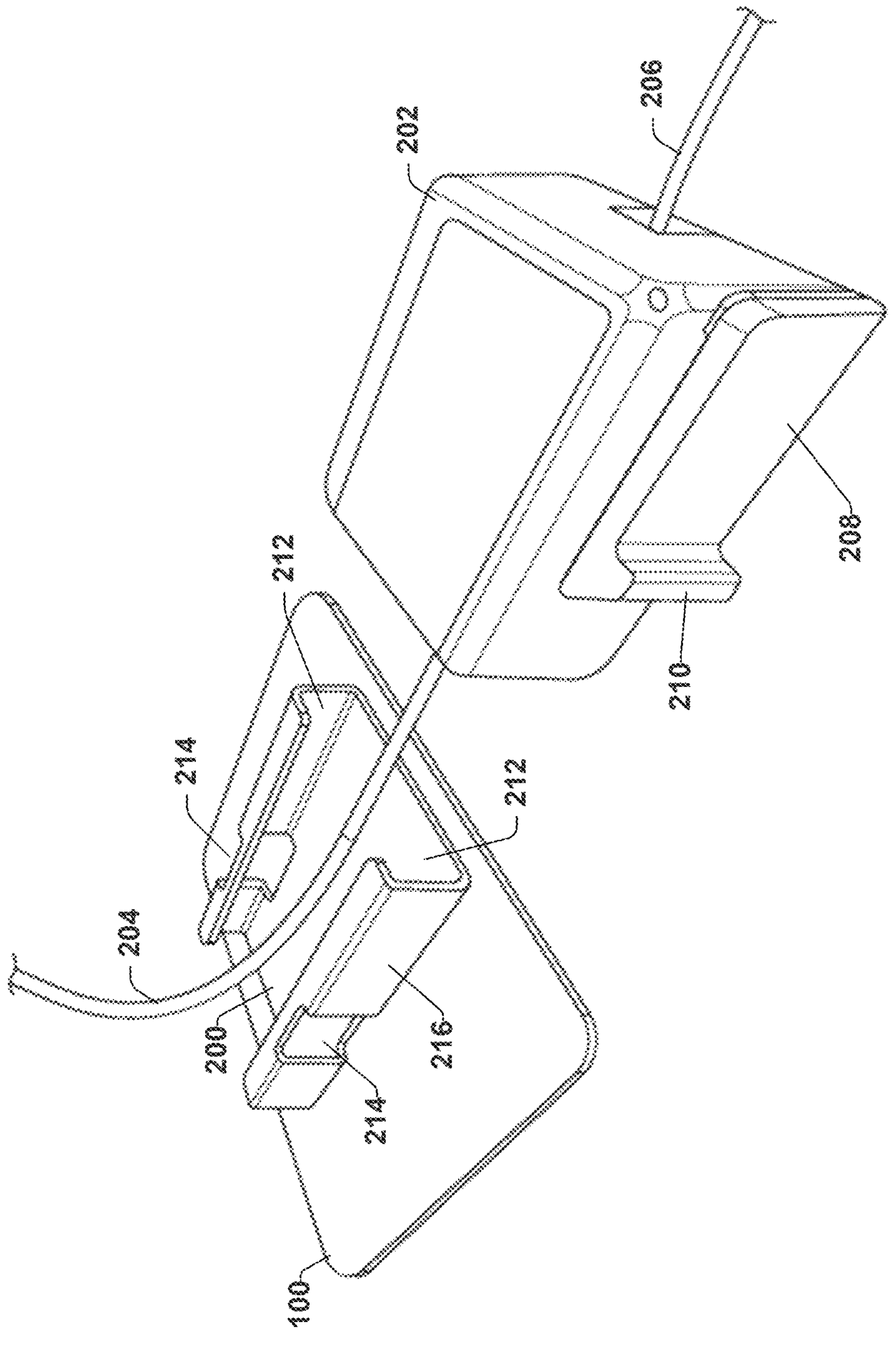
FIG. 2 illustrates an example connector that is slidably lockable with a connector base, in accordance with the teachings of this disclosure.

FIG. 2 illustrates a connector base 200 (sometimes referred to as a "connector cradle" or "cradle") configured to slidably engage with a connector 202. In the example of FIG. 2, the connector base 200 is attached to the patient via the adhesive pad 100 of FIG. 1. In the illustrated example, the connector 202 has an integrated cable 204. However, the connector 202 may be any connector described herein. The connector 202 provides an interface between the cable 204 that electronically couples to a nerve stimulation device (not shown) that provides stimulation signals to a lead 206 via the cable 204 and the connector 202.

In the illustrated example, the connector 202 includes snap tabs 208. In some examples, the snap tabs 208 are integrally formed with a body of the connector 202. The snap tabs 208 include a head portion 210 that is configured to slide into a channel 212 defined by the connector base 200 and snap into apertures 214 defined by the connector base 200. The connector base 200 is at least partially flexible to accommodate insertion and removal of the connector 202. For example, to remove the connector 202, the connector base 200 may tolerate a force perpendicular to walls 216 of the connector base 200 to facilitate the head portion 210 of the snap tabs 208 to be removed from the apertures 214.

FIGS. 3A, 3B, and 3C illustrate another example connector 300 that is slidably engageable with a connector base 302. In the example of FIGS. 3A, 3B, and 3C, the connector base 302 is attached to the patient via the adhesive pad 100 of FIG. 1. In the illustrated example, the connector 300 has an integrated cable 204. However, the connector 300 may be any connector described herein. The connector 300 provides an interface between the cable 204 that electronically couples to a nerve stimulation device (not shown) that provides stimulation signals to the lead 206 via the cable 204 and the connector 300.

The connector base 302 includes three sidewalls, a top wall, and a foot to provide a connection surface with the adhesive pad 100. The connector base 302 is configured to, in conjunction with the adhesive pad 100, encase the connector 300 to prevent or inhibit the connector 300 from lifting when a bandage or transparent dressing (such as TEGADERM™, etc.) is removed. In the illustrated example, the connector base 302 defines tab channels 304 and a cable cutout 306. The tab channels 304 are configured to receive corresponding tabs 308 of the connector 300. In some examples, the tab channels 304 and tabs 308 are configured to provide a friction fit between the connector 300 and the connector base 302. In the illustrated examples, the cable cutout 306 in on a side wall of the connector base 302. However, alternatively or additionally, in some examples, the cable cutout 306 may be located on a top wall of the connector base 302 to accommodate connectors with cable interfaces on top of the connector (e.g., see the connector in FIGS. 21A, 21B, and 21C below).

FIGS. 4A, 4B, 4C, 4D, and 4E illustrate an example connector 400 that is vertically lockable with a connector base 402. In the example of FIGS. 4A, 4B, 4C, 4D, and 4E, the connector base 402 is attached to the patient via the adhesive pad 100 of FIG. 1. In the illustrated example, the connector 400 has an integrated cable 204. However, the connector 400 may be any connector described herein. The connector 400 provides an interface between the cable 204 that electronically couples to a nerve stimulation device (not shown) that provides stimulation signals to the lead 206 via the cable 204 and the connector 400.

Figure 4A:
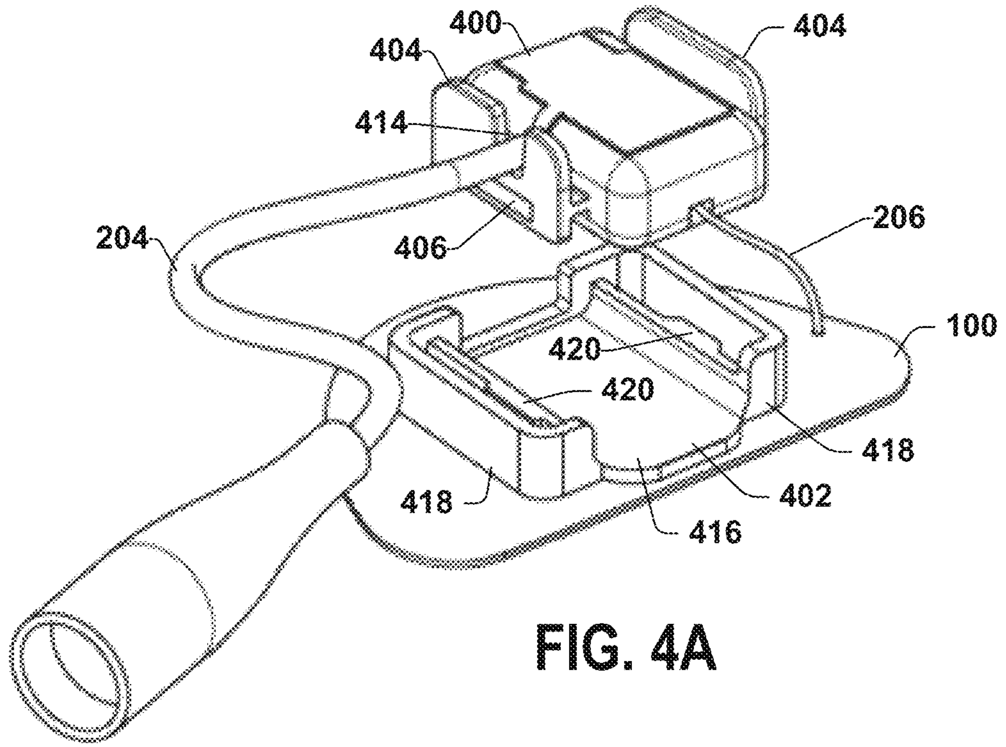
Figure 4B:
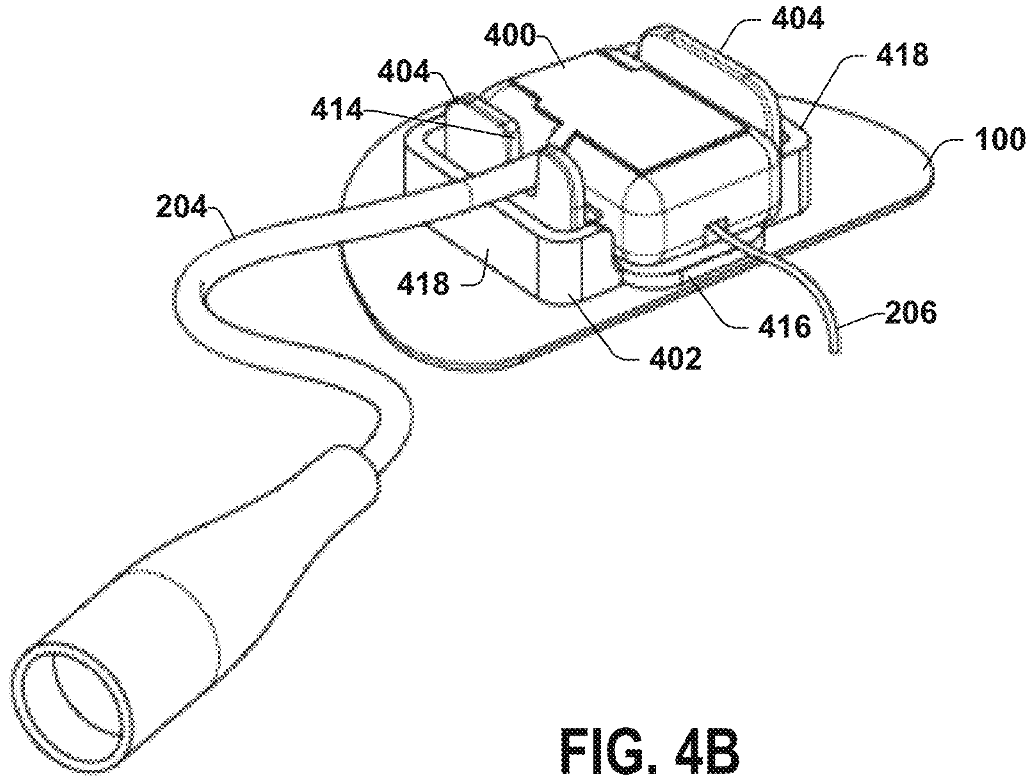
Figure 4C:
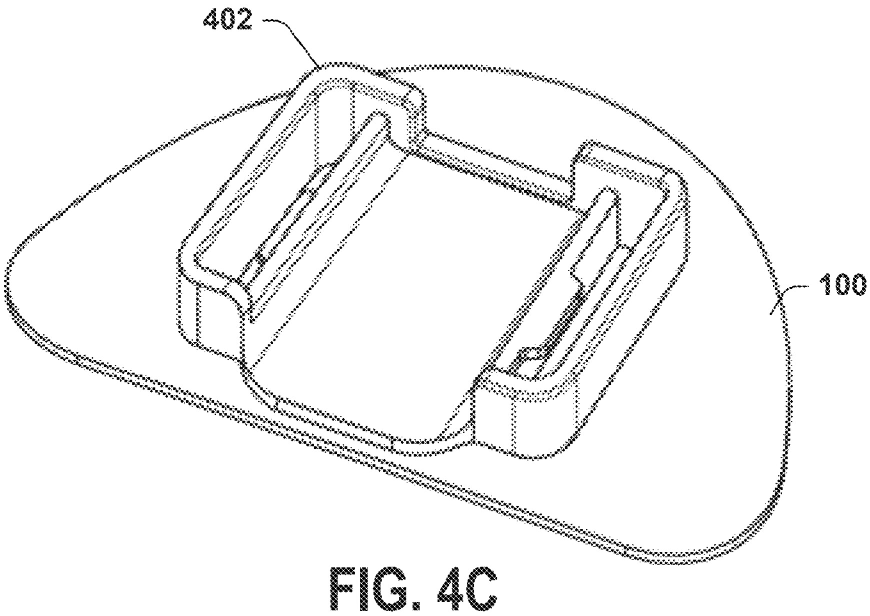
Figure 4D:
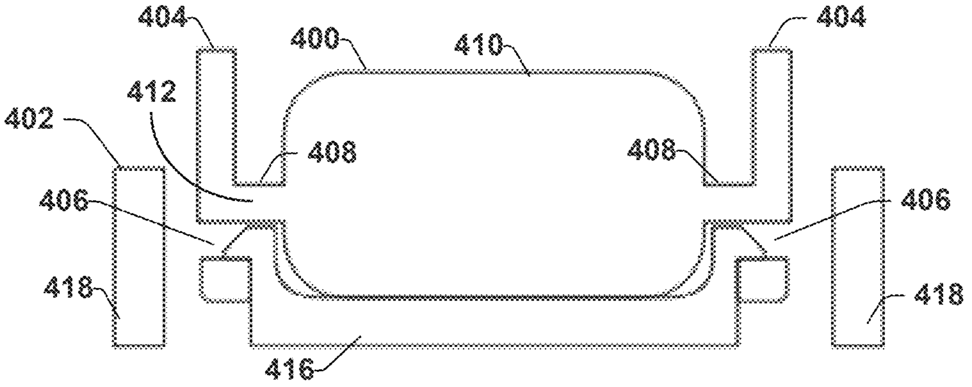
Figure 4E:
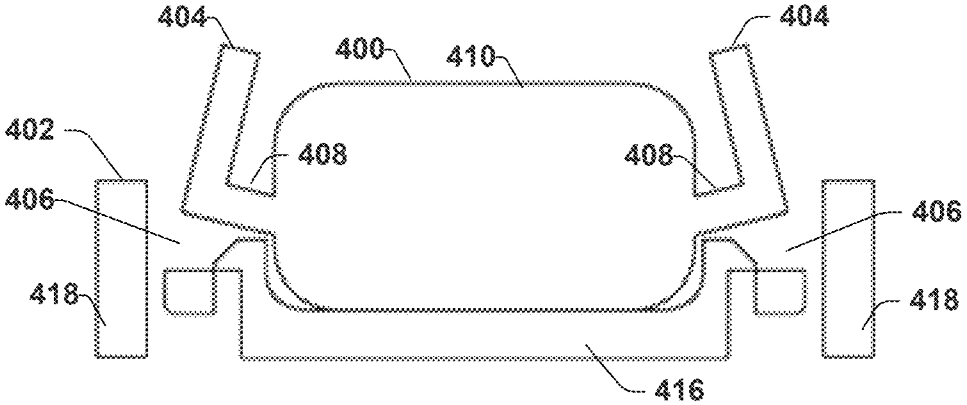

In the illustrated examples, the connector 400 detachably engages the connector base 402 by vertically aligning the connector 400 with the connector base 402 and pressing down until the connector 400 snaps into the connector base 402. The snap fit between the connector 400 and the connector base 402 via pushing down promotes securing the connector 400 without pulling on the lead 206 and prevents or inhibits the connector 400 from being dislodged during use. In the illustrated examples, the connector 400 include connection wings 404 that define connection slots 406. A connection portion 408 that bridges the connection wings 404 with a body 410 of the connector 400 is flexible or semi-ridge allowing pressure applied to the tops of the connection wings 404 to temporarily deform the connection portion 408 (e.g., as illustrated in FIG. 4E) to facilitate removing the connector 400 from the connector base 402. The connection wings 404 each define a tab slot 412 configured to lock the connector 400 into the connector base 402. In the illustrated example, because the connector 400 includes an integrated cable, one of the connection wings 404 defines a cable slot 414 to accommodate the cable 206.

The connector base 402 includes a body 416 configured to accept the body 410 of the connector 400. The connector base 402 also includes guard walls 418 that each at least partially surround snap tabs 420 (sometimes referred to as "catchments") that are configured to snap into the tab slots 406 of the connector 400 to snap the connector 400 into the connector base 402.

FIGS. 5A and 5B illustrate a molded connector base 500 configured to receive a connector (e.g., any of the connectors described herein). In the illustrated example, the connector base 500 is a molded silicone pad in which the connector 204 and lead press fits into. In the illustrated example, the connector base 500 defines a lead channel 502 configured to receive the lead (e.g., the lead 206 of FIG. 2, etc.) such that when a bandage or transparent dressing is removed, the lead is protected from being removed and/or dislodged. In the illustrated example, the connector base 500 defines a cavity 506 configures to snap or friction fit the connector such that when the bandage or transparent dressing is removed, the cable is protected from being removed and/or dislodged. In some examples, the molded connector base 500 defines a cable channel 508 configured to receive a cable (e.g., the cable 204 of FIG. 2, etc.) such that when the bandage or transparent dressing is removed, the cable is protected from being removed and/or dislodged. In some examples, the connector base 500 may have an adhesive layer (not shown) on the bottom to adhere the connector base 500 to the skin of the patient. In such examples, the connector base 500 may include a tab 510 that does not have adhesive to facilitate removing the connector base 500.

Figure 6B:
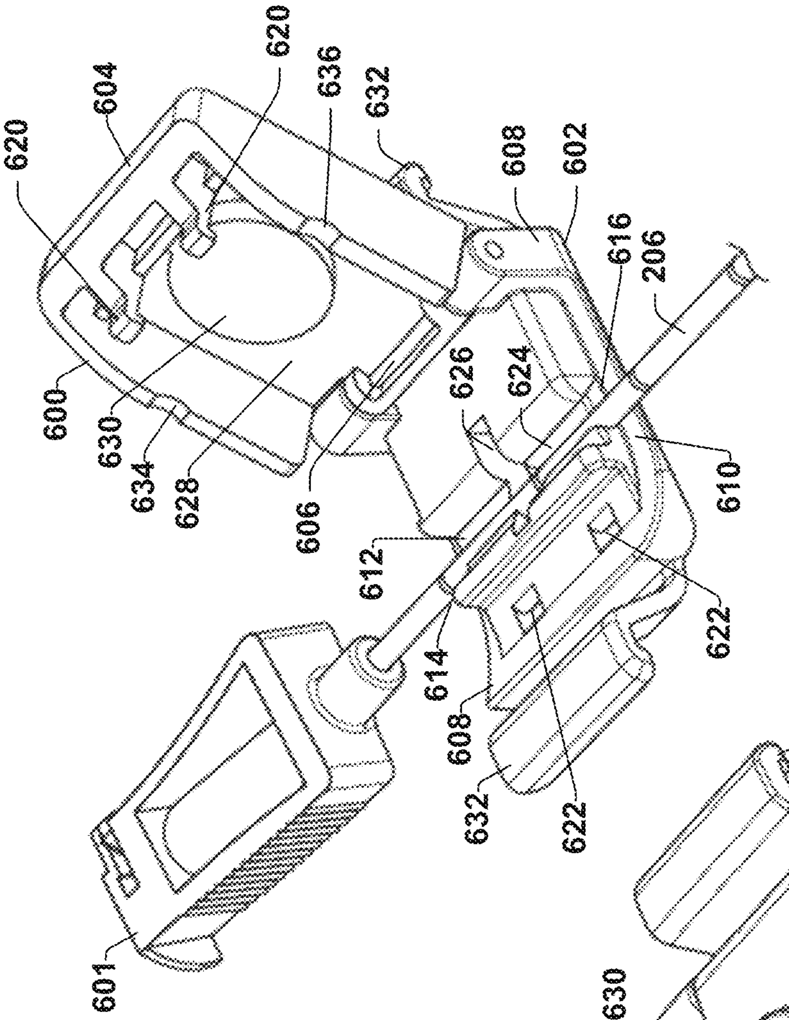
Figure 6A:
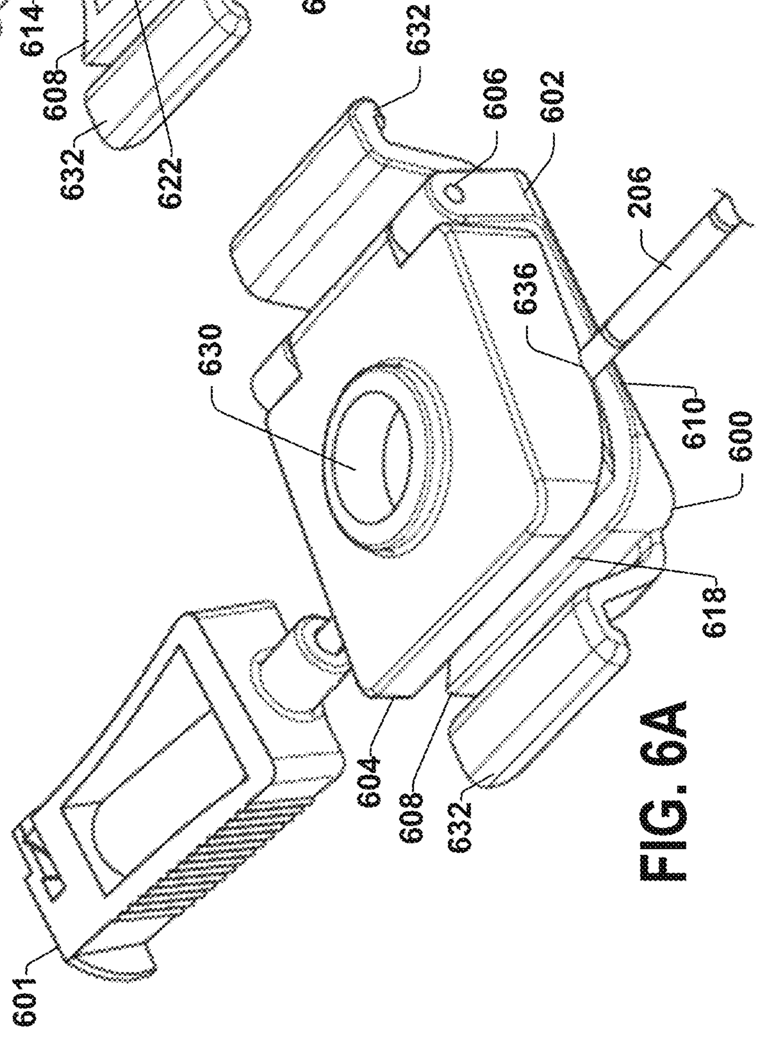
Figure 6D:
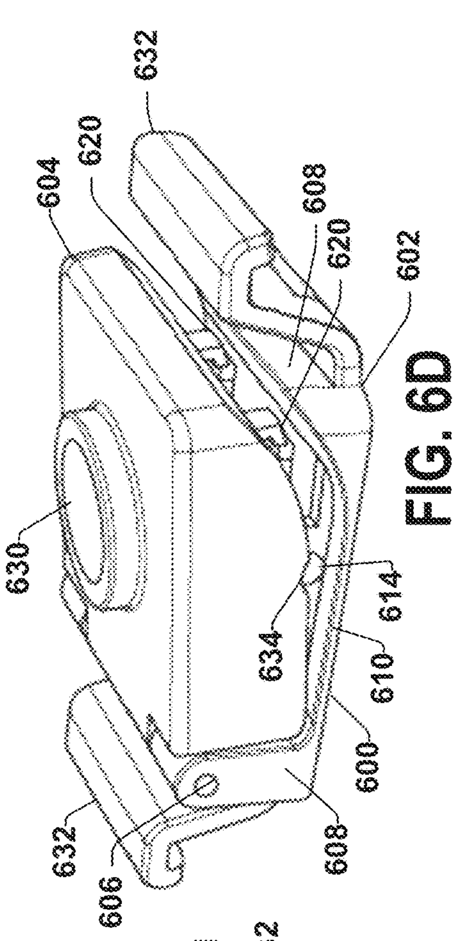
Figure 6F:
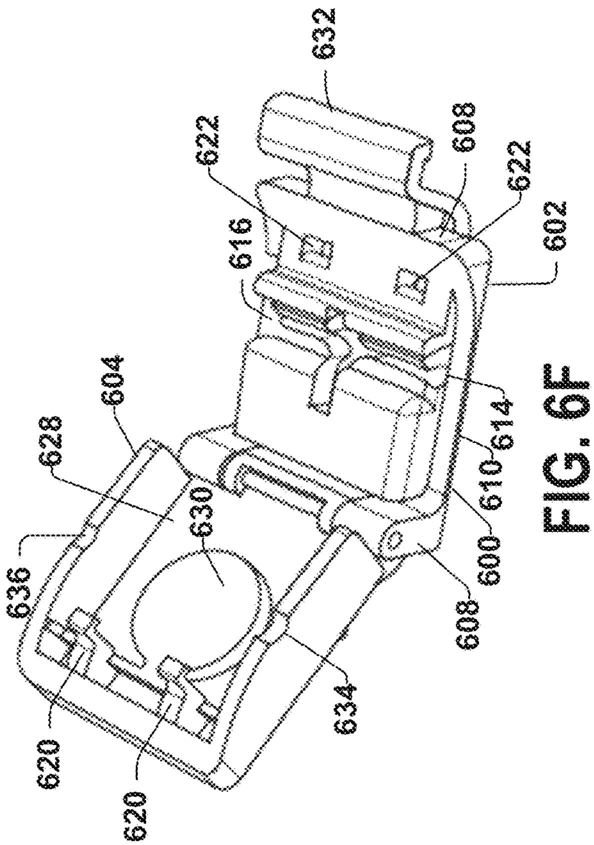
Figure 6C:
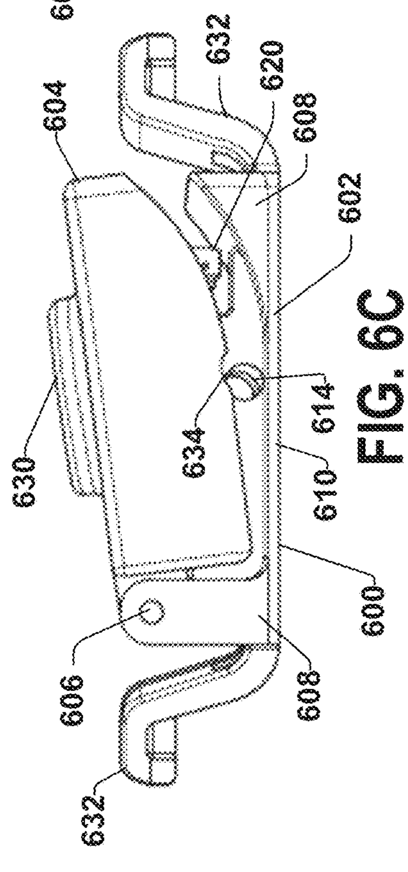
Figure 6E:
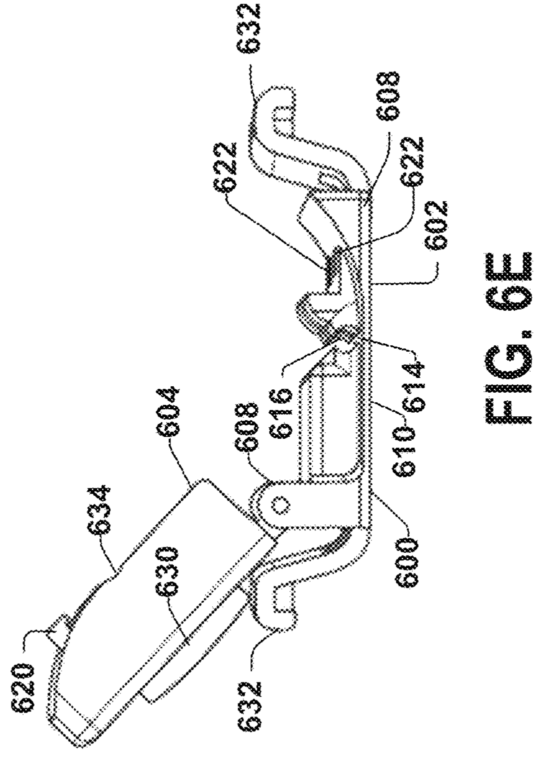
Figure 7A:
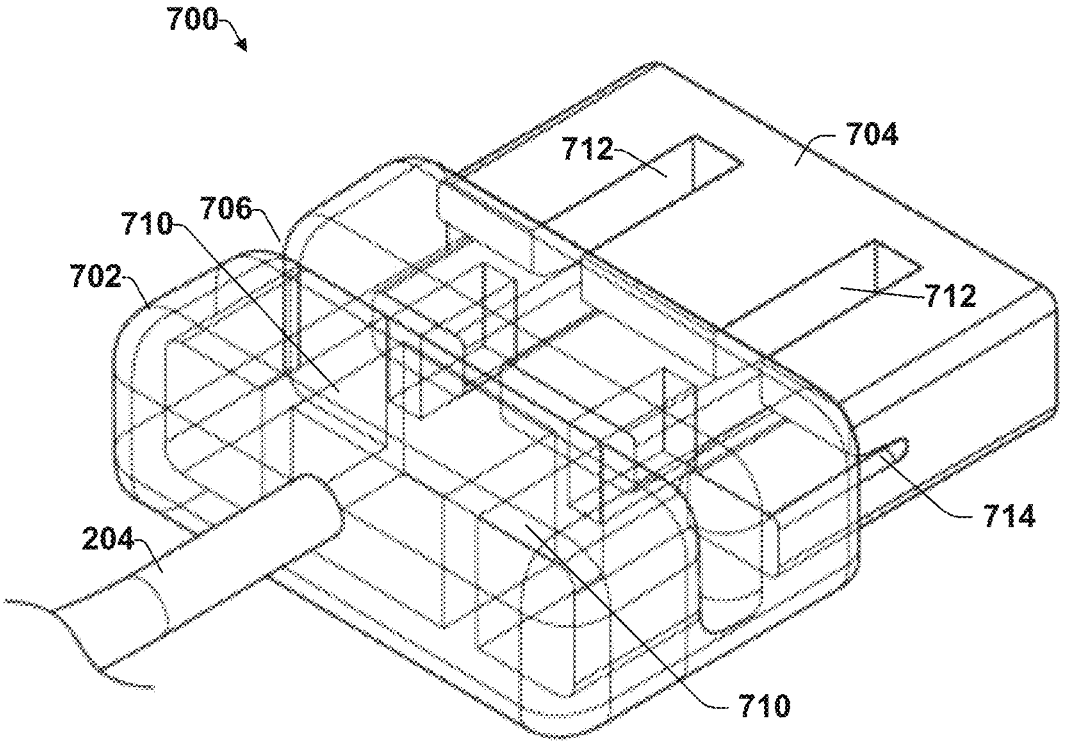
Figure 7B:
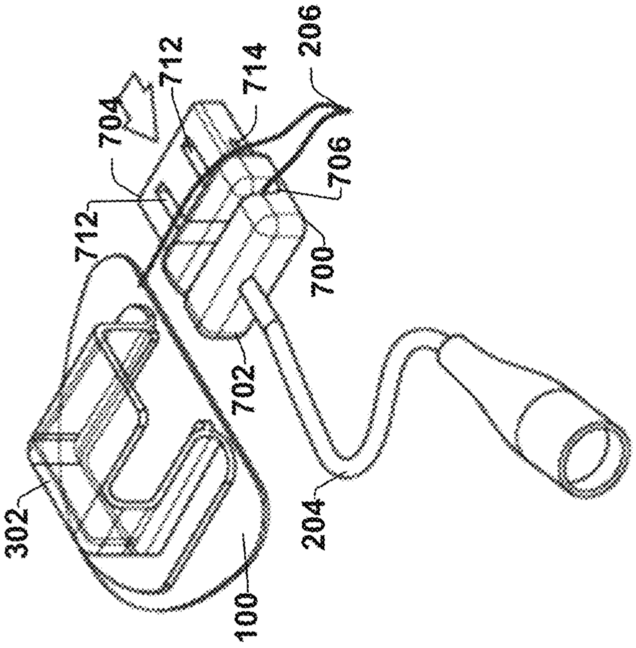
Figure 7C:
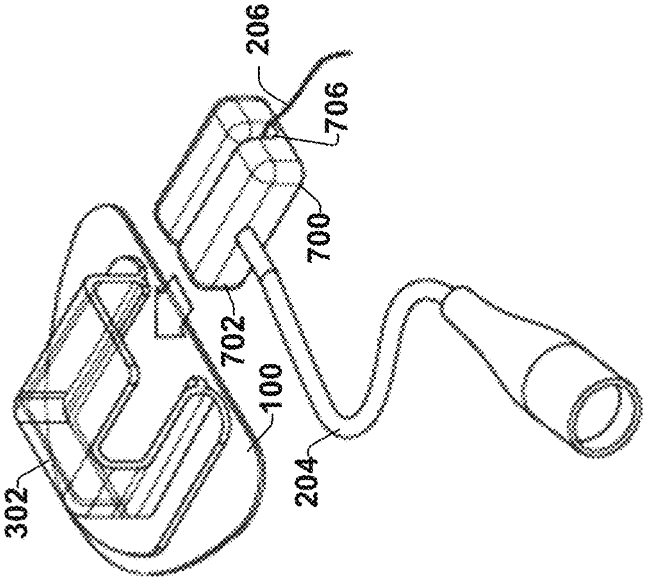
Figure 7D:
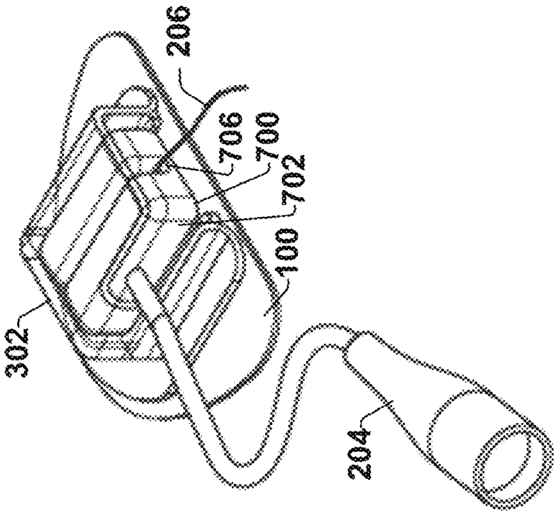

FIGS. 6A, 6B, 6C, 6D, 6E and 6F illustrate an example connector 600 with configured to mate with a detachable cable. While an example mating interface is illustrated in FIGS. 6A, 6B, 6C, 6D, 6E and 6F, the example connector 600 may use any of the connector ports (sometimes referred to as "mating interfaces") described herein. The illustrated examples general describe an example of the form of a connector. FIGS. 6A and 6B also illustrate a lead anchor 601. The lead anchor 601 may be any of the lead anchors discussed herein. The lead anchor 601 secures the lead 206 at or near the installation site to prevent or inhibit movement of the lead 206. The connector 600 provides a connection point such that the cable 204 may be attached and detached with minimal movements of the lead 206. As with other connectors described herein, the connector 600 may be molded or formed from thermosetting polymers (e.g., ABS). In some examples, the material selected is dielectric, strong enough to remain fastened to the ancillary components, and capable of being sterilized.

In the illustrated examples, the connector 600 includes a base 602 and a cover 604. The base 602 and the cover 604 are rotatably connected via a hinge or axle 606. In the illustrated example, the base 602 and the cover 604 are rotatably connected along a longer side such that the axis of rotation is substantially parallel to the lead 206 when the lead 206 is inserted into the connector 600. The base includes a plurality of sidewalls 608 and a bottom panel 610. When the cover 604 is fitted in place, an internal cavity 612 is formed. The lead 206 is received into cavity 612 by way of ports 614 and 616. When the cover 604 is closed, a space 618 may be defined between the base 602 and a cover 604 to facilitate releasing the locking clamps 620 formed on the cover 604 from their cooperating catchments 622 defined by the base 602.

The body 602 defines a lead cavity 624 between the ports 614 and 616 to receive the lead 206. In operation, the lead 206 is places within the lead cavity 624, extending beyond at least one of the ports 614 and 616. The body 602 defines a blade cavity 626 perpendicular to the lead cavity 624 to receive one or more blades (not shown) affixed to an underside 628 of the cover 604 at a cable port 630. While, for simplicity, the blades are not shown, example blades are described in International Application No. PCT/US2019/046855 entitled "Electrical Stimulator for Peripheral Stimulation," filed Feb. 12, 2021, which is incorporated by reference in its entirety. The blades are electrically coupled to the cable port 630. When a cable (e.g., cable 204) is connected to the cable port 630 and the cover 604 is closed, the cable is electrically coupled to the lead 206 via the cable port 630 and the blades.

In the illustrated example, body 602 includes connection wings 632. The connection wings 632 are an example of the connection wings 404 of FIGS. However, in other examples, the connector 600 may be configured to operate with a different type of connector base, such as the slide connector bases of FIG. 2 or FIGS. 3A, 3B, and 3C, or the molded connector base of FIGS. 5A and 5B.

The cover 604 has a generally flat, planar shape. The cover 604 includes the cable port 630. The cable port 630 may be any of the cable ports described herein. The cover 604 integrally forms the locking clamps 620 to facilitate securing the cover 604 to the base 602. In the illustrated examples, the cover defines ports 634 and 636 that correspond to and align with the ports 614 and 616. Then the cover 604 is closed, at least a portion of the lead 206 is situated within the ports 634 and 636 to provide, for example, a secure hold on the lead 206. Each locking clamp 620 includes a catchment edge at a distal end of a ramp. The catchment edge snap-fits onto catchment 622, while ramp provides a resting position on the catchment 622 to provide, for example, a closed but not locked configuration.

FIGS. 7A, 7B, 7C, and 7D illustrate an example push lock connector 700. In the illustrated examples, the push lock connector 700 is configured to cooperate with a slidably engageable connector base, such as the connector base 302 of FIGS. 3A, 3B, and 3C. However, the push lock connector 700 may be configured to be compatible with any of the connector bases described herein. The push lock connector 700 includes a body 702 and an insert 704. The push lock connector 700 has an open position and a closed position determined by the relative location of the inset 704 relative the body 702. In the illustrated examples of FIGS. 7A and 7B, the push lock connector 700 is in the open position with the insert 704 not inside the body 702 to lock the lead 206. In the illustrated examples of FIGS. 7C and 7D, the push lock connector 700 is in the closed position with the insert 704 inside the body 702 to lock the lead 206.

In the illustrated example, the cable 204 is incorporated into the body 702. However, the body 702 may be configured with any of the mating interfaces described herein. The body 702 defines a lead channel 706 that accepts the lead 206. The body 702 also defines an interior cavity 708 having guiding tabs 710 configured to interface with corresponding guiding channels 712 of the insert 704 to facilitate insertion of the insert 704 into the body 702. The body 702 includes one or more blades (not shown) that are electrically coupled to the cable 204. When the push lock connector 700 is in the closed position, the blades are mechanically and electrically coupled to the lead 206 within the lead channel 706 to provide an electrical connection between the cable 204 and the lead 206.

The insert 704 defines the guiding channels 712 and lead ports 714. The guiding channels 712 cooperate with the guiding tabs 710 of the body 702 to facilitate insertion of the insert 704 into the body 702. When the insert 704 is inserted into the body 702, the lead ports 714 accept the lead 206 that is positioned in the lead channel 706 of the body 702. When the insert 704 is substantially inserted into the body 702 and the connector 700 is in the closed position, end walls 716 of the lead ports 714 entourage the lead 206 against the blades and lock the lead 206 into the connector 700. Thus, when the lead 206 is in the lead channel 706 and the insert 704 is substantially inserted into the body 702, the lead 206 is secured in the body 702 and is electrically coupled to the cable 204.

FIGS. 8A, 8B, and 8C illustrate an example folding lead anchor 800 to secure the lead 206 to the patient to prevent or inhibit the lead 206 from moving at the installation site. In the illustrated examples of FIGS. 8A and 8B, the lead 206 is coupled to a connector 800 that is attached to a connector base 802. The connector base 802 is affixed to the patient via the adhesive pad 100 of FIG. 1. In the illustrated examples, the folding lead anchor 800 is configured to be affixed to the patient via sutures 804.

The folding lead anchor 800 includes a first side member 806A and a second side member 806B (collectively referred to as "side members 806") connected at a connection point 808. The folding lead anchor 800 is flexible enough such that inner surfaces 810A and 810B of the respective side member 806 may come in contact when the folding lead anchor 800 is folded at the connection point 808. The folding lead anchor 800 defines a lead channel 812 between the side members 806 configured to accept the lead 206. The lead 206 is gripped in the lead channel 812 then the folding lead anchor 800 is folded by gripping members 814 attached to one or more of the side members 806 in the lead channel 812. The side members 806 define suture holes 816 configured to be used to suture the folding lead anchor 800 to the patient when the folding lead anchor 800 is folded about the lead 206. The illustrated example of FIG. 8C illustrated two aligning sets of the suture holes 816, each set having two suture holes 816. However, in some examples, the side members 806 may define more than two suture holes 816. When installed, the side members 806 are folded with the lead 206 in the lead channel 812 such that the inner surfaces 810A and 810B touch and the suture holes 816 of the first side member 806A align with the suture holes 816 of the second side member 806B.

FIGS. 9A and 9B illustrate an example snapping lead anchor 900 to secure the lead 206 to the patient to prevent or inhibit the lead 206 from moving at the installation site. The snapping lead anchor 900 may be used in conjunction with any of the connectors described herein. FIG. 9A illustrated the snapping lead anchor 900 in an open position. FIG. 9B illustrated the snapping lead anchor 900 in a closed position. In the illustrated examples, the snapping lead anchor 900 includes a first side member 902, a second side member 904, and a connection member 906.

The side members 902 and 904 are configured to be placed directly or indirectly on a patient and be sutured to the patient. The side members 902 and 904 define suture holes 908 to facilitate suturing the snapping lead anchor 900 to the patient. In the illustrated example, a portion 910 of side members 902 and 904 slope towards and attach to the connection member 906 to facilitate, for example, opening and closing of the connection member 906.

The connection member 906 receives the lead 206 and prevents or inhibits movement of the lead 206 when the connection member 906 is closed. The connection member 906 defines a first arm 912 and a second arm 914. The first arm 912 and the second arm 914 are affixed at a flexible joint 916. The first arm 912 and the second arm 914, at the flexible joint 916, define a lead channel 918 to accept the lead 206 when the snapping lead anchor 900 is open. When the snapping lead anchor 900 is closed, the first arm 912 and the second arm 914 together grip the lead 206 to inhibit movement of a portion of the lead 206 that is within the connection member 906. In the illustrated example, to lock the connection member 906 in the closed position, the first arm 912 includes a locking clamps 920, and the second arm 914 defines a cooperating catchment 922. When the first arm 912 and the second arm 914 are pressed together, the locking clamp 920 inserts and locks into the cooperating catchment 922. To unlock the connection member 906 the locking clamp 920 may be deformed enough to release from the cooperating catchment 922.

FIGS. 10A, 10B, 10C and 10D illustrate an example folding lead anchor 1000 to secure the lead 206 to the patient to prevent or inhibit the lead 206 from moving at the installation site. The folding lead anchor 1000 may be used in conjunction with any of the connectors described herein. The illustrated example, the folding lead anchor 1000 includes a base 1002 and an arm 1004 flexibly connected to the base 1002. Together, the base 1002 and the arm 1004 define a lead channel 1006 to accept the lead 206.

The base 1002 includes a guiding tab 1008 and defines suture holes 1010 configured to receives sutures to affix the folding lead anchor 1000 to the patient. The lead channel 1006 is configured to accept the guiding tab 1008. This aligns the suture holes 1014 that with at least a portion of the suture holes 1010 of the base 1002. When installed, the lead 206 is inserted into the lead channel 1006, the arm 1004 is deformed such that the guiding tab 1008 is inserted into the lead channel 1006, and sutures are used in conjunction with the suture holes 1010 and 1014.

FIGS. 11A and 11B illustrate an example adhesive-based lead anchor 1100 to secure the lead 206 to the patient to prevent or inhibit the lead 206 from moving at the installation site. The adhesive-based lead anchor 1100 may be used in conjunction with any of the connectors described herein. In the illustrated example, the adhesive-based lead anchor 1100 comprises a collar 1102 that is adhered to the lead 206. The collar 1102 includes a flat portion 1104 that is a fixation point (e.g., as shown in FIG. 11B) for a bandage 1104, such as a steri-strip style bandage. The collar 1102 may be clamped onto the lead 206.

FIGS. 12A and 12B illustrate an adhesive-based lead anchor 1200 to secure the lead 206 to the patient to prevent or inhibit the lead 206 from moving at the installation site. The adhesive-based lead anchor 1200 may be used in conjunction with any of the connectors described herein. A body 1202 of the lead anchor 1200 is generally planar. The body 1202 defines a lead channel 1204 to accept the lead 206. The lead channel 1204 may be configured to provide a friction fit for the lead 206. To prevent movement of the lead anchor 1200, the surface of the body 1202 is configured to receive a bandage that adheres to the body 1202 and to the patient as illustrated in FIG. 12B.

FIG. 13 illustrates an example dual purpose lead anchor 1300 to secure the lead 206 to the patient to prevent or inhibit the lead 206 from moving at the installation site. The dual purpose lead anchor 1300 may be used in conjunction with any of the connectors described herein. A body 1302 of the dual purpose lead anchor 1300 is generally planar. The body 1302 defines a lead channel 1304 to accept the lead 206. The lead channel 1304 may be configured to provide a friction fit for the lead 206. To prevent movement of the dual purpose lead anchor 1300, the surface of the body 1302 is configured to receive a bandage that adheres to the body 1302. The body 1302 also defines suture holes 1306. The suture holes 1306 may be used to suture the dual purpose lead anchor 1300 to the patient. In some examples, the dual purpose lead anchor 1300 may be affixed to the patient using only a bandage. In some examples, the dual purpose lead anchor 1300 may be affixed to the patient using only sutures. In some examples, the dual purpose lead anchor 1300 may be affixed to the patient using both sutures and a bandage.

FIG. 14 illustrates an example protective cover 1400 to protect a connector 1402, a connector base 1404, and a lead (not shown) when the lead is installed. In some examples, the protective cover 1400 is a thermoformed plastic cover that sits between the components (e.g., the connector 1402, the connector base 1404, and the lead, etc.) and a bandage to prevent the components from lifting when the bandage is replaced. In the illustrated example, the protective cover 1400 includes a body 1406 and a foot 1408. The body 1406 includes a side wall 1410 and a top wall 1412. The side wall 1410 and the top wall 1412 form a cavity in which the connector 1402, connector base 1404, and lead are located when the protective cover 1400 is installed. The foot 1408 is generally planar and extends from the side wall 1410 of the body 1406. In the illustrated examples, the foot 1408 defines a cable channel 1414 that provides a passage from the cavity to accommodate the cable 204 connected to the connector 1402. When installed, the protective cover 1400 may be adhered to the patient via a bandage, such as a TEGADERM bandage, that covers the body 1406, the foot 1408, a portion of the cable 204 extending from the cable channel 1414 and a region of the patient around the protective cover 1400.

FIGS. 15A and 15B illustrate an example of a protective cover 1500 to protect a connector 1502, a connector base 1504, and a lead (not shown) when the lead is installed. The protective cover 1500 is a thermoformed plastic cover that sits between the components (e.g., the connector 15402, the connector base 1504, and the lead, etc.) and a bandage 1505 to prevent the components from lifting when the bandage 1505 is replaced. In the illustrated example, the protective cover 1500 includes a body 1506 and a foot 1508. The body 1506 includes a side wall 1510 and a top wall 1512. The side wall 1510 and the top wall 1512 form a cavity in which the connector 1502, connector base 1504, and lead are located when the protective cover 1500 is installed. The foot 1508 is generally planar and extends from the side wall 1510 of the body 1506. In the illustrated examples, the side wall 1510 includes a channel wall 1514 extending from the side wall 1510. The channel wall 1514 defines a cable channel 1516 that provides a passage from the cavity to accommodate the cable 204 connected to the connector 1502. In the illustrated example, the foot 1508 does not extend from the sidewall 1510 at the location corresponding to the cable channel 1514. When installed, the protective cover 1500 may be adhered to the patient via a bandage, such as a TEGADERM bandage, that covers the body 1506, the foot 1508, a portion of the cable 204 extending from the cable channel 1516 and a region of the patient around the protective cover 1500.

FIG. 16A illustrates an exploded view of a protective cover 1600 configured such that a cable 1602 remains outside of the protective cover 1600. While FIG. 16A illustrates a particular detachable cable (see FIGS. 21A, 21B, 21C, and 21D below), the protective cover 1600 may be used with any detachable cable and corresponding connector described herein. The protective cover 1600 protects a connector 1604, a connector base 1606, and a lead (not shown) when the lead is installed. The protective cover 1600 is a thermoformed plastic cover that sits between the components (e.g., the connector 1604, the connector base 1606, and the lead, etc.) and a bandage to prevent the components from lifting when the bandage is replaced. Additionally, the protective cover 1600 facilitates connecting and disconnecting the cable 1602 without removing the bandage or the protective cover 1600.

In the illustrated example, the protective cover 1600 includes a body 1608 and a foot 1610. The body 1608 includes a side wall 1612 and a top wall 1614. The side wall 1612 and the top wall 1614 form a cavity in which the connector 1604, connector base 1606, and lead are located when the protective cover 1600 is installed. The foot 1610 is generally planar and extends from the side wall 1612 of the body 1608. In the illustrated example, the foot 1610 includes tabs to, for example, reduce amount of material used to form the foot 1610.

The top wall 1614 defines holes 1616 and a port hole 1618. In the illustrated example, a disk 1620 is placed with in the port hole 1618. The disk 1620 is made of a material different from the body 1608 that resists being adhered to by the bandage. The disk 1620 defines a connector hole 1622 to facilitate the cable 1602 connecting to the connector 1604 through the protective cover 1600. When installed, the protective cover 1600 may be adhered to the patient via a bandage, such as a TEGADERM bandage.

FIG. 16B protective cover 1624 configured such that a cable 1602 remains outside of the protective cover 1624. The protective cover 1624 includes a body 1608 and a foot 1610. The body 1608 includes a side wall 1612 and a top wall 1626. The side wall 1612 and the top wall 1626 form a cavity in which the connector (e.g., connector 1604), the connector base (e.g., connector base 1606), and lead are located when the protective cover 1624 is installed. The foot 1610 is generally planar and extends from the side wall 1612 of the body 1608. In the illustrated example, the foot 1610 includes tabs to, for example, reduce amount of material used to form the foot 1610.

The top wall 1626 includes dots 1628 that comprise a conductive material. The bottom side of the dots 1628 is conductive. The tope wall 1626 and the dots 1628 are configures such that there is not any electrical conduction on a surface that a user can touch. The only conductive area is in a single axis (i.e., the z-axis immediately below the head of the connector. The top of the dots 1628 is not conductive. This configuration allows more flexibility for the clinician. Once the lead is inserted, the protective cover 1624 facilitates being placed in a variety of locations while still being able to be electrically connected. Any of the dots 1628 can be used to create the electrical connection.

FIGS. 17A, 17B, 17C, and 17D illustrate a cable 1700 with a magnetic head 1702 (sometimes referred to as a “magnetic breakaway head”) and a connector 1704 with a corresponding magnetic cradle 1706. The connector 1704 may be, for example, an example of the connector 600 of FIGS. 6A, 6B, 6C, 6D, 6E, and 6F wherein the cable port 630 comprises the magnetic cradle 1706. The magnetic cradle 1706 includes a magnet ring 1708 that interfaces with a corresponding magnet ring 1710 of the magnetic head 1702. The cable 1700 is detachably coupleable to the connector 1704. When the cable 1700 is attached to the connector 1704, the attraction of the magnet rings 1708 and 1710 affix the cable 1700 to the connector 1704. The magnetic head 1702 includes an electrically conductive pin 1712. When the cable 1700 is attached to the connector 1704, the pin 1712 pierces the bandage 1714 and inserted into a jack 1716 of the magnetic cradle 1706 to electrically couple the cable 1700 to the connector 1704. The magnetic cradle 1706 is electrically coupled to the blade(s) of the connector 1704. Thus, when the cover of the connector 1704 is closed and magnetic head 1702 is affixed to the magnetic cradle 1706, the cable 1700 is electrically coupled to the lead 206 attached to the connector 1704.

FIGS. 18A and 18B illustrate the cable 1700 with the magnetic head 1702 and the connector 1704 with a corresponding magnetic cradle 1706 of FIGS. 17A, 17B, 17C, and 17D being used in conjunction with, for example, the protective cover 1600 of FIG. 16A. In the illustrated example, the pin 1712 of the magnetic head 1702 pierces the bandage 1714 and extends through the connector hole 1622 to plug into the jack 1716 of the magnetic cradle 1706 to electrically couple the cable 1700 to the connector 1704. In such a manner, the cable 1700 can be removed and/or switched without disturbing the connector 1704 and the lead 206. In the illustrated example, to, for example, reduce the amount of material used, the protective cover 1600 may have a raised portion 1800 molded to accommodate the connector 1704 and lowered portions 1802 elsewhere.

FIGS. 19A, 19B, and 19C illustrate the cable 1700 with the magnetic head 1702 and the connector 1704 with a corresponding magnetic cradle 1706 of FIGS. 17A, 17B, 17C, and 17D being used in conjunction with a protective cover 1900. In the illustrated example, the protective cover 1900 includes a body 1902 and a foot 1904. The body 1902 includes a side wall 1906 and a top wall 1908. The side wall 1906 and the top wall 1908 form a cavity in which the connector 1704 and lead 206 are located when the protective cover 1900 is installed. The connector 1704 may be plugged into a connector base (not shown). The foot 1904 is generally planar and extends from the side wall 1906 of the body 1902. In the illustrated example, the top wall 1908 includes a matrix of openings 1910 through which the pin 1712 of the magnetic head 1702 may extend through (e.g., piercing the bandage 1714, etc.) when the cable 1700 is connected to the connector 1704. When the protective cover 1900 is installed, the matrix 1910 is generally located above the magnetic cradle 1706. The matrix 1910 may allow, for example, flexible placement of the connector 1704 relative the protective cover 1704.

FIGS. 20A, 20B, and 20C illustrate a detachable cable 2000 with an interlocking head 2002 and a connector 2004 with a corresponding interlocking stand 2006 that defines a jack 2008. The detachable cable 2000 and the connector 2004 may be used in conjunction with, for example, the protective cover protective cover 1600 of FIG. 16A, where the interlocking stand 2006 extends through the connector hole 1622. The connector 2004 may be, for example, an example of the connector 600 of FIGS. 6A, 6B, 6C, 6D, 6E, and 6F wherein the cable port 630 comprises the interlocking stand 2006. In the illustrated example, the connector 2004 is modified to plug into a winged connector base 2010.

In the illustrated example, the interlocking stand 2006 includes an inner stand 2012 that defines the jack 2008 and an outer stand 2014. In the illustrated example, the jack 2008 includes a frustoconical portion to facilitate guiding a pin 2016 of the interlocking head 2002. The inner stand 2012 and the outer stand 2014 define a guide channel 2016.

The interlocking head 2002 includes a pin 2017 that is electrically coupled to conductive wiring of the detachable cable 2000, an inner guide 2018, and an outer wall 2020. The inner guide 2018 and the outer wall 2020 define an interlock channel 2022. The inner guide 2018 is configured to fit into the guide channel 2016 and the outer stand 2014 is configured to fit into the interlock channel 2022. In some examples, the interlocking head 2002 includes a pin guide 2024 that is configured to fit within at least a portion of the frustoconical portion of the jack 2008. When the interlocking head 2002 is plugged in the interlocking stand 2006, the pin 2016 is electrically coupled to the blades such that when the cover of the connector 2004 is closed and interlocking head 2002 is plugged in the interlocking stand 2006, the cable 2000 is electrically coupled to the lead attached to the connector 2004.

In the illustrated example, the connector base 2010 includes a base 2026, sidewalls 2028 with wings 2030. The sidewalls 2028 define catchment holes 2032. The connector 2004 includes locking members 2034 that are configured to snap fit into the catchment holes 2032. The sidewalls 2028 are deformable enough that a downward force on the wings 2030 horizontally displaces the sidewalls 2028 enough to release the locking members 2034 from the catchment holes 2032.

Figure 21A:
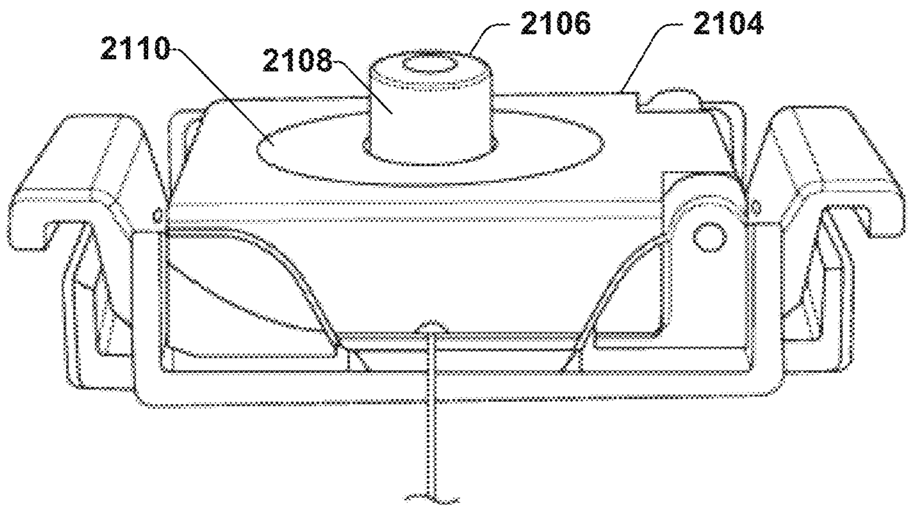
Figure 21B:
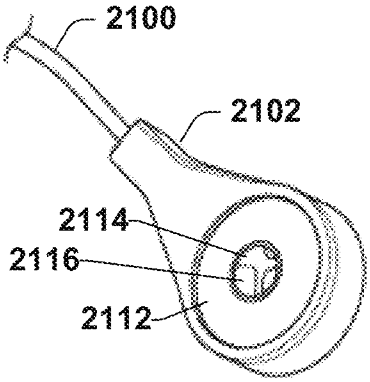
Figure 21C:
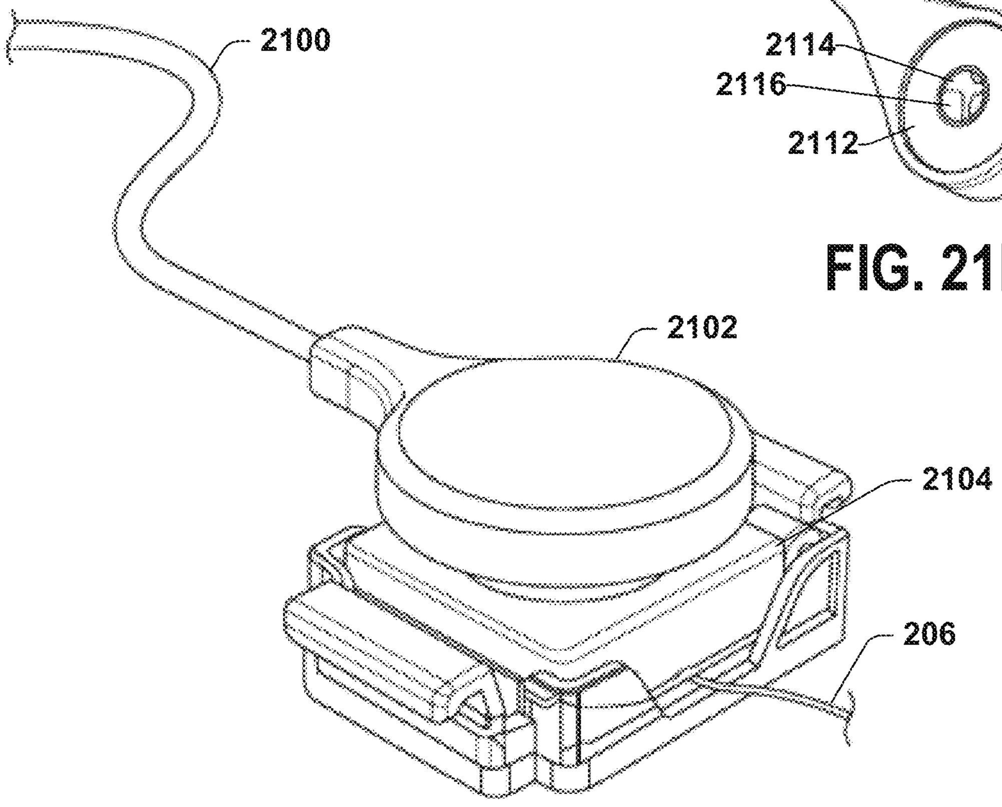
Figure 21D:
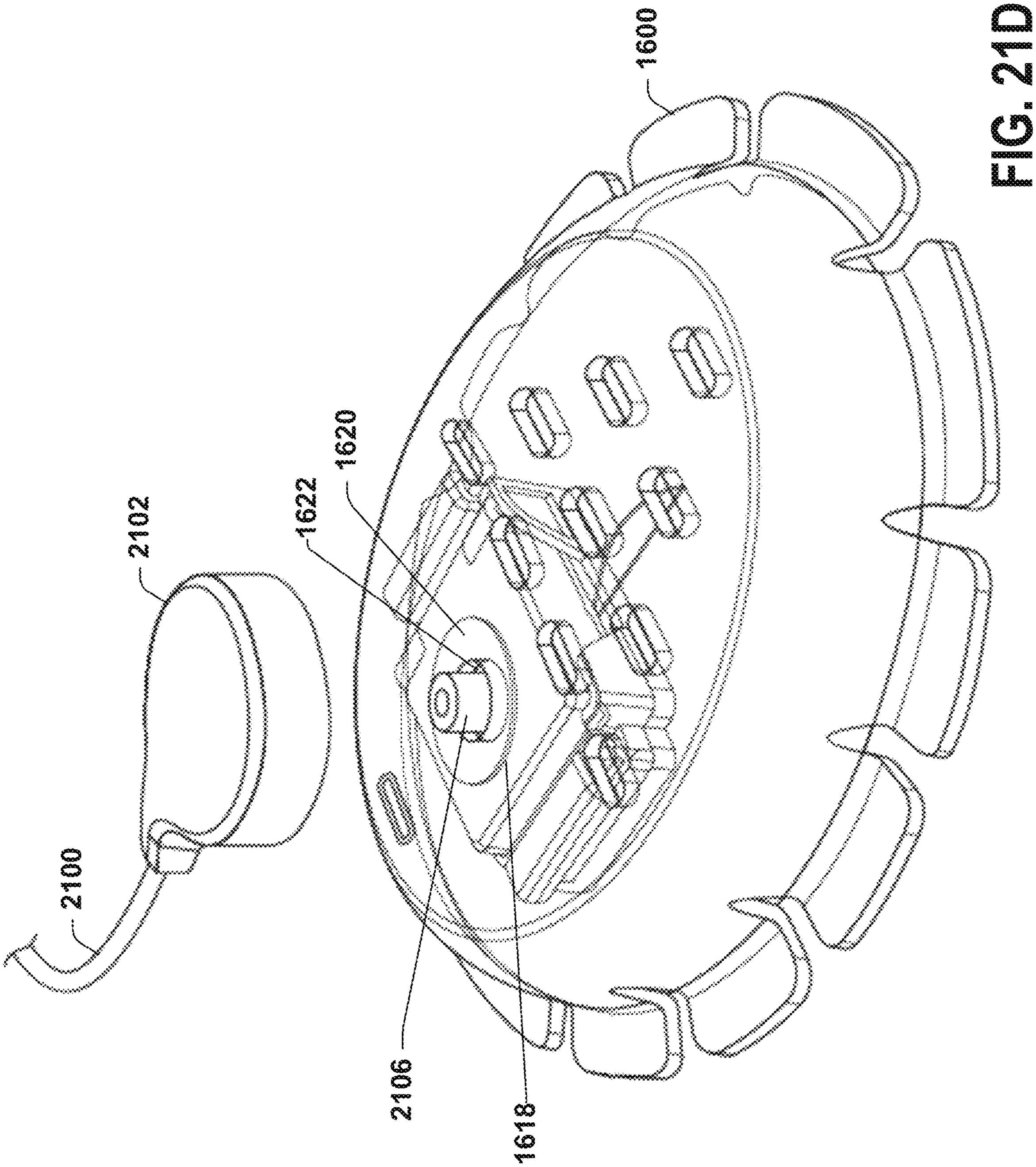

FIGS. 21A, 21B, 21C, and 21D a cable 2100 with a magnetic head 2102 (sometimes referred to as a "magnetic breakaway head") and a connector 2104 with a pin connector 2106. As shown in FIG. 21D, the cable 2100 and the connector 2104 may be used in conjunction with, for example, the protective cover protective cover 1600 of FIG. 16A, where the pin connector 2106 extends through the connector hole 1622. The connector 2004 may be, for example, an example of the connector 600 of FIGS. 6A, 6B, 6C, 6D, 6E, and 6F wherein the cable port 630 comprises the pin connector 2104.

The pin connector 2106 includes an electrically conductive pin 2108 and a magnetic ring 2110. The conductive pin 2108 is electrically coupled to the blades of the connector 2104. The magnetic head 2102 includes a magnetic ring 2112. The magnetic head 2102 also defines a socket 2114 in which conductive pads 2116 are arranged. The conductive pads 2116 are electrically coupled to the conductive wire of the cable 2100. When the cable 2100 is plugged into the connector 2104, the conductive pin 2108 enters the socket 2114 and mechanically and electrically couples with the conductive pads 2116. In some examples, the conductive pin 2108 may be an EEG safety DIN connector and the socket 2114 may be the corresponding EEG safety DIN socket. When the cable 2100 is attached to the connector 2104, the attraction of the magnet rings 2110 and 2112 affix the cable 2100 directly or indirectly to the connector 2104. When the magnetic head 2102 is plugged in the pin connector 2106 and the cover of the connector 2104 is closed, the cable 2100 is electrically coupled to the lead 206 attached to the connector 2104.

FIGS. 22A and 22B illustrate a protective cover 1600 configured to interface between a head 2200 of a cable 2202 and a cable port 2204 of a connector 2206. The connector 2206 may be, for example, an example of the connector 600 of FIGS. 6A, 6B, 6C, 6D, 6E, and 6F wherein the cable port 2204 is the cable port 630. In such an examples, the cable port 2204 include a conductive element that electrically couples walls 2208 of the cable port 2204 to the blade(s) of the connector 2206. In the illustrated example, the cable 2202 is an example of the cable 2100 of FIG. 21B.

The protective cover 1600 includes a connection element 2210 that fits within the port hole 1618. The connection element 2210 includes an electrically conductive pin 2212 and a magnetic ring 2214. The conductive pin 2212 includes a cable side 2216 and a connector side 2218. The cable side 2216 is configured to be inserted into the socket 2114 and mechanically and electrically couple with the conductive pads 2116. The connector side 2218 is configured to be inserted into the cable port 2204 to mechanically and electrically couple with the walls 2208 of the cable port 2204. The connection element 2210 may snap fit to the cable port 2204. When the cable 2100 is attached to the connection element 2210, the attraction of the magnet rings 2110 and 2214 affix the cable 2100 directly or indirectly to the connection element 2210. While in the illustrated example, the connection element 2210 has a conductive pin 2212 that includes a cable side 2216 to interface with the head 2200 of a cable 2202, the connection element 2210 may have any other suitable interface, such as an interface to mate with the magnetic head 1702 of FIGS. 17A, 17B, 17C, and 17D or the interlocking head 2002 of FIGS. 20A, 20B, and 20C, etc.

FIGS. 23A and 23B illustrate a cable 2300 and a connector 2302 with inductive interfaces 2304 and 2306. The connector 2302 may be, for example, an example of the connector 600 of FIGS. 6A, 6B, 6C, 6D, 6E, and 6F wherein the cable port 630 comprises the inductive interfaces 2306. The cable 2300 includes an inductive head 2308. The inductive head 2308 includes the inductive interface 2304 and alignment and retention magnets 2310. The connector 2302 includes alignment and retention magnets 2312 that correspond with the alignment and retention magnets 2310 of the inductive head 2308. When connected, the magnetic force of the alignment and retention magnets 2310 and 2312 affix the inductive head 2308 to the connector 2302, even when a bandage 2314 is fixed to the connector 2302 and blocking direct contact between the connector 2302 and the inductive head 2308. The inductive interface 2306 of the inductive head 2304 and the inductive interface 2306 of the connector 2302 have corresponding inductive coils that align with each other via the alignment and retention magnets 2308 and 2310. The inductive interface 2306 of the inductive head 2304 transmits signals to the inductive interface 2306 of the connector 2302. In such a matter, the cable 2300 may transmit stimulation signals to the lead 206 via the connector 2302 even then the bandage 2314 is preventing direct contact between the cable 2300 and the connector 2302.

FIG. 24 illustrates an example thin connector 2400 that incorporates a cable 2402. The thin connector 2400 snaps into a thin connector base 2404. In the illustrated example, the thin connector base 2404 is attached to the patient via the adhesive pad 100 of FIG. 1. The thin connector 2400 includes a first arm 2406 and a second arm 2408. The first arm 2406 and the second arm 2408 are flexibly coupled to allow the first arm 2406 and the second arm 2408 to open and close respective of each other. The first arm 2406 and the second arm 2408 each include ridges that define lead channels 2410 and 2412 respectively. One of the lead channels 2410 and 2412 includes a microblade (not shown) that electrically couples with the lead 206 through insulation that may be covering the conductive element of the lead 206 when the thin connector 2400 is closed. The microblade is in turn electrically coupled to the conductive element of the cable 2402. In the illustrated example, the cable 2402 is flat to site flush against the body of the patient. The conductive element of the cable 2402 may be a flexible ribbon wire.

The thin connector base 2404 includes a base 2414 and multiple catchment prongs 2416. The catchment prongs 2416 are configured to secure the thin connector 2400 to the base 2414 of the thin connector base 2404 and hold the first arm 2406 and the second arm 2408 in the closed position. The thin connector 2400 may then be further secured to the patient and the thin connector base 2404 via a bandage. The low profile of the thin connector 2400 and thin connector base 2404 may guard against dislodgement due to bumps to the patient.

FIG. 25 illustrates an example polarized connector 2500 and a polarized connector base 2502. In the illustrated example, the polarized connector base 2502 is attached to the patient via the adhesive pad 100 of FIG. 1. The polarized connector 2500 includes a body 2504, a cover 2506 rotatably connected to the body 2504, a first set of magnets with a first polarization, and a second set of magnets with the opposite polarization. In the illustrated example, a cable 2508 is integrated into the polarized connector 2500. The body 2504 defines a lead channel 2510 to accept a lead and a cover channel 2512 to accept the cover 2506 when the cover 2506 is in a closed position. The cover 2506 may snap or friction fit into the cover channel 2512. The cover 2506 includes a blade electrically coupled to the cable 2508. When the cover 2506 is in the closed position, the blade electrically couples with the lead to electrically couple the lead to the cable 2508.

The polarized connector base 2502 includes a first set of magnets 2514 with a first polarization, and a second set of magnets 2516 with the opposite polarization. The magnets of the polarized connector 2500 and the magnets 2514 and 2516 of the polarized connector base 2502 are arranged so that the polarized connector 2500 connects to the polarized connector base 2502 at a certain orientation. The polarized connector 2500 resists being pulled away from the polarized connector base 2502 with a force normal to the polarized connector base 2502, but may rotate about the normal axis to misalign the magnets to release the polarized connector 2500.

FIGS. 26A, 26B, and 26C illustrate example of a protective cover 2600 with an integrated cable head 2602. The protective cover 2600 interfaces with a detachable cable 2604. The protective cover 2600 is configured to selectively interface with a connector 2606. The connector 2606 may be any connector described herein. Additionally, the interface between the integrated cable head 2602 and the connector 2606 may be any interface described herein. In the illustrated example, the connector 2606 is selectively attachable to a connector base 2608.

In the illustrated example, a body 2610 of the integrated cable head 2602 is integrally formed with a body 2612 of the protective cover 2600. The body 2610 of the integrated cable head 2602 includes an interface portion 2614 that houses an interface 2616 that selectively connects to a corresponding interface 2618 of the connector 2606. The body 2610 of the integrated cable head 2602 also includes an interconnect portion 2620 that houses a plug 2622 that selectively receives a corresponding jack 2624 of the detachable cable 2604. The plug 2622 is electrically coupled to the interface 2616. When the jack 2624 of the detachable cable 2604 is electrically and mechanically coupled to the plug 2622, the conductive element of the detachable cable 2604 is electrically coupled to the interface 2616.

Figure 27A:
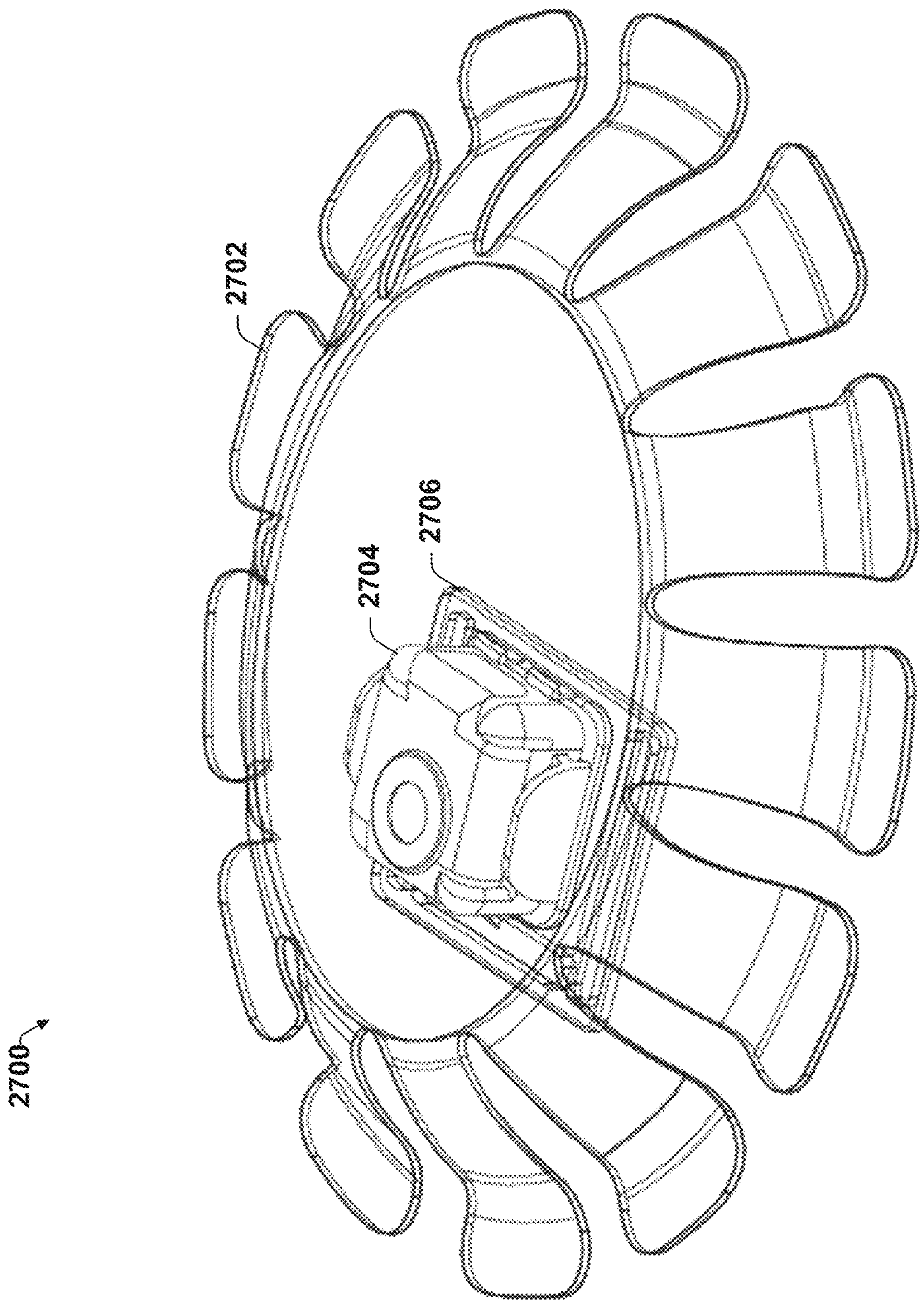
Figure 27C:
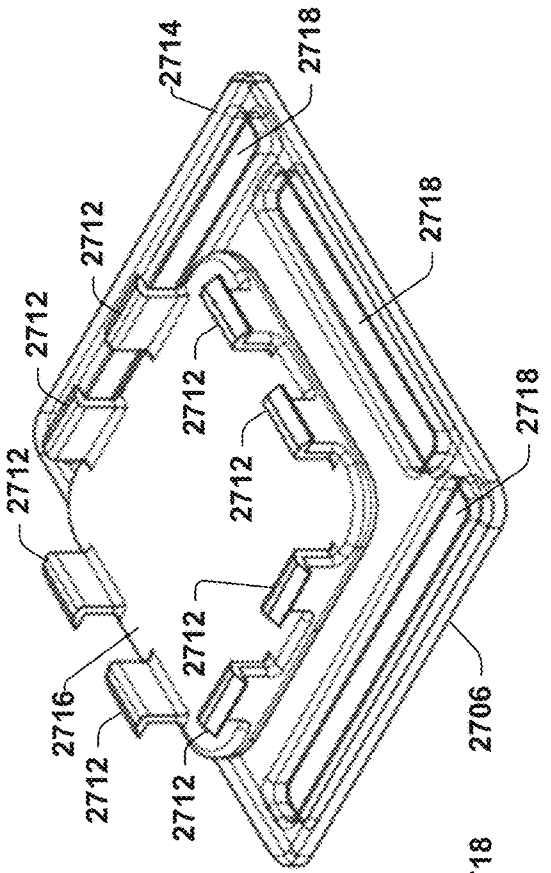
Figure 27B:
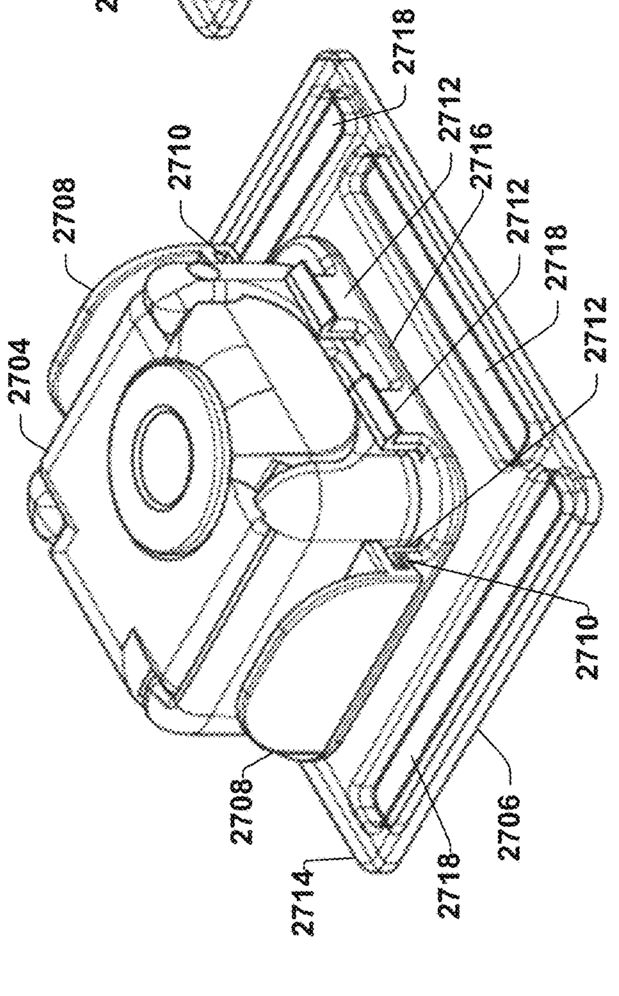
Figure 27E:
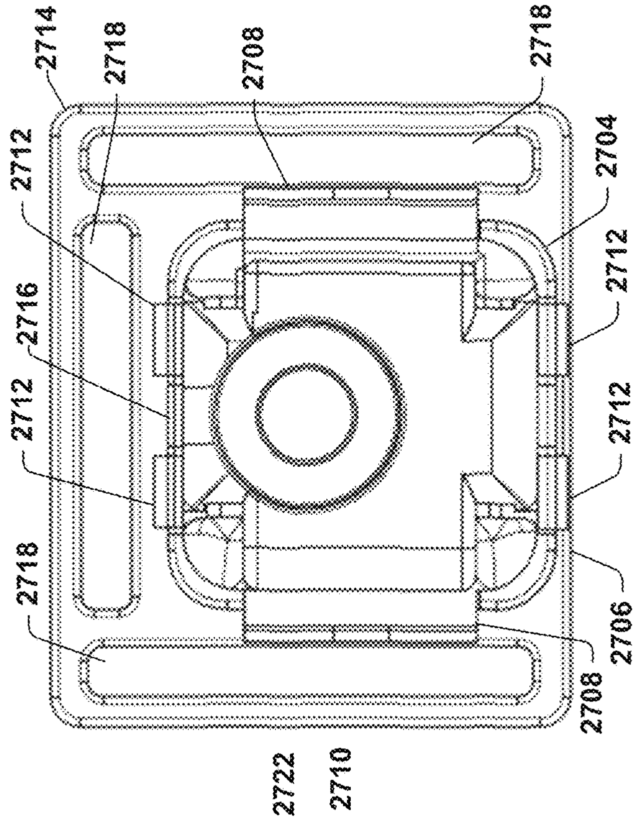
Figure 27D:
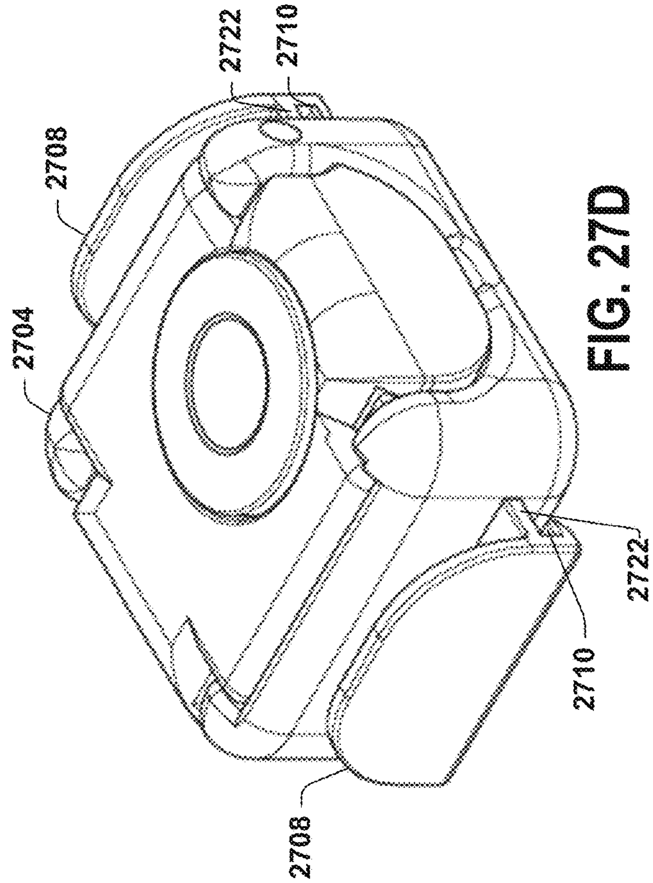
Figure 27F:
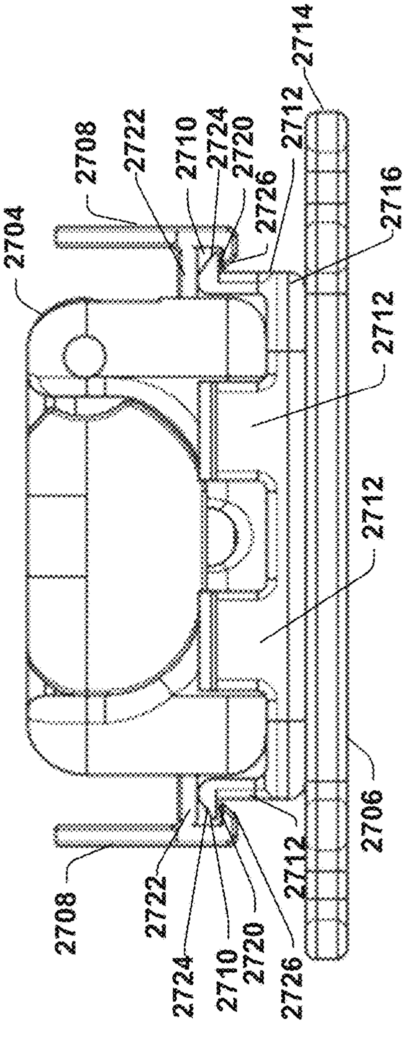
Figure 27G:
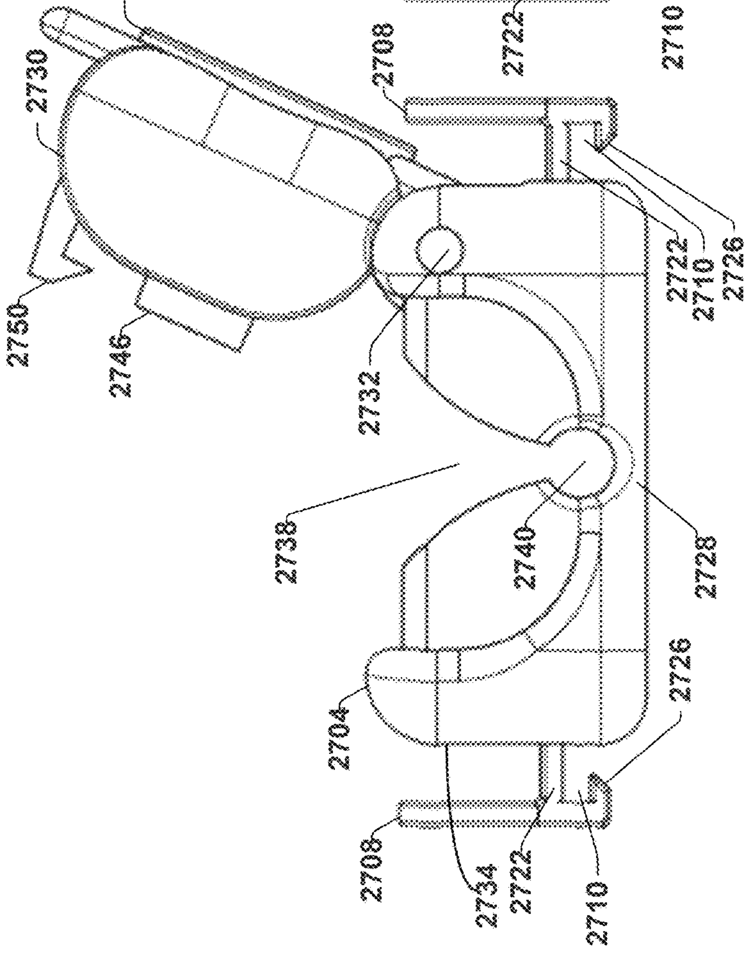
Figure 27H:
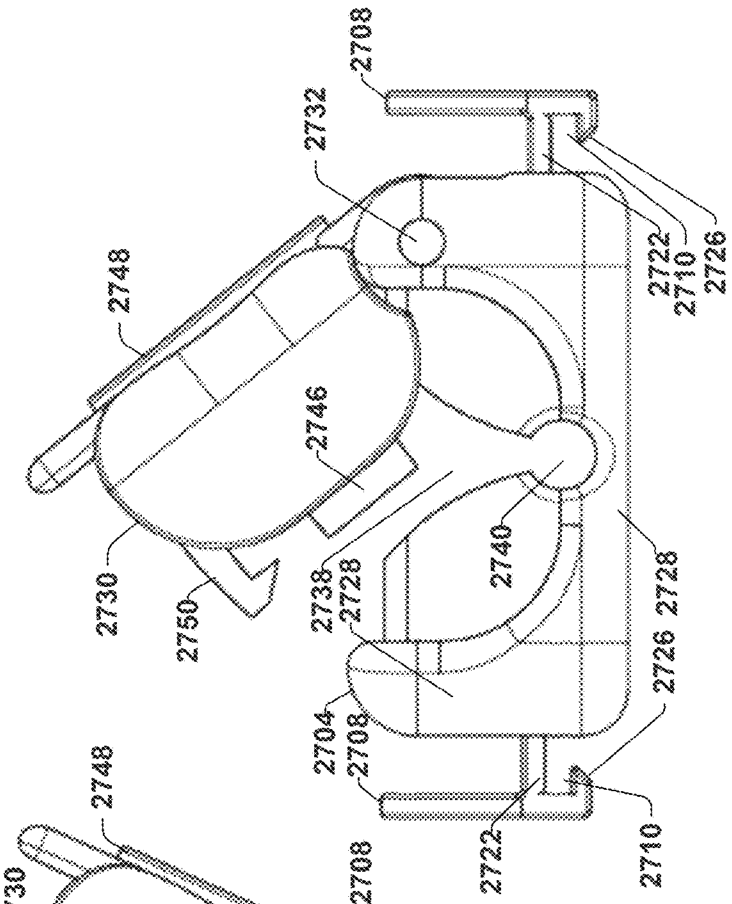

FIGS. 27A, 27B, 27C, 27D, 27E, 27F, 27G, and 27H illustrate an example stimulation lead connection system 2700. In the illustrated example, the lead connection system 2700 includes a protective cover 2702, a connector 2704, and a connector base 2706. In some examples, the lead connection system 2700 may also include a lead anchor (such as, any of the lead anchors described herein). FIG. 27B illustrated the connector 2704 selectively affixed to the connector base 2706. The connector 2704 attaches to the connector base 2706 through a vertical motion (e.g., a motion normal to a plane defined by the connector base 2706). In the illustrated examples, the connector 2704 includes wings 2708 that define catchments 2710 to receive corresponding latches 2712 of the connector base 2706. As best illustrated in FIG. 27C, the connector base 2706 includes latches 2712 that facilitate attaching the connector 2704 at different orientations, such that, when the connector 2704 is affixed, it may not be coupled to each one of the latches 2712.

In the illustrated examples, the connector base 2706 includes a base 2714 and a cradle 2716. In the illustrated example, the cradle 2716 is integrally formed with the base 2714. The base 2714 defines suture holes 2718 to facilitate suturing the connector base 2706. Alternatively, the connector base 2706 may be affixed to the patient via an adhesive pad (e.g., the adhesive pad 100 of FIG. 1, etc.). The cradle 2716 includes the latches 2712. The latches 2712 include capture edges 2720 that engage with the catchments 2710 of the connector 2704. A ramp portion 2724 of the latches 2712 promote deformation of the wings 2708 when the connector 2704 is pressed into the connector base 2706 to facilitate a snap fit of the connector 2704 into the connector base 2706.

The connector 2704 includes the wings 2708 that are connected to the connector 2704 via attachment members 2722. The attachment members 2722 is deformable enough such that inward force on the wings 2708 displaces the locations of the catchments 2710 enough to release from the capture edges 2720 of the latches 2712. In the illustrated example, the wings 2708 include a ramp edge 2726 configured to cooperate with the ramp portion 2724 of the latches 2712.

In the illustrated examples, the connector 2704 includes a base 2728 and a cover 2730. The base 2728 and the cover 2730 are rotatably connected via a hinge or axle 2732. In the illustrated example, the base 2728 and the cover 2730 are rotatably connected along a longer side such that the axis of rotation is substantially parallel to the lead 206 when the lead 206 is inserted into the connector 2704. The base 2728 includes a plurality of sidewalls 2734 and a bottom panel. When the cover 2730 is fitted in place, an internal cavity 2738 is formed. The lead 206 is received into cavity 2738 by way of ports 2740.

The base 2728 defines a lead cavity between the ports 2740 to receive the lead 206. In operation, the lead 206 is placed within the lead cavity, extending beyond at least one of the ports 2740. The base 2728 defines a blade cavity perpendicular to the lead cavity to receive one or more blades 2746 affixed to an underside of the cover 2730 at a cable port 2748. The blades 2746 are electrically coupled to the cable port 2748. When a cable (e.g., cable 204) is connected to the cable port 2748 and the cover 2730 is closed, the cable is electrically coupled to the lead 206 via the cable port 2748 and the blades 2746.

The cover 2730 has a generally flat, planar shape. The cover 2730 includes the cable port 2748. The cable port 2748 may include any of the cable interfaces described herein, such as the magnetic cradle 1706, the interlocking stand 2006, or the pin connector 2106, etc. The cover 2730 integrally forms the locking clamps 2750 to facilitate securing the cover 2730 to the base 2728. Each of the locking clamps 2750 includes a catchment edge at a distal end of a ramp. The catchment edge snap-fits onto a catchment defined by the base 2728, while ramp provides a resting position on the catchment to provide, for example, a closed but not locked configuration.

FIGS. 28A and 28B illustrate different configurations of an example stimulation lead connection system 2800. In the illustrated examples, the stimulation lead connection system 2800 includes a detachable cable 2802 with a breakaway 2804, a push lock connector 2806, a connector base 2808, and a bandage 2810. In operation, the breakaway 2804 of the detachable cable 2802 is coupled to (e.g., via a magnetic connector, etc.) a corresponding breakaway 2811 of a generator cable 2812. While the detachable cable 2802 is illustrated as plugging into the push lock connector 2806, the push lock connector 2806 and detachable cable 2802 may utilized any of the connection interfaces described herein (e.g., the magnetic head 1702).

In the illustrated examples, the detachable cable 2802 includes a coiled section 2813. The coiled section 2813 acts like a shock absorber. If there is tension on the push lock connector 2806, the coiled section 2813 prevents or inhibits the lead 206 from getting pulled out of the patient. Further, the force of the adhesive between the connector base 2808 and the skin selected to be greater than the magnetic force between the detachable cable 2802 and the push lock connector 2806. In such a manner, the detachable cable 2802 and push lock connector 2806 will come apart when a force is acted on the pulse generator 2814 and will prevent of inhibit the connector base 2808 or lead 206 from coming loose from the patient. In some examples, the system 2800 is configured such that the order of force required to separate the two components is as follows (from highest to lowest): 1) connector base 2808 to the skin of the patient, 2) the push lock connector 2806 and the connector base 2808 (e.g., via magnetic, snap, and/or friction fit), and 3) the connection between the detachable cable 2802 and push lock connector 2806. This last connection, however, is selected to be strong enough that it does not disconnect during normal activities. In some examples, the detachable cable 2802 includes a connector head 2815 configured to electrically and mechanically coupled the detachable cable 2802 to push lock connector 2806. The magnetic connector head 2815 (sometimes referred to as a "magnetic breakaway head") magnetically couples the detachable cable 2802 to the push lock connector 2806 such that force on the detachable cable 2802 will cause the detachable cable 2802 to disconnect from the push lock connector 2806 before the adhesive holding the connector base 2808 to the skin of the patient disengages from the skin of the patient. The magnetic connector head 2815 may be, for example, any of the magnetic connectors described herein (e.g., the magnetic head 1702, the magnetic head 2102, etc.). Alternatively, in some examples, the connector head 2815 may provide a mechanical connection with a friction fit such that force on the detachable cable 2802 will cause the detachable cable 2802 to disconnect from the push lock connector 2806 before the adhesive holding the connector base 2808 to the skin of the patient disengages from the skin of the patient (e.g., the connector head 2002, etc.).

The generator cable 2812 is connector to the pulse generator 2814 that generates stimulation signals for, for example, stimulation therapy. The pulse generator 2814 is affixed to a mounting pad 2816, which is in turn adhered to the patient. In operation, the connector base 2808 is affixed to an adhesion pad 2818. The adhesion pad 2818 may be an example of adhesion pad 100 of FIG. 1 above. The distal end of the lead 206 is implanted in and/or otherwise therapeutically attached the patient. The proximate end of the lead 206 is mechanically and electrically coupled to the push lock connector 2806. In such a configuration, the distal end of the lead 206 is electrically coupled to the pulse generator 2814. In the illustrated examples (e.g., FIG. 29D below), the lead 206 includes a coiled section 2819. The coiled section 2819 acts like a shock absorber. If there is tension on the push lock connector 2806 and/or the lead 206, the coiled section 2819 prevents or inhibits the lead 206 from getting pulled out of the patient.

A physician may use the push lock connector 2806 to facilitate connecting the lead 206 to the cabling (e.g., the detachable cable 2802 and the generator cable 2812, etc.) from the pulse generator 2814. The connector base 2808 has a rigid top and provides a place for the push lock connector 2806 to snap in to. The connector base 2808 includes adhesion pad 2818 that may be adhered to the skin of the patient. Connecting the connector 2806 to the connector base 2808 (which may be adhered to the skin) is meant to secure the connector 2806 in place during typical use. The cabling connects the push lock connector 2806 to the pulse generator 2814 (e.g., of a SPRINT® PNS System, etc.). The bandage 2810 may be a waterproof IV dressing. The bandage 2810 provides a protective waterproof barrier over the exit site of the lead 206. An adhesive section 2820 of the bandage 2810 is placed over the straight section of the detachable cable 2802, allowing the stimulation signals to travel under this waterproof barrier without compromising the seal itself. The bandage 2810 has a clear non-adhesive window 2822 in the middle to allow the patient/caregiver/physician to view/inspect the exit site of the lead 206 without requiring the bandage 2810 to be removed. This allows for a fewer number of required bandage changes throughout the therapy. In the illustrated example, of FIG. 28A, the coiled section 2813 is at least partially covered by the by the adhesive section 2820 of the bandage 2810. Alternatively, as illustrated in FIG. 28B, the coiled section 2813 may be entirely contained within the clear non-adhesive window 2822.

Figure 29A:
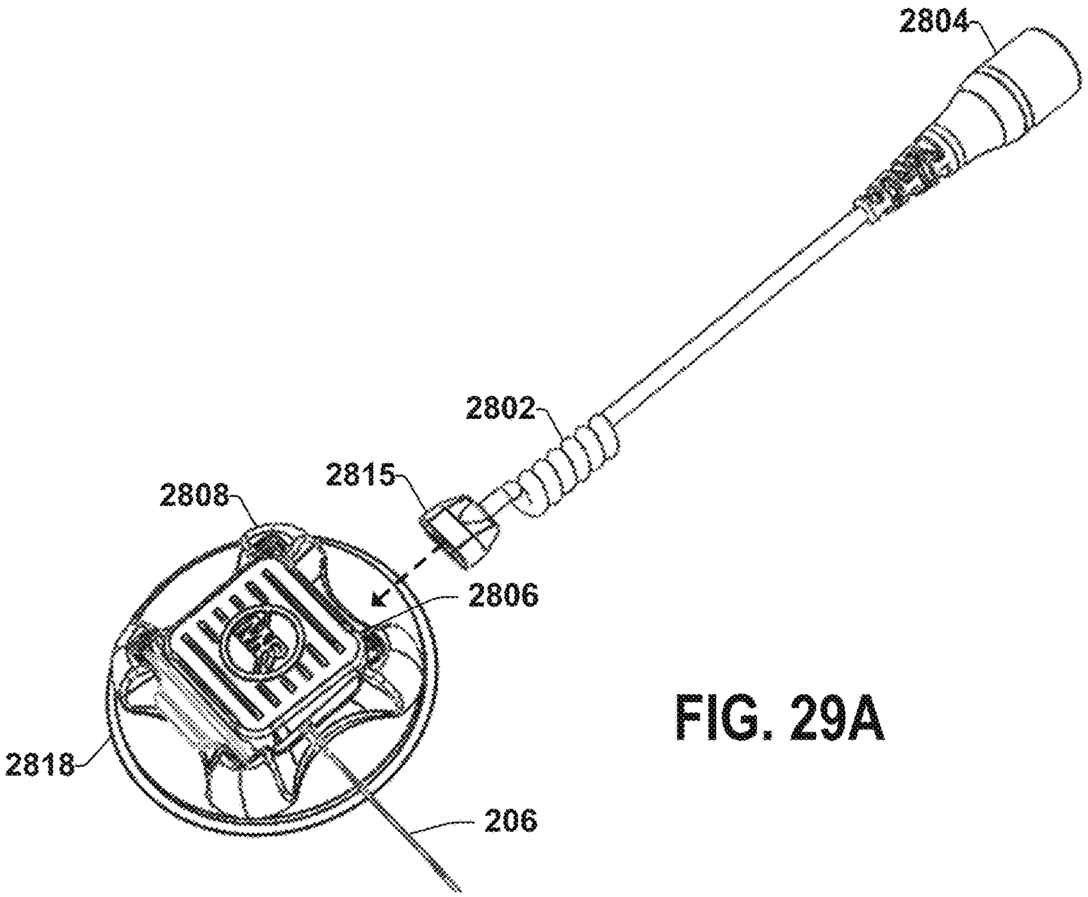
Figure 29B:
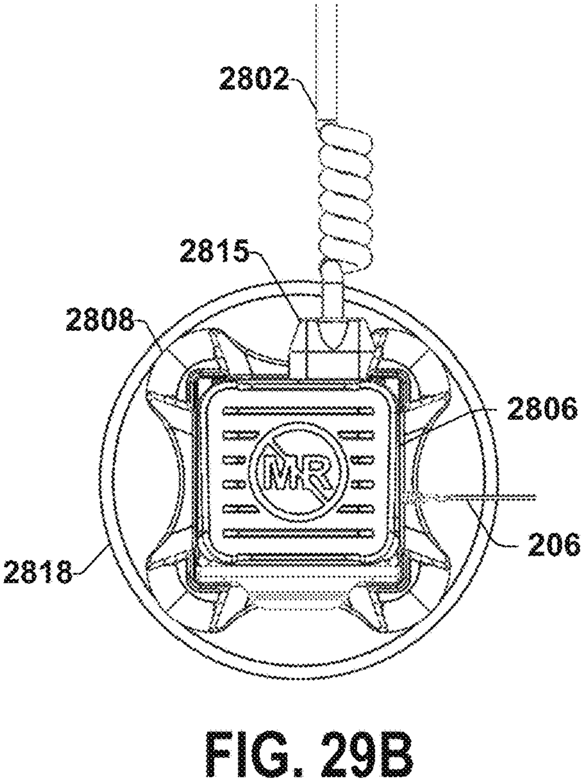
Figure 29D:
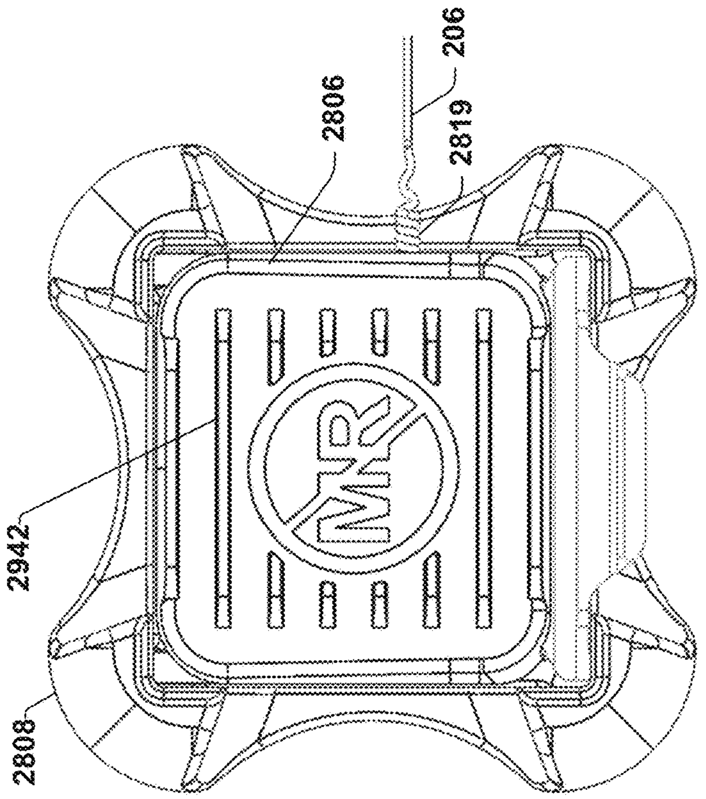
Figure 29C:
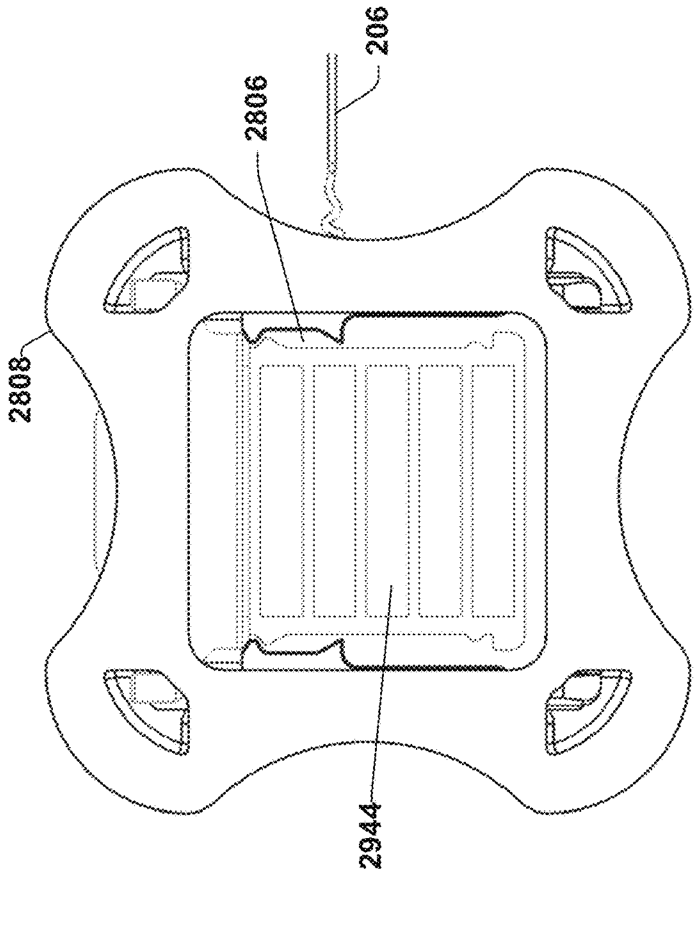
Figure 29E:
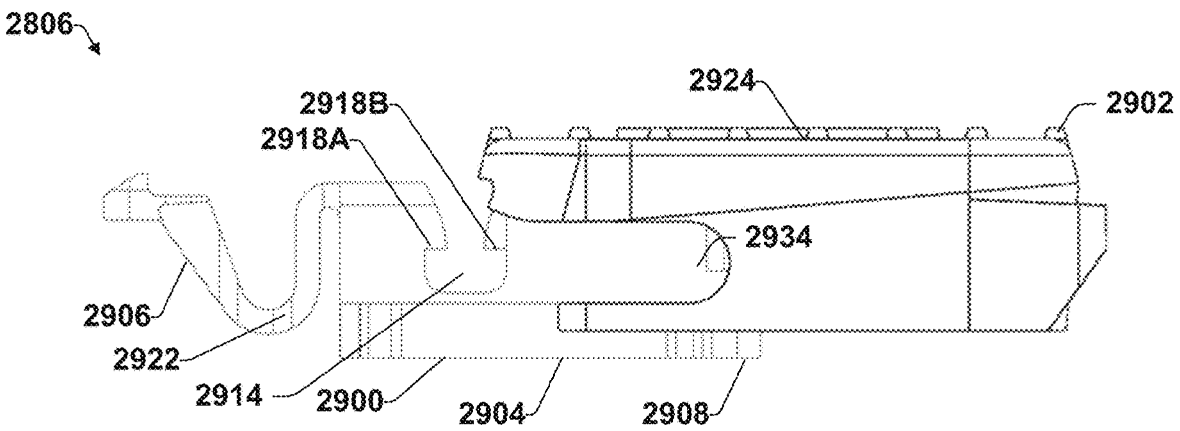
Figure 29F:
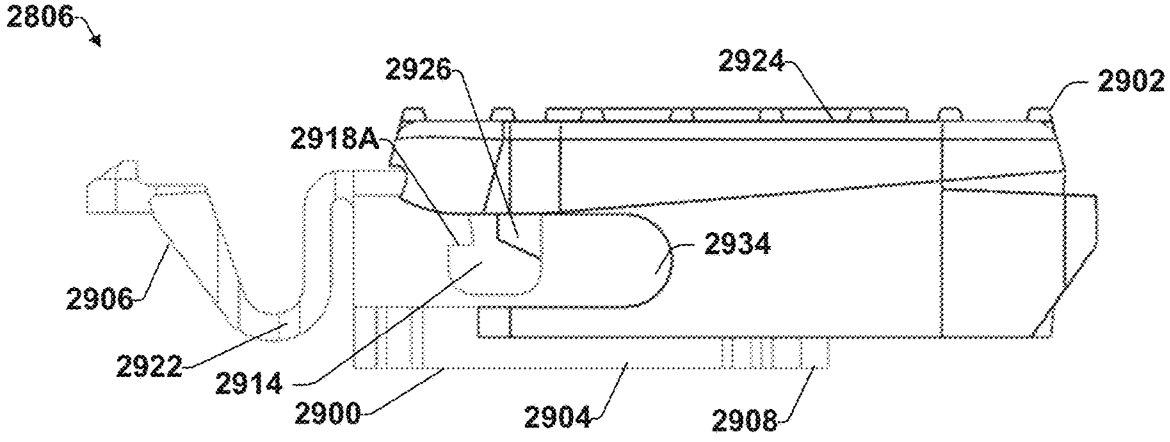
Figure 29G:
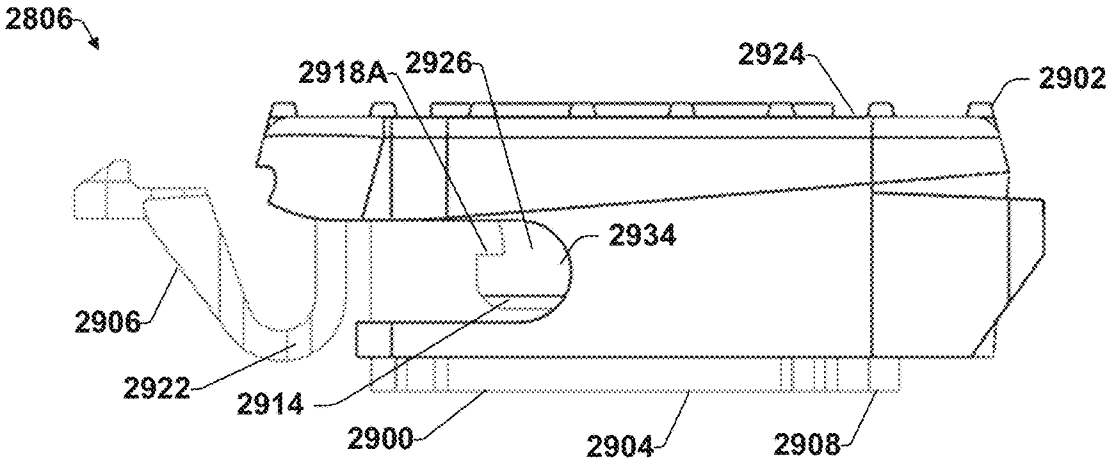
Figure 29I:
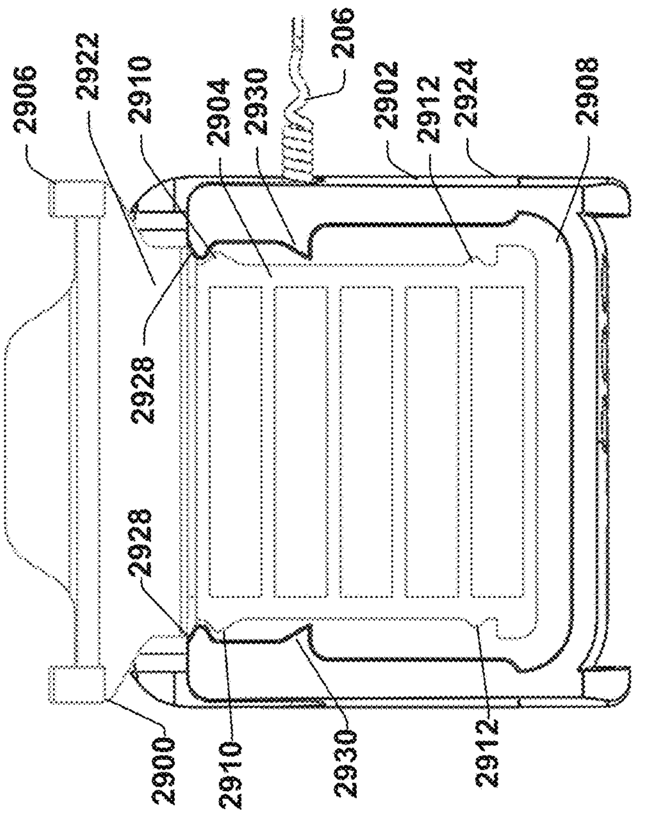
Figure 29H:
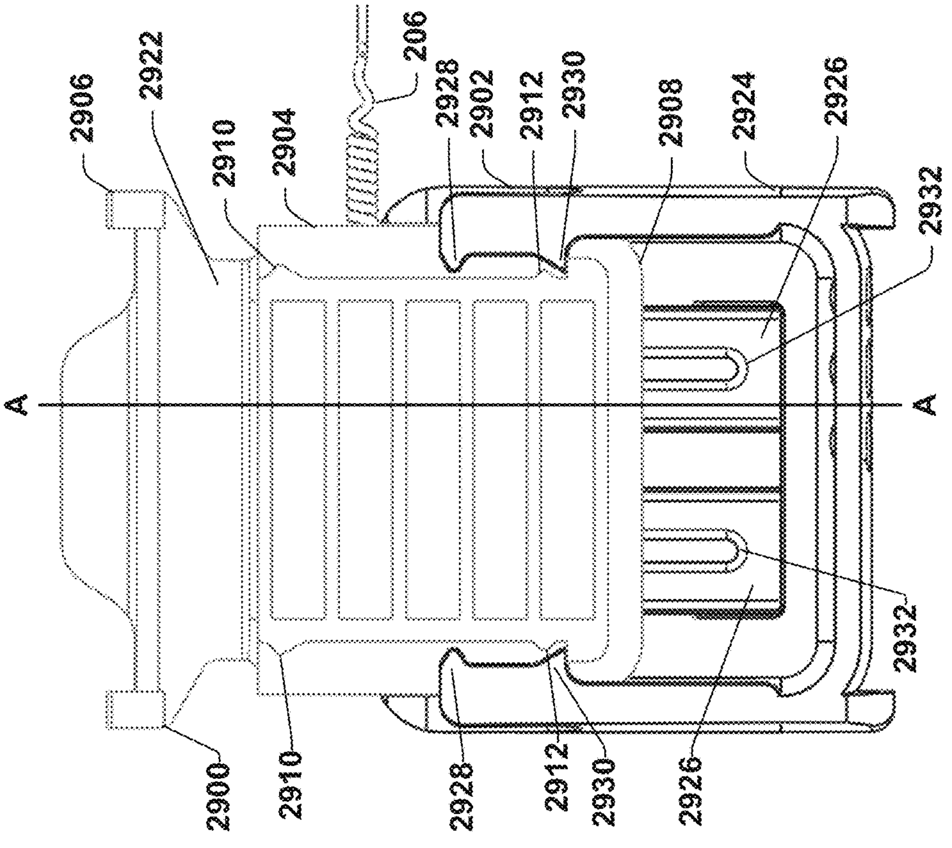
Figure 29K:
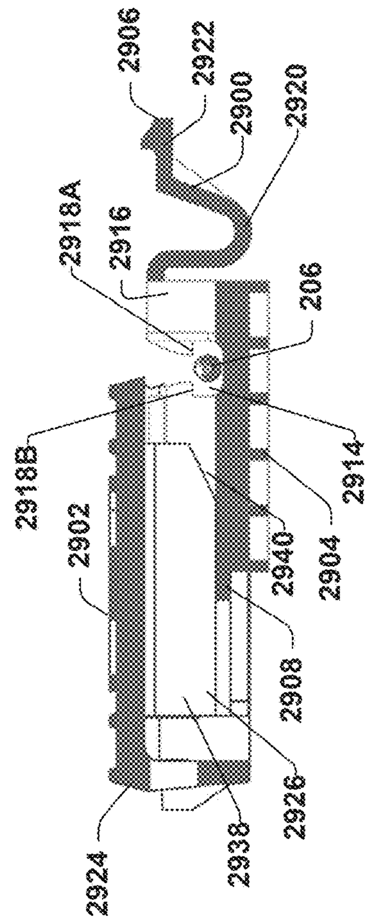
Figure 29L:
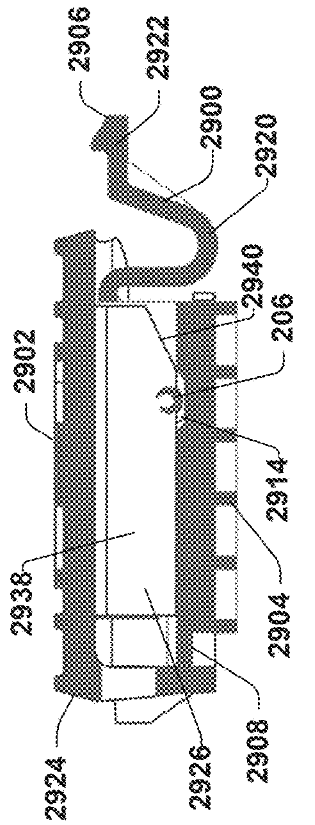
Figure 29J:
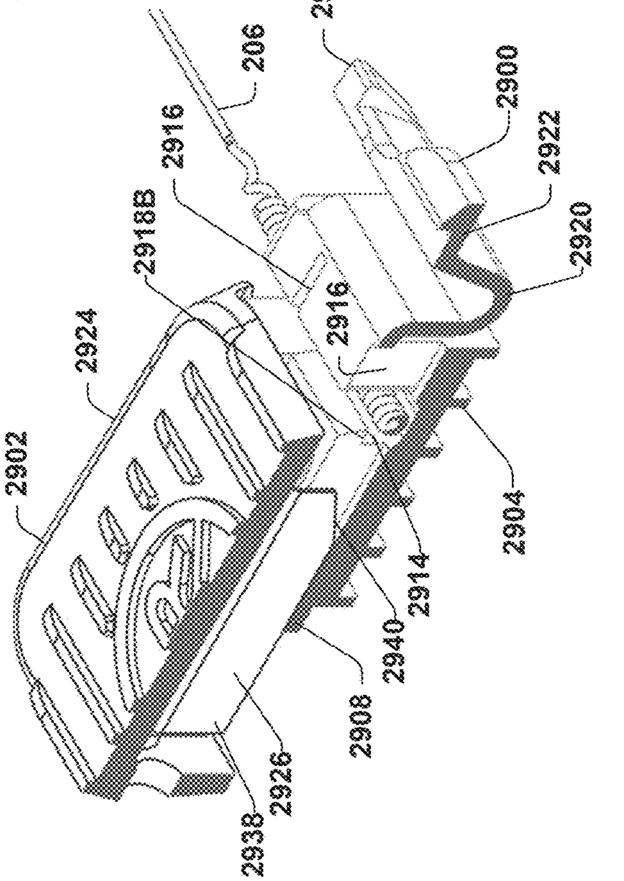

FIGS. 29A, 29B, 29C, 29D, 29E, 29F, 29G, 29H, 29I, 29J, 29K, and 29L illustrate the example push lock connector 2806 and connector base 2808 of FIG. 28. The push lock connector 2806 has an open position and a closed position. Examples of the push lock connector 2806 in the open position are illustrated in FIGS. 29E, 29F (partially opened), 29H, 29J, and 29K. Examples of the push lock connector 2806 in the closed position are illustrated in FIGS. 29A, 29B, 29C, 29D, 29G, 29I, and 29L. As illustrated in FIGS. 29A, 29B, 29C, and 29D, the push lock connector 2806 is configured to be snap fit into the connector base 2808. FIGS. 29J, 29K and 29L are cross-sectional views of the push lock connector 2806 (from the A-A line illustrated in FIG. 29H).

Figure 32A:
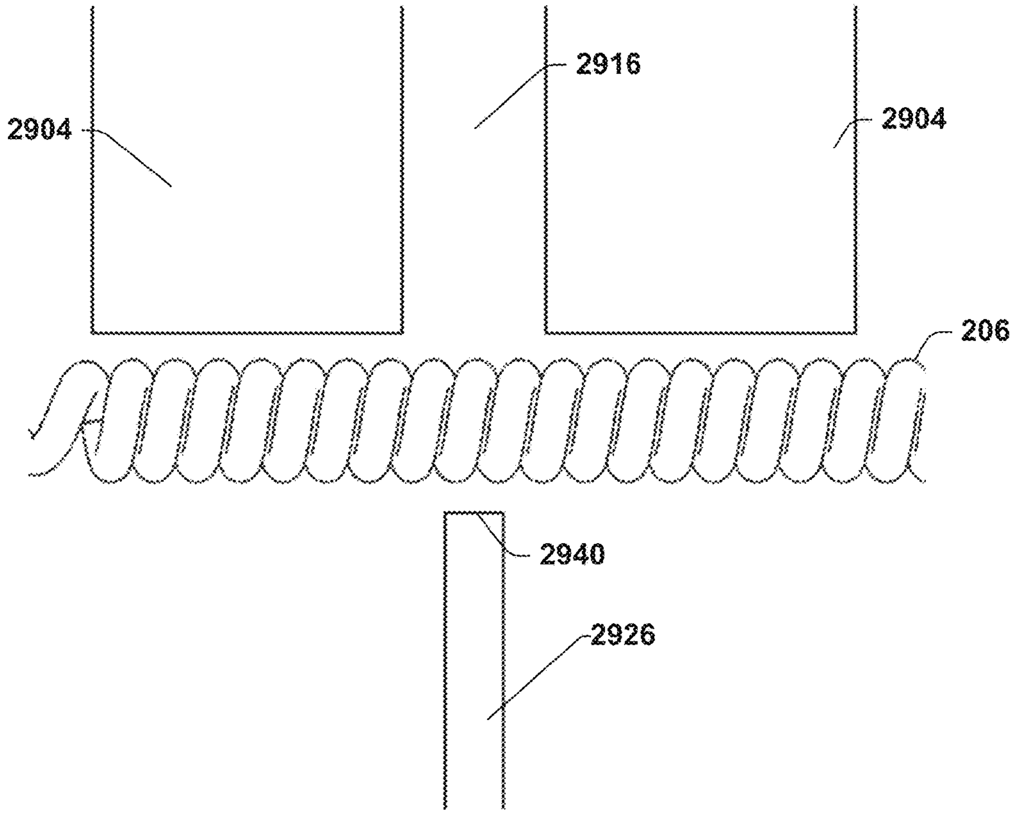
Figure 32B:
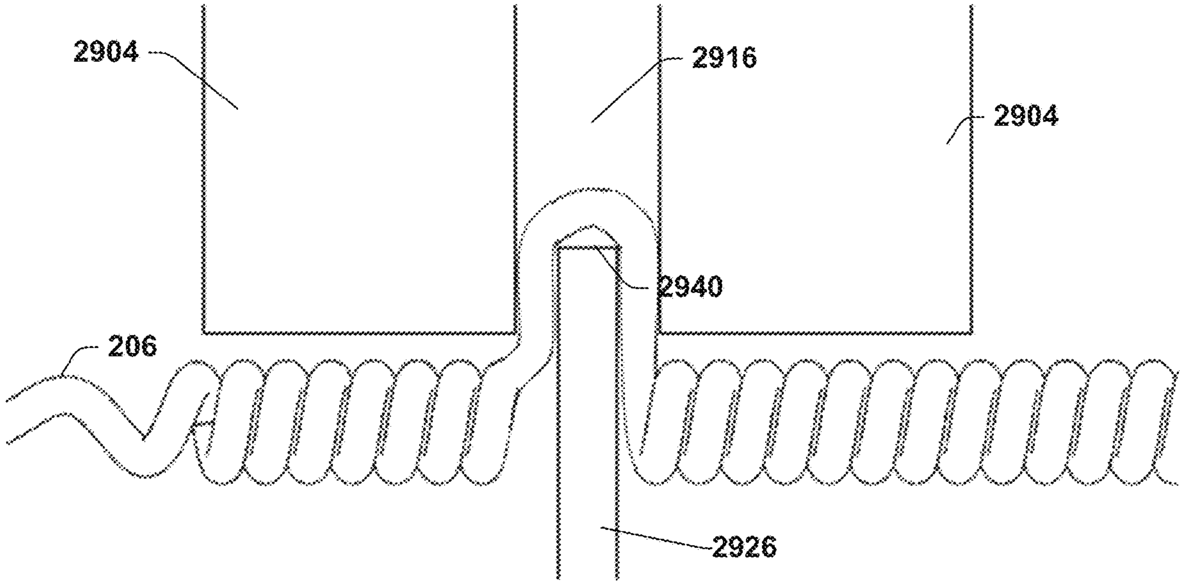

The push lock connector 2806 includes an insert 2900 and a body 2902. Like the push lock connector 700 of FIGS. 7A, 7B, 7C, and 7D, inserting the insert 2900 into the body 2902 with the lead in the push lock connector 2806 locks the lead in the push lock connector 2806 and, in some examples, causes one or more blades to engage with the lead 206. This can be done with a single hand by the clinician. As a separate key is not utilized to lock and unlock the bodies 2900 and 2902 relative to one another, a single hand can be utilized. An example of the insert 2900 is illustrated in FIGS. 30A, 30B, and 30C. An example of the body 2902 is illustrated in FIG. 31. As illustrated in FIGS. 32A and 32B, when the insert 2900 is pushed into the body 2902 with the lead 206 from the open position (FIG. 32A) into the closed position (FIG. 32B), the lead mechanically and electrically couples to the push lock connector 2806.

The insert 2900 includes a chassis 2904, a handle 2906, an insertion guide 2908, forward latches 2910, and rearward latches 2912. The chassis 2904 defines a lead channel 2914 and one or more blade channels 2916 perpendicular to the lead channel 2914. The lead channel 2914 accepts the lead 206. In the illustrated example, the lead channel 2914 includes a cooperating ledges 2918A and 2918B that facilitate, for example, securing the lead 206 when the push lock connector 2802 is in the closed position. For example, the cooperating ledges 2918A and 2918B may inhibit movement of the lead normal to the lead channel 2914 when blades contact the lead as the push lock connector 2806 is shut. The blade channels 2916 are configured to facilitate the blades (e.g., blades 2926 below) sliding through the blade channels 2916 when the push lock connector 2802 opens and closes.

The handle 2906 includes a semi-rigid connection member 2920 that deforms when the push lock connector 2806 is inserted into the connector base 2908. This provides a fiction fit into the connector base 2908 such that the force of the connection member 2920 pushing back against the deformation selectively locks the push lock connector 2806 into the connector base 2908. To release the push lock connector 2806, force may be applied to a handle member 2922 of the handle 2906 to deform the connection member 2920 sufficiently to release the push lock connector 2806 from the connector base 2908. The insertion guide 2908 stays in the body 2902 in both the open and closed position to, for example, provide a stable connection between the insert 2900 and the body 2902. The forward latches 2910 and the rearward latches 2912 restrict the movement of the insert 2900 and selectively lock the push lock connector 2806 open and closed positions respectively in operation with the body 2902 (as described below).

The body 2902 includes chassis 2924, one or more blades 2926, forward latches 2928, and rearward latches 2930. In the illustrated examples, the chassis 2924 includes blade mount members 2932 configured to slidably accept the blades 2926. The chassis 2924 defines ports 2934 through which the lead may pass when the lead is in the lead channel 2914. The ports 2934 may generally be a U-shaped aperture in the chassis 2924.

In the illustrated examples, the blades 2926 are made of an electrically conductive material. In the illustrate examples, the body 2902 includes two blades 2926. However, in other examples, the body 2902 may include more or fewer blades 2924, e.g., one, three, four, five, six, etc. The blades 2926 are directly or indirectly electrically coupled to a connector port that accepts the detachable cable 2802 (as shown, e.g., in FIGS. 28 and 29B, etc.). The blades 2926 are generally a U-shaped bracket with a top 2936 and two sides 2938. The top 2936 interfaces with one of the blade mount members 2932 and connects the two side members 2938. Each of the side members 2938 defines a leading edge 2940 that interfaces with the lead when the push lock connector 2806 is closed. The leading edge 2940 may be configured (e.g., sharpened, etc.) to displace the insulation from a portion of the lead to expose the underlying conductor(s) or conductive wire(s), strand(s), filament(s) and/or cable(s). For example, the angled leading edge 2940 may include a cutting edge to strip or sever the lead when the insert 2900 in pushed into the body 2902 into the closed position. In such a manner, when the push lock connector 2806 is closed, the blades 2926 are electrically coupled to the underlying conductive wire(s) of the lead.

As best illustrated in FIGS. 29H and 29I, the forward latches 2928 and the rearward latches 2930 of the body 2902 cooperated with the forward latches 2910 and the rearward latches 2912 of the insert 2900 to define the open position and the closed position of the push lock connector 2806. In the open position (e.g., as illustrated in FIG. 29H), the rearward latches 2930 of the body 2902 snap between the chassis 2904 of the insert 2900 and the rearward latches 2912 of the insert 2900. This inhibits the insert 2900 from being fully removed from the body 2902 and selectively locks the push lock connector 2806 in the open position. In the closed position (e.g., as illustrated in FIG. 29I), the forward latches 2928 of the body 2902 engage the forward latches 2910 of the insert 2900. This selectively locks the push lock connector 2806 in the closed position and inhibits the push lock connector 2806 from transitioning to the open position without a force being exerted on the insert 2900 (e.g., via the handle 2906, etc.).

As best illustrated in FIGS. 29C and 29D, the push lock connector 2806 includes a set of ridges 2942 on a top surface of the push lock connector 2806 and a set of grooves 2944 on a bottom surface of the push lock connector 2806. The ridges 2942 on the top are used to help enhance the one-hand engagement. The grooves 2944 on the bottom facilitate holding the push lock connector 2806 with one hand or even with as little force as two fingers (e.g., index finger and thumb). During the procedure, clinician may be wearing gloves and/or have their hands or gloves covered or coated with certain medical gels (e.g., a lubricating fluid, gel, or material such as ultrasound gel), which can make their hands and the device slippery and reduce the amount of force that can be applied to the connector are used so the clinician may have some on his/her hand. This can make grasping the device difficult, which is why the ridges 2942 and grooves 2944 being present help with grasping.

The connector base 2808 is configured to selectively receive the push lock connector 2806. The connector base 2808 includes pillars 2824 that cooperate with the handle 2906 to snap fit and/or friction fit the push lock connector 2806 into the connector base 2808. One or more pillars 2824 may define a cable passage to facilitate connecting and/or disconnecting the detachable cable 2802 to the push lock connector 2806 when the push lock connector 2806 is situated in the connector base 2808. In some examples, the connector base 2808 and/or the push lock connector 2806 may include a locking mechanism to prevent the user/patient from opening the push lock connector 2806 (e.g., moving the insert 2900 to the open position relative the 2902, etc.). The locking mechanism may be of any configuration. In some example, the locking mechanism is a tamper resistant setscrew. It should be understood, however, that any kind of locking device may be utilized.

Figure 32C:
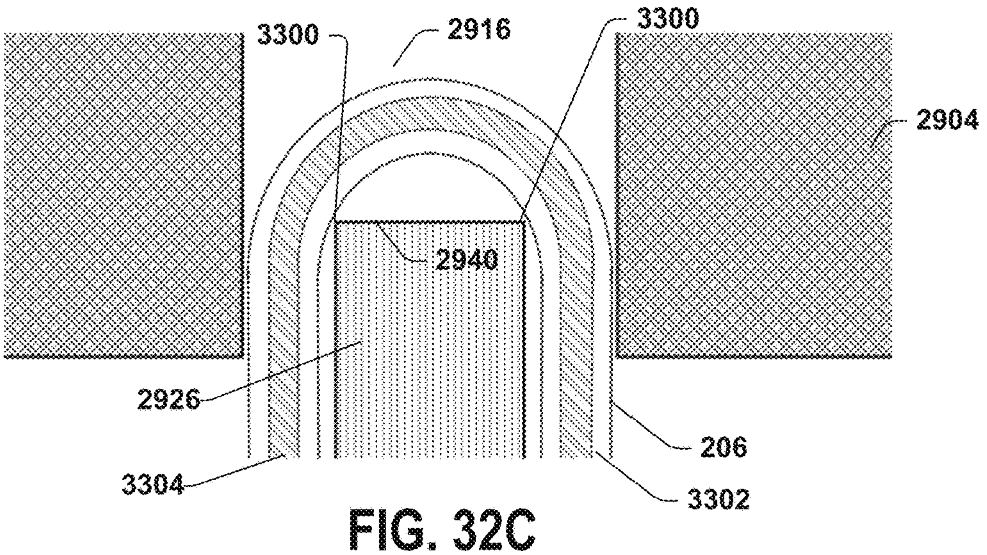
Figure 32D:
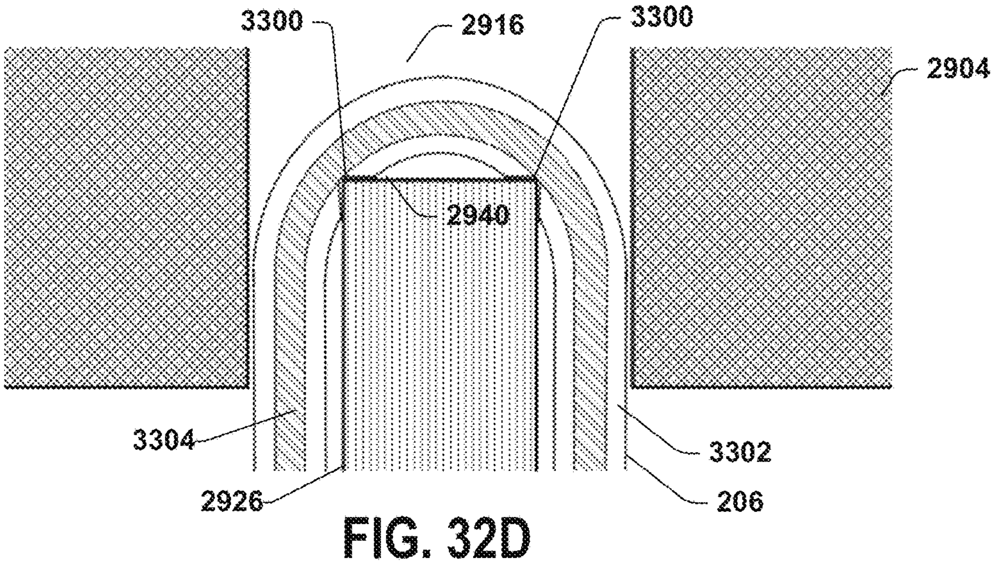
Figure 32E:
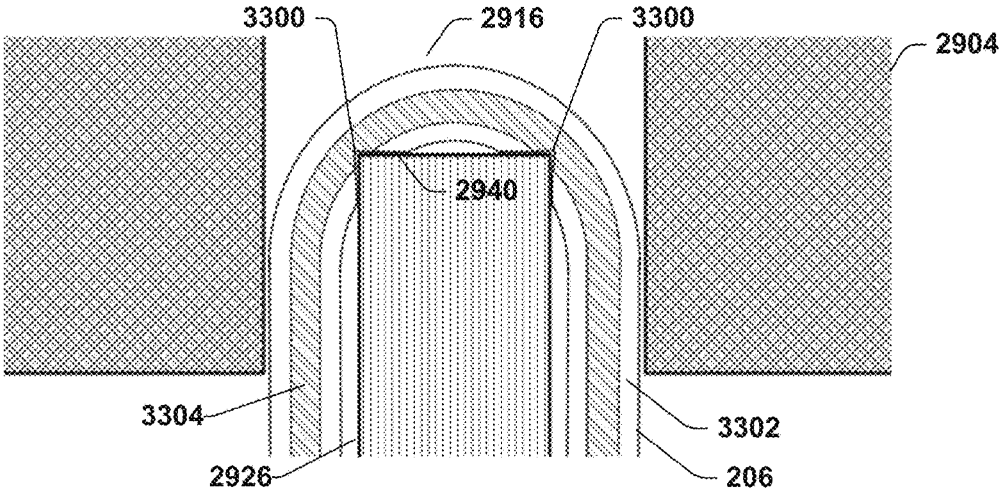
Figure 32F:
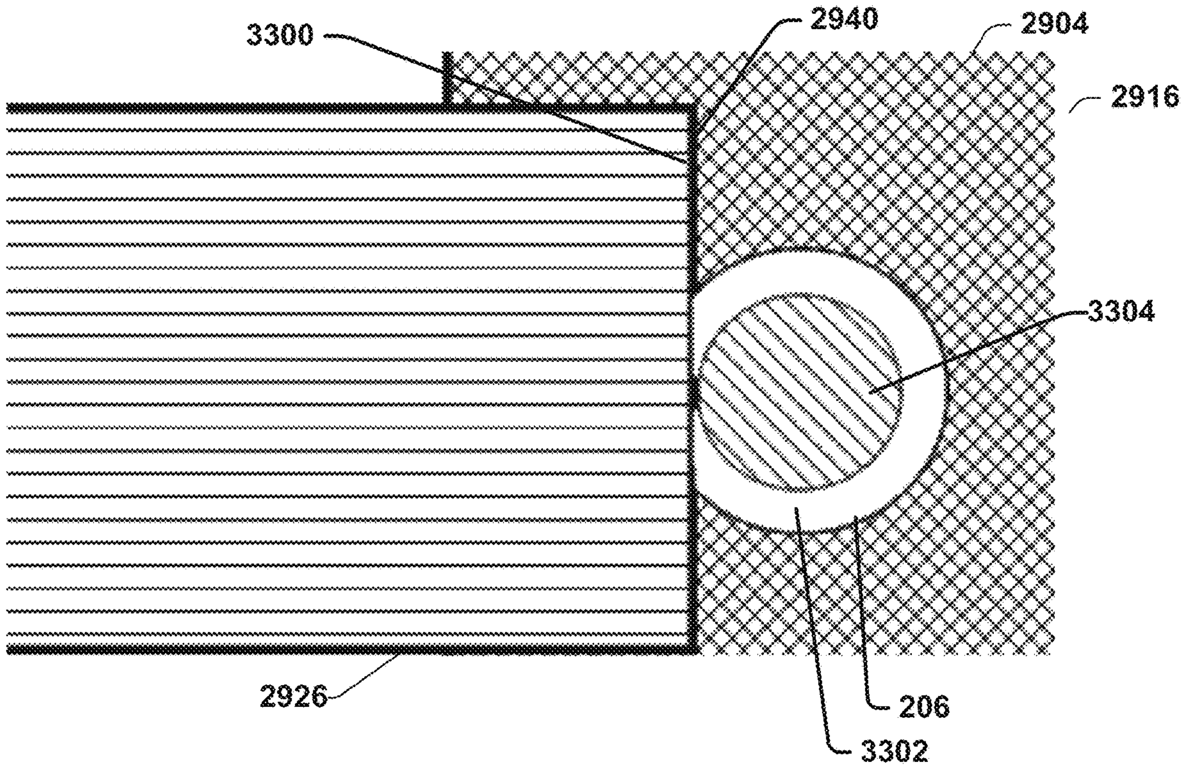
Figure 32G:
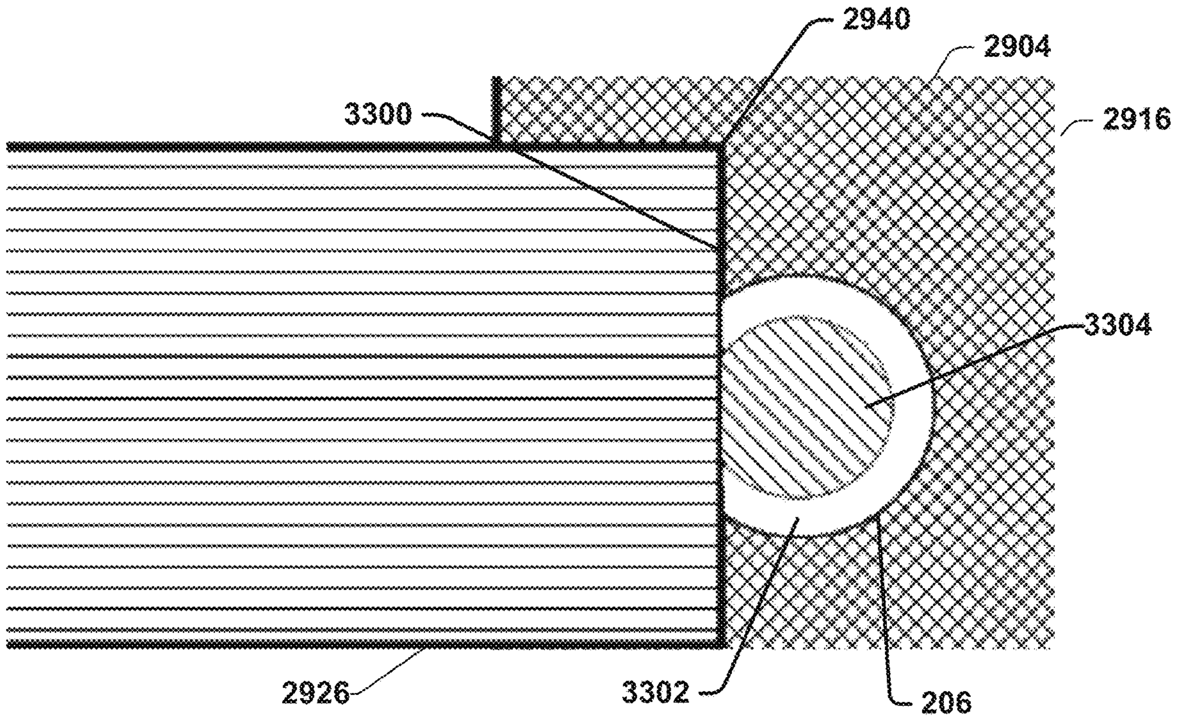

FIGS. 32A, 32B, 32C, 32D, 32E, 32F, and 32G are conceptual diagrams of the blade 2926 of the insert 2900 interacting with a lead 206, in accordance with the teachings of this disclosure. In the illustrated examples of FIGS. 32A and 32B, the blade 2926 captures the lead 206 within the blade channel 2916 such that the lead 206 is secured within the push lock connector 2806. FIGS. 32C, 32D, and 32E illustrate the blade 2926 with one or more cutting edges 3300 that displace (e.g., cuts through) an insulation layer 3302 displacement connection to form a connection with the conductive lead wire 3304 of the lead 206. As illustrated in FIGS. 32D and 3F, when the insert 2900 is pushed into the body 2902, the cutting edges 3300 of the blade 2926 displace (e.g., pierce) the insulation layer 3302 as the lead 206 is captured between the blade 2926 and the body 2904 of the insert 2900. In the illustrated example of FIGS. 32E and 32G, the cutting edge 3300 pushes into contact with the conductive lead wire 3304, electrically coupling the blade 2926 to the lead 206. In such a manner, the push lock connector 2806 becomes electrically coupled to the lead 206.

Figure 34A:
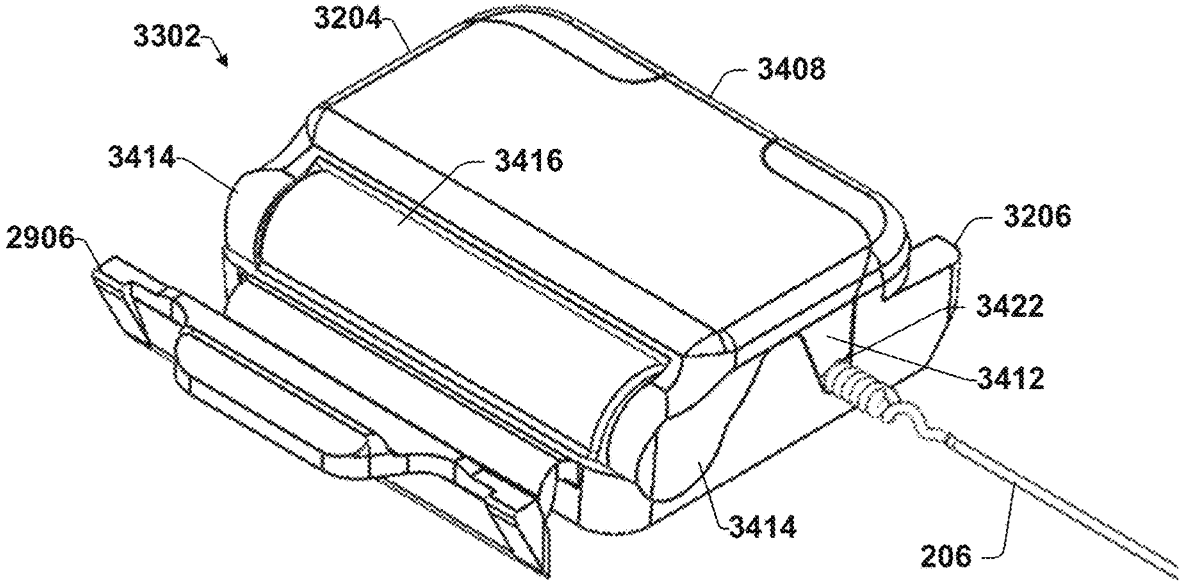
Figure 34B:
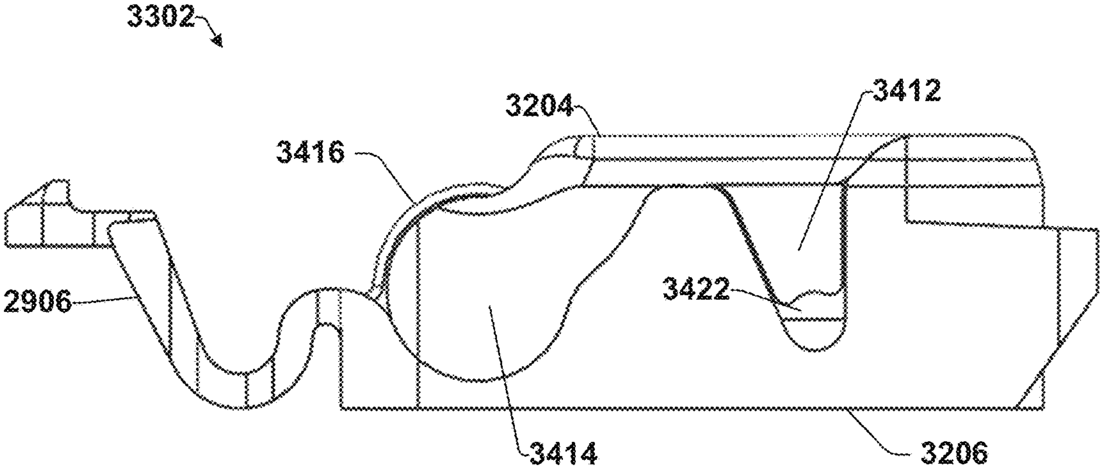
Figure 34C:
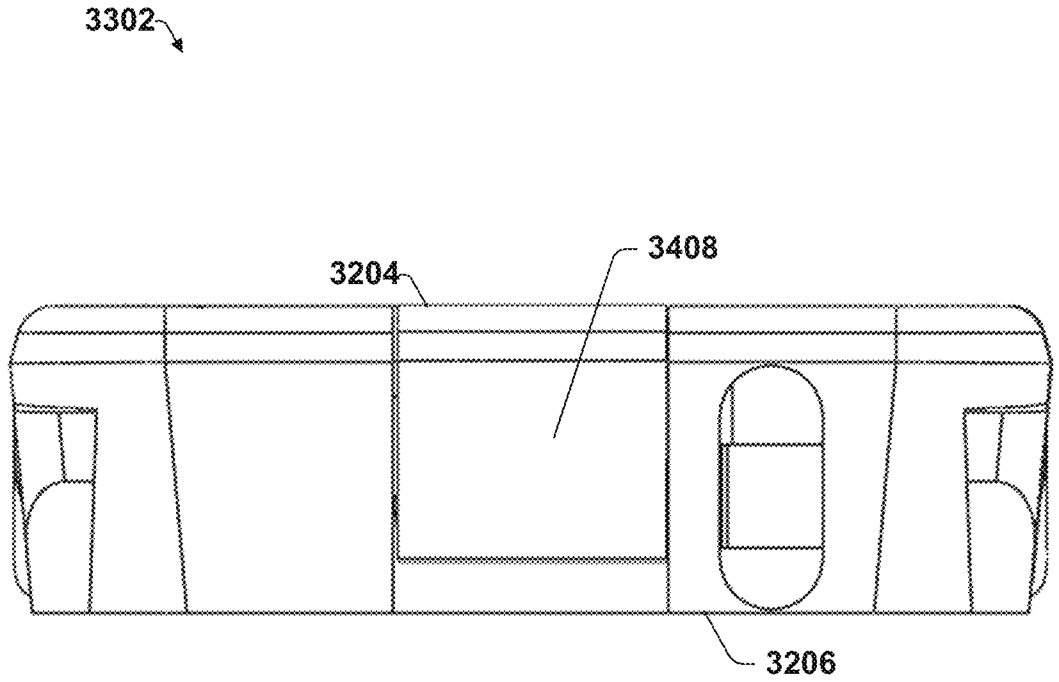
Figure 34D:
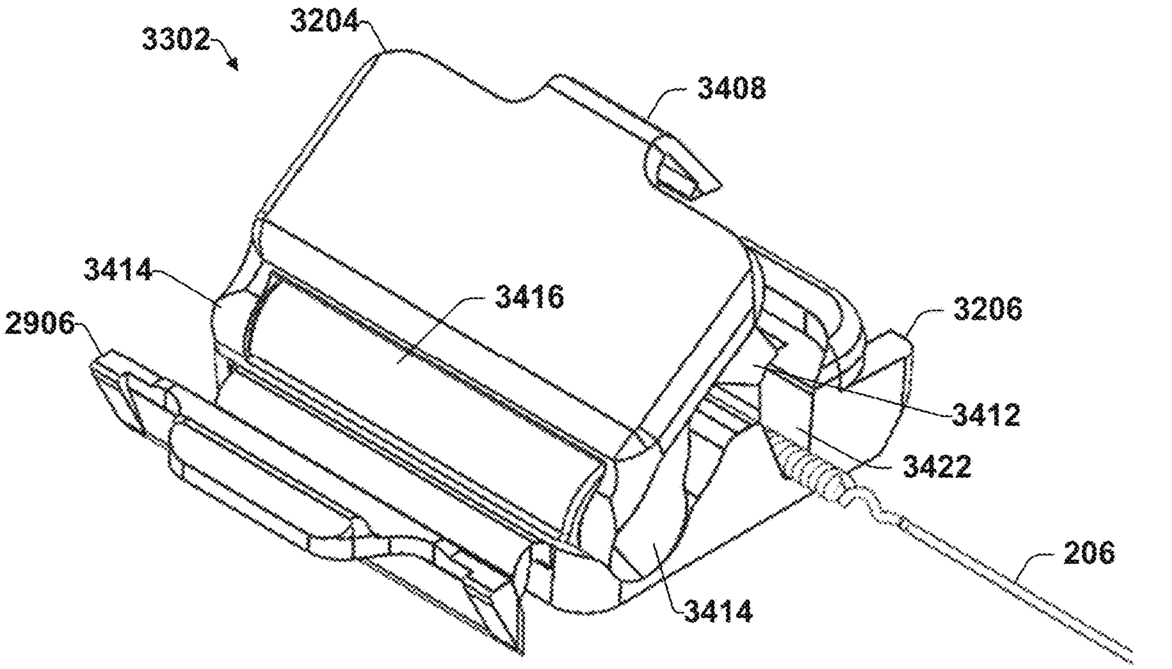
Figure 34E:
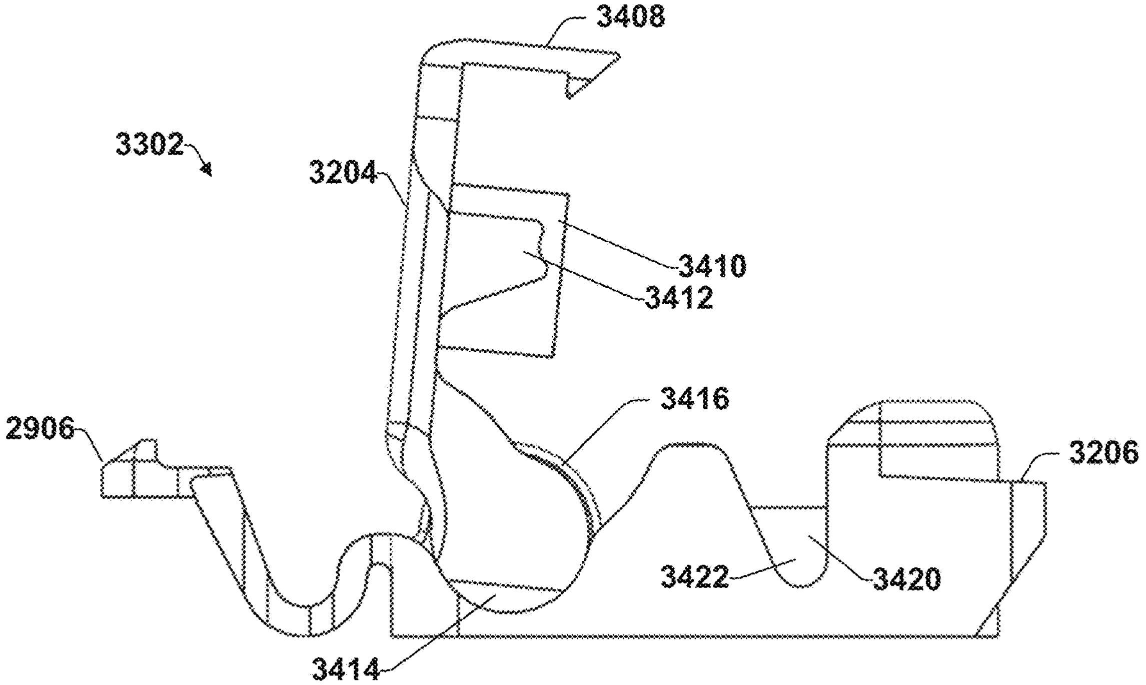
Figure 34F:
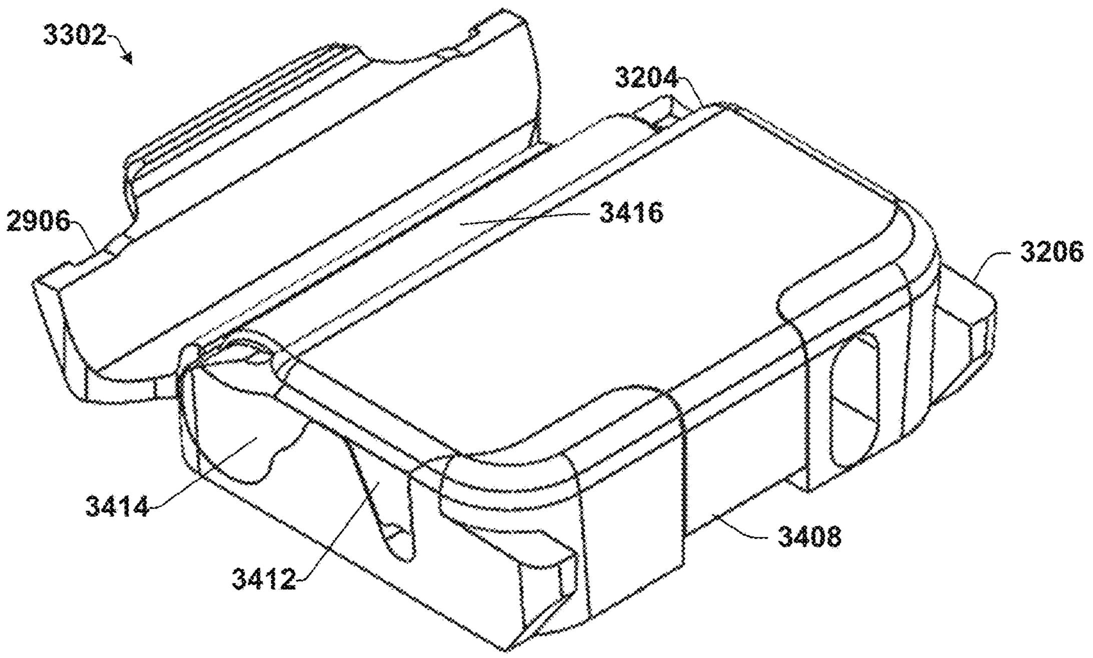
Figure 34G:
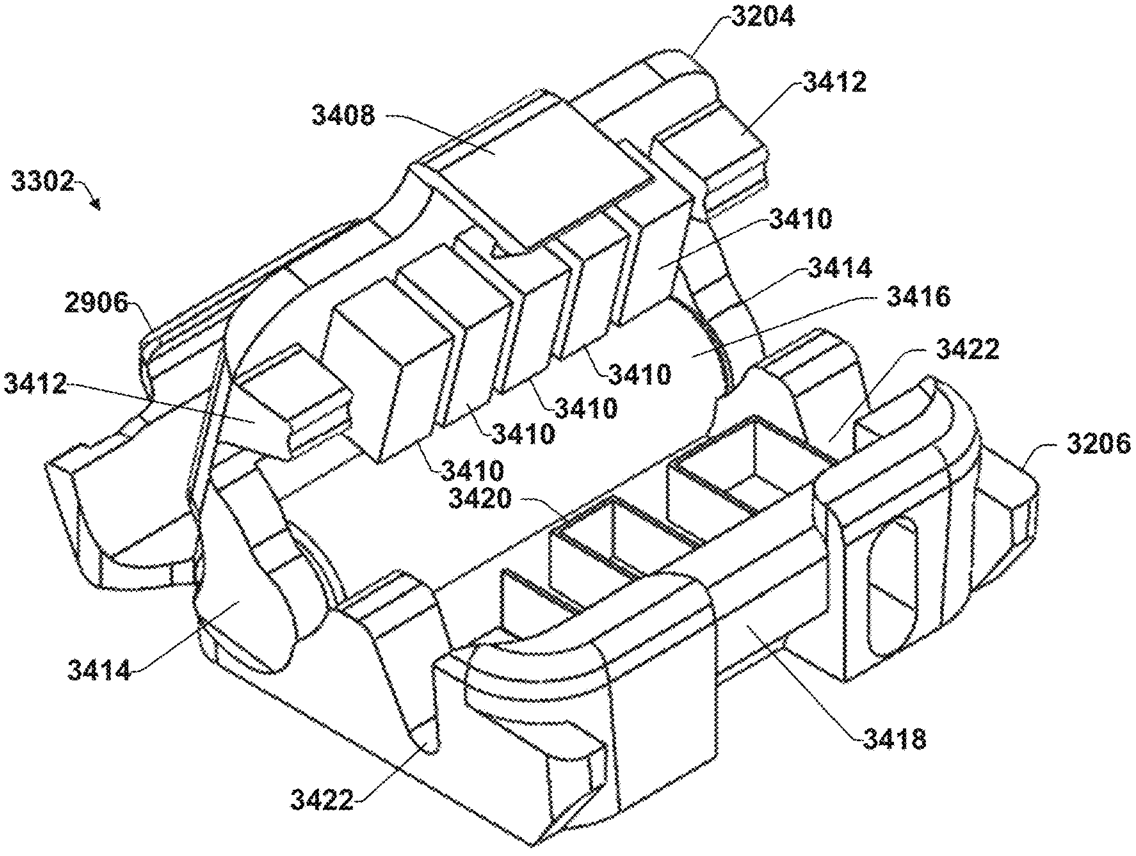
Figure 34H:
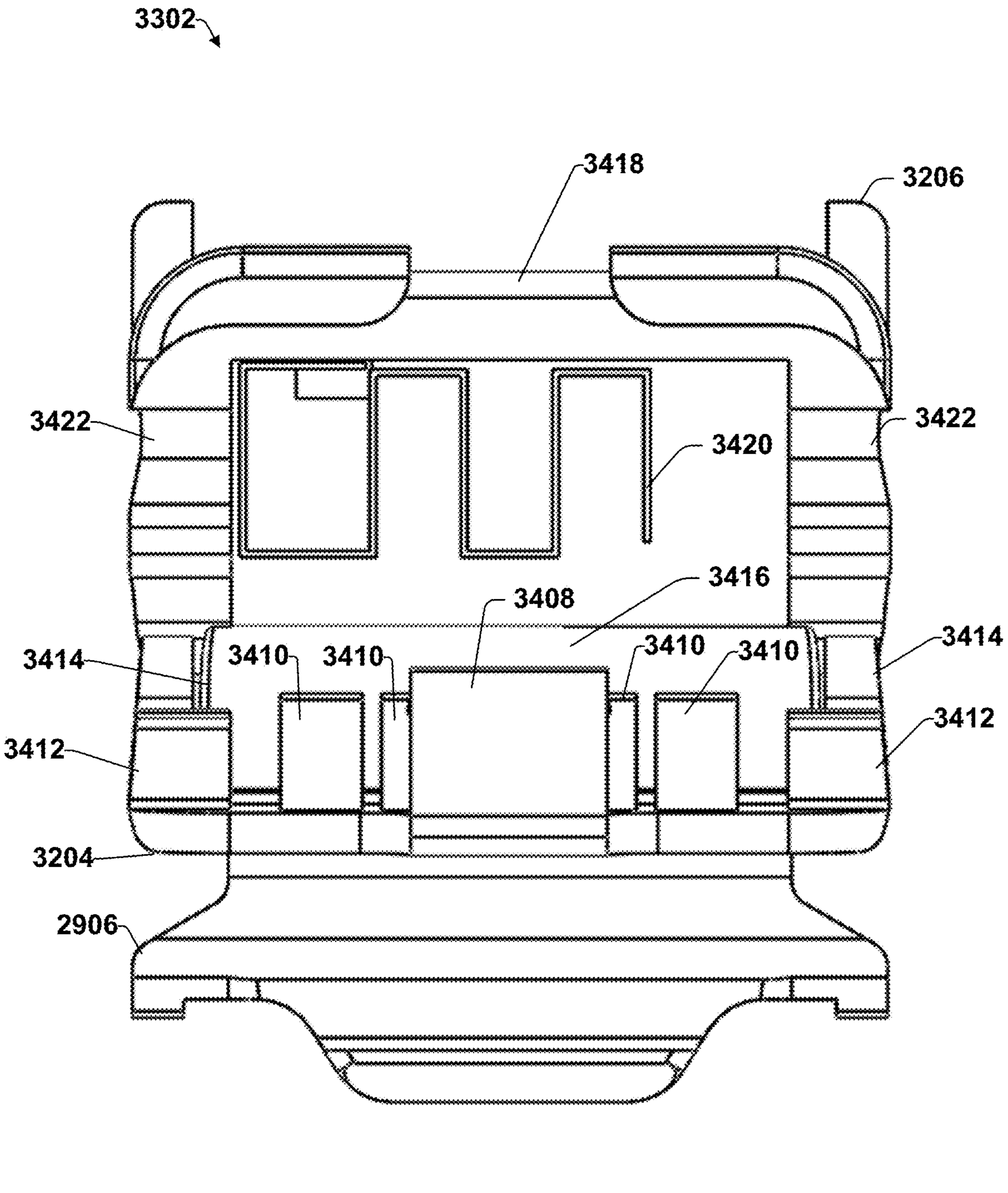
Figure 34I:
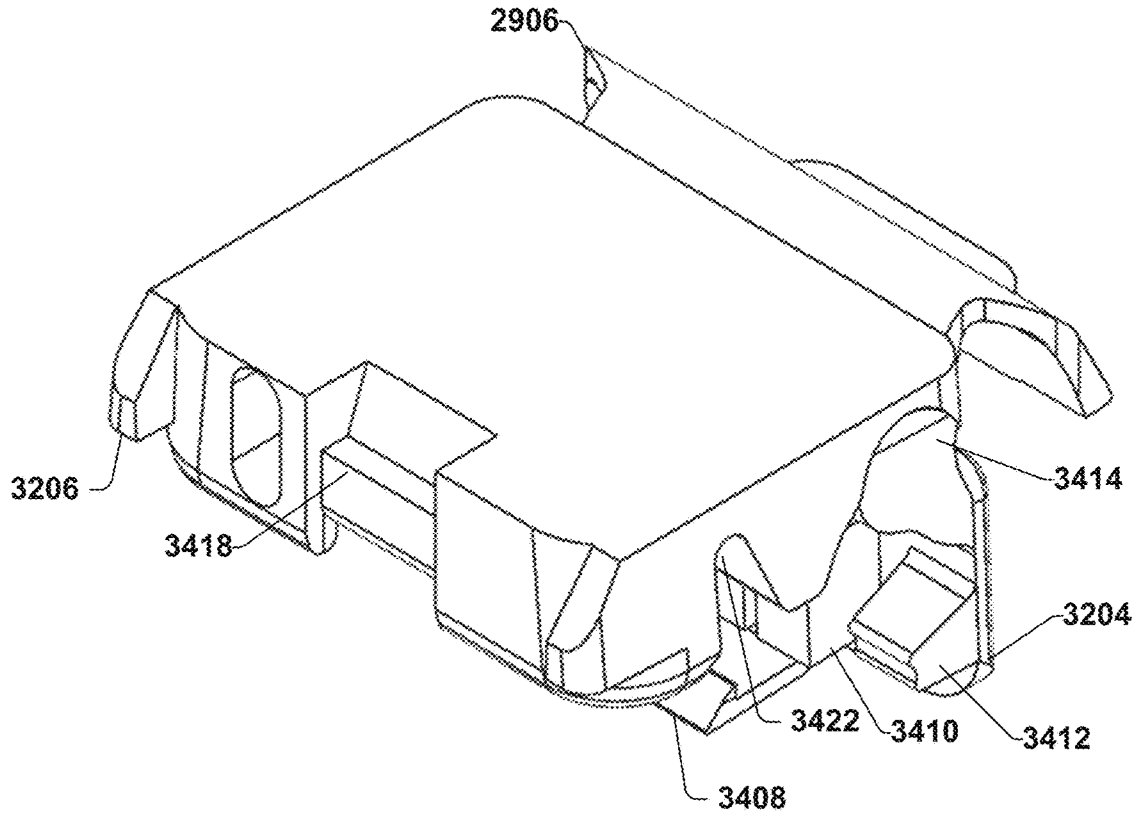
Figure 34J:
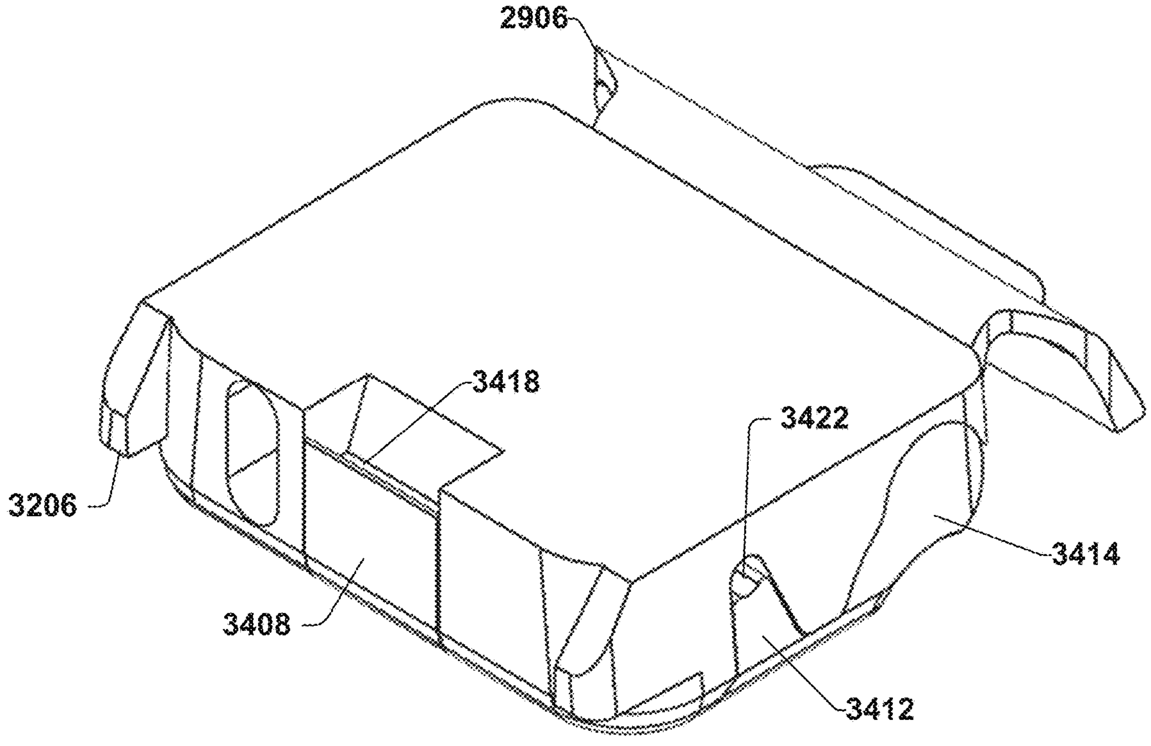

FIG. 33 illustrates an example stimulation lead connection system 3300. In the illustrated example, the stimulation lead connection system 3300 includes the detachable cable 2802 with the breakaway 2804, a clamshell connector 3302, the connector base 2808, and the bandage 2810. While not illustrated in FIG. 33, the lead connection system 3300, in operation, may be connected to the pulse generator 2814 as illustrated in FIG. 28. While the detachable cable 2802 is illustrated as plugging into the clamshell connector 3302, the clamshell connector 3302 and detachable cable 2802 may utilized any of the connection interfaces described herein. Additionally, the lead connection system 3300 may incorporate any of the lead anchors described herein. In some examples, the push lock connector 2806 and the clamshell connector 3302 may be functionally interchangeable. The clamshell connector 3302 has an open position and a closed position. Examples of the clamshell connector 3302 in the open position are illustrated in FIG. 34D (partially opened), 34F, 34G, 34H, and 34I. Examples of the clamshell connector 3302 in the closed position are illustrated in FIGS. 34A, 34B, 34C, 34F, and 34J. As illustrated in FIG. 33, the clamshell connector 3302 is configured to be snap fit into the connector base 2808.

The clamshell connector 3302 includes a cover 3204, a base 3406, and the handle 2906. The cover 3204 has a generally flat, planar shape. The cover 3204 integrally forms a locking clamp 3408 to facilitate securing the cover 3204 to the base 3406. The cover 3204 includes blade guides 3410, port guides 3412, and hinge supports 3414. Blade channels 3416 are defined between the blade guides 3410 to accept the blade (e.g., the blade 3420 below). The port guides 3412 interface with the base 3406 to secure the lead to the clamshell connector 3302 when the clamshell connector 3302 is closed. An end of the port guides 3412 is configured to at least partially encompass the lead when the clamshell connector 3302 is closed. The cover 3204 rotatably connects to the base 3406 via a hinge or axle formed between the hinge supports 3414. In the illustrated example, the base 3406 and the cover 3404 are rotatably connected along a side such that the axis of rotation is substantially parallel to the lead when the lead is inserted into the clamshell connector 3302.

The base 3406 includes a hinge support 3416, a catchment 3418, and a blade 3420. The base 3406 also defines lead ports 3422 that are configure to accept the lead and, when the clamshell connector 3302 is closed, the port guides 3412 of the cover 3402. The lead ports 3422 are a generally U-shaped aperture that cooperates with the port guides 3412 to secure the lead in the clamshell connector 3302. The hinge support 3416 receives the hinge or axle formed between the hinge supports 3414 of the cover 3404. The catchment 3418 is configured to snap lock with the locking clamp 3408 to selectively lock the clamshell connector 3302 in the closed position.

The blade 3420 is made of an electrically conductive material. In the illustrate examples, the body 2902 includes a single blade 3420 formed in a pattern to be received in the blade channels 3416 when the clamshell connector 3302 is closed. However, in other examples, the body 2902 may include more blades 3420. The blade 3420 is positioned between the lead ports 3422 such that, when the clamshell connector 3302 is closed, the lead is secured between the blade 3420 and the blade guides 3410 between the lead ports 3422. The blades 2926 are directly or indirectly electrically coupled to a connector port that accepts the detachable cable 2802 (as shown, e.g., in FIG. 33). The blade 3420 defines a leading edge 3422 that interfaces with the lead when the clamshell connector 3302 is closed. The leading edge 3422 may be configured (e.g., sharpened, etc.) to displace the insulation from a portion of the lead to expose the underlying conductor(s) or conductive wire(s), strand(s), filament(s) and/or cable(s). In such a manner, when the clamshell connector 3302 is closed, the blades 3420 are electrically coupled to the underlying conductive wire(s) of the lead.

The connector may be held in position to avoid inadvertent pulling and/or tugging on the lead due to movement or shifting of the connector under bandaging or during bandage changes by means of a device or structure, such as a mount and/or cradle, while enabling the connector to be moved and/or adjusted as needed, and the mount and/or cradle to be replaced and/or adjusted as needed. The mount and/or cradle may hold the connector in position via plastic molding, adhesive, snaps, suture and/or other means or mechanisms, including prespecified and designed mechanical forces such as a pressure or press fit, friction fit, and/or interference fit, enabling the optimal balance between intentional ease of separation and/or mating and intentional resistance or difficulty of separation and/or mating of the components with the use of prespecified materials, construction, geometric dimensions, and/or tolerances. In one example embodiment, plastic molding of the cradle may incorporate one or multiple edges and/or lips that secure the connector into the cradle by means of, but not limited to, sliding the connector under the edge(s) and/or lip(s) in a lateral (e.g., side-to-side) and/or rotational (e.g., turning) direction. As a non-limiting example, plastic molding of the cradle may incorporate one or multiple edges and/or lips so that the connector is secured into place when pressed into the cradle and/or slid onto the cradle. The connector may be released by pressing and/or pulling on the lip(s) of the cradle to temporarily and/or reversibly but not permanently deform the material and release the connector from the cradle. In another non-limiting example, the connector may snap onto the cradle, and/or may adhere using an adhesive and/or Velcro-like (e.g., hook and loop) material, and/or may be sutured into position. In another non-limiting example, the cradle may hold the connector in the desired position (e.g., not moving freely beneath bandages by a spring which may be released (enable the connector to separate from the cradle) with the press and/or slide of a finger and/or thumb.

The invention is designed to enable it to overcoming challenges of use, and a non-limited example includes the goal of correctly closing the connector on the lead, which is important since the connector may need to be able to close with a one handed and ideally two finger (e.g., index finger and thumb) use or operation, plus the importance of the limitation that the user may only be able to apply a limited amount of force due to the need to use friction to close the device, which may be significantly limited since the user (e.g., clinician) may be wearing gloves and/or have their hands or gloves covered or coated with a lubricating fluid, gel, or material such as ultrasound gel, which can make their hands and the device slippery and reduce the amount of force that can be applied to the connector (e.g., reducing available friction that can be used to close the device), thereby limiting the amount of force that can be used to close the connector and disrupt the insulating coating (e.g., by means of blade(s) and/or teeth) and enable the rest of the applicable parts of the connector to interact and correctly mechanically and/or electrically connect with the conductor(s) or conductive wire(s), strand(s), filament(s) and/or cable(s) of the lead. In an example embodiment, the connector may incorporate a drawer(s) and/or tray(s), slot(s) and/or sliding mechanism(s) into which one or more lead(s) may be laid and which may be closed or squeezed shut using two fingers (e.g., a forefinger and thumb) and/or glide or slide without too much resistance so as to not slip out of the user's fingers when pressure is applied, but enough resistance so as to remain open while the lead is being laid into the drawer(s) and/or tray(s). In another example embodiment, the connector may incorporate a hinged compartment into which one or more lead(s) may be placed, positioned, laid and/or fed which may be closed using two fingers (e.g., a forefinger and thumb). In a non-limiting example, the drawer(s) and/or hinge(s) may incorporate a molded lip (e.g., clasp) with enough strength to keep it closed during system use but may not be so strong that it cannot be opened with a single hand. In another non-limiting example, the drawer(s) and/or hinge(s) may incorporate a spring-loaded locking mechanism so that when pressure (e.g., a two-fingered squeeze) is applied it releases and/or opens for the lead to be placed and/or removed, requiring enough pressure to be applied that the drawer(s) and/or hinge(s) does not freely open during system use but not requiring so much that the drawer(s) and/or hinge(s) cannot be opened using a single gloved hand potentially soiled (e.g., with ultrasound gel) during the implant procedure.

The cabling referred to herein as the connector, connection, lead connector, and/or microlead connector which enables the mechanical and/or electrical connection between the lead and other cabling and/or between the lead and the external pulse generator may make that connection by means of biting, scraping, pressing, and/or deforming the insulation of the lead to enable a conductive material to make contact with the conductor(s) or conductive wire(s), strand(s), filament(s) and/or cable(s) of the lead which otherwise may be coated in an insulating material while avoiding damaging, deforming, and/or fracturing of the lead, conductor(s) or conductive wire(s), strand(s), filament(s) and/or cable(s). The connector may maintain this mechanical and/or electrical connection during patient movement (e.g., bending, walking, exercising, sleeping), during bandage changes (e.g., securing the connector in place, cleaning the site, removing and/or replacing the protective cover, removing and/or replacing the waterproof bandage), and/or during lead testing (e.g., during the initial placement of the lead in the procedure room, after lead deployment into its final position, in the recovery room after the lead placement procedure, in-clinic and/or at-home evaluation of the lead integrity) while also enabling easy removal and replacement and/or change in location along the length of the lead, and while also maintaining the integrity of the lead (e.g., not fracturing, damaging deforming the conductor(s) or conductive wire(s), strand(s), filament(s) and/or cable(s) of the lead). In one example embodiment, this connection may be made by conductive (e.g., metal) teeth of a size small enough to bite and/or scrape through the insulating coating when pressed and/or slid against the lead by the closing of the lead connector but not pressed so tightly that the lead conductor(s) or conductive wire(s), strand(s), filament(s) and/or cable(s) are damaged. In another example embodiment, the connection may be made by conductive sandpaper rough enough to break through the insulating coating when slid and/or rubbed against the lead but fine enough to avoid damaging the lead conductor(s) or conductive wire(s), strand(s), filament(s) and/or cable(s). In another example embodiment, the connection may be made by a blade when the lead is slid, pressed, rolled between, and or compressed against it. In another example embodiment, the lead may be pressed and/or deformed by a sharp piston so that the corner(s) and/or blade(s) break through the insulating coating and make contact with the conductor(s) or conductive wire(s), strand(s), filament(s) and/or cable(s) of the lead and hold the lead in position throughout therapy while avoiding damaging, fracturing, and/or otherwise deforming the lead. The connections described may function when but not limited to when the hinge(s) of the connector is being closed, a drawer(s) and/or tray(s), slot(s) and/or sliding mechanism(s) drawer of the connector is being slid or pressed shut, pressure is being placed upon the connector(s) (e.g., by a squeeze), and/or the connector being twisted closed. The connections described may be located at any place within the connector to serve the function of making the mechanical and/or electrical connection between the lead and the cabling, and or between the lead and the external pulse generator.

The fine-wire coiled lead may incorporate a mechanism which anchors it in position as it exits the skin to withstand fracture, dislodgement, migration, and/or permanent deformation throughout the therapy or treatment period while also enabling differing lengths of lead to be implanted subcutaneously (e.g., shallow anatomy may only allow for the insertion of a lesser (e.g., 4 cm of) lead length, and/or deep anatomy may require insertion of a greater (e.g., 10 cm of) lead length), and/or while maintaining the flexible nature of the percutaneous coiled lead to limit subcutaneous forces (e.g., shearing, compression, bending, and/or tension), and/or while limiting the risk of infection (e.g., by enabling, facilitating, encouraging, and/or avoiding prevention of tissue ingrowth into the helical lead, maintaining a small (e.g., <0.5 mm, <0.6 mm, <0.7 mm, <0.8 mm, <0.9 mm, <1.0 mm, <2 mm, and/or <3 mm) lead diameter at the exit site, limiting pistoning, unwanted or undesired movement, and/or cyclical or repeated movement (e.g., back and forth movement) of the lead across the skin barrier which may introduce bacteria and/or irritants subcutaneously), and or while enabling easy removal in a potentially non-surgical setting (in a non-limiting example to not require the use of a scalpel, blade, and/or dissection) at the end of the treatment period. In an example embodiment, the lead may coil and/or be deformed at the lead exit site, and/or the lead may be sewn and/or tunneled into the skin. In another example embodiment, the lead may be coated in a material and/or texture which grabs (e.g., adheres) to the patient's skin. In another example embodiment, the lead may be coupled with a barbed (e.g., teethed, anchor) material which adheres to the skin and may contain a single tooth or may contain multiple teeth. Materials coupled with or coating the lead may be absorbable by tissue, and/or may be affixed to the lead so as to be removed when the lead is removed, and/or may contain a tab-like part exposed at the exit site to enable removal (e.g., by grabbing and pulling with forceps). In another example embodiment, the lead may be secured at the exit site by a suture pad made from a non-irritating (e.g., fabric and/or gel-like) material which may be secured to the lead (e.g., by folding around the lead, and/or placing over the lead, and/or passing the lead through) and then sutured to the skin by absorbable and/or non-absorbable suture(s) to affix the lead into position.

In an example embodiment, the lead connector may be lockable into the mounting cradle such that it remains in position during normal patient movement, bandage changes, and/or system connection/disconnection, but be removable with a single gloved hand (e.g., soiled by ultrasound gel), a patient or caregiver in a non-clinical setting, and/or a technician or other caregiver in a clinical setting which may or may not have prior education on the removal of the connector from the mounting cradle. In a non-limiting example, the connector may be vertically lockable such that a two-fingered (e.g., thumb and forefinger) squeeze may release the connector from the mounting cradle (e.g., by squeezing on molded tabs to temporarily deform the connector and release it from the cradle).

Although the embodiments of this disclosure have been illustrated in the accompanying drawings and described in the foregoing detailed description, it is to be understood that the present disclosure is not to be limited to just the described embodiments, but that the embodiments described herein are capable of numerous rearrangements, modifications and substitutions without departing from the scope of the claims hereafter. It is, of course, not possible to describe every conceivable combination of components or methodologies for purposes of describing the present specification, but one of ordinary skill in the art may recognize that many further combinations and permutations of the present specification are possible. Each of the components described above may be combined or added together in any permutation to define an introducing device and/or introducing system. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The claims as follows are intended to include all modifications and alterations insofar as they come within the scope of the claims or the equivalent thereof.

The invention claimed is:

1. A lead connector for an electrical stimulator system, the lead connector comprising:

a body including a cable interface, the body defining lead ports;

a blade affixed to the body, the blade having at least one angled portion; and an insert slidably connected to the body, the insert including a handle and a chassis, the chassis defining a lead channel coaxial with the lead ports and blade channels transverse the lead channel to accept the blade, wherein the angled leading edge of the blade provides electrical contact between the cable interface and a lead inserted into the lead channel and extending through at least one of the lead ports.

2. The lead connector of claim 1, wherein the lead connector has an open position and a closed position, and wherein slidably transitioning from the open position to the closed position causes the blade to secure portions of the lead inserted in the lead channel into the blade channels.

3. The lead connector of claim 1, wherein the angled portion of the blade includes a cutting edge to strip or sever the lead when the insert in pushed into the body into a closed position.

4. The lead connector of claim 1, wherein the blade includes two side members, each with one of the angled portions, each of the two side members configured to slide into a different one of the blade channels.

5. The lead connector of claim 1, wherein the handle provides a snap fit to selectively couple the lead connector into a connector base.

6. The lead connector of claim 1, wherein the lead connector has an open position and a closed position, wherein:

the insert includes a first set of forward latches and a first set of rearward latches; and the body includes a second set of forward latches to cooperate with the first set of forward latches to selectively lock the lead connector in the open position, and a second set of rearward latches to cooperate with the first set of rearward latches to selectively lock the lead connector in the closed position.

7. The lead connector of claim 1, wherein the cable interface is a magnetic cradle that defines a jack to accept a conductive pin of the cable, the jacking being surrounded by a magnet ring to magnetically attach the cable to the cable interface.

8. The lead connector of claim 1, wherein the cable interface includes a ring magnet magnetically attaching the cable to the cable interface and a conductive pin to plug into a corresponding jack of the cable.

9. A lead connector for an electrical stimulator system, the lead connector comprising:

a base including a cable interface, the base defining lead ports;

a blade affixed to the body, the blade having at least two sections transverse an axis defined by the lead ports; and a cover rotatably connected to the base, the cover including a handle, blade guides, and port guides, the blade guides defining blade channels each to interface with a different one of the sections of the blade, wherein a portion of each of the sections of the blade provides electrical contact between the cable interface and a lead inserted into at least one of the lead ports.

10. The lead connector of claim 9, wherein the cover is configured to rotate about a first axis that is parallel a second axis defined by the lead ports.

11. The lead connector of claim 9, wherein the lead connector has an open position and a closed position, and wherein rotatably transitioning from the open position to the closed position causes the blade to secure portions of the lead into the blade channels.

12. The lead connector of claim 9, wherein at least one of the sections of the blade includes a cutting edge to strip or sever the lead when the cover is rotatably pushed into the base into a closed position.

13. The lead connector of claim 9, wherein the handle provides a snap fit to selectively couple the lead connector into a connector base.

14. The lead connector of claim 13, wherein the handle is configured to release from the connector base when inwards force is applied the handle and a side of the lead connector opposite the handle.

* * * * *